(12) United States Patent
Flygare et al.

(10) Patent No.: US 11,135,303 B2
(45) Date of Patent: Oct. 5, 2021

(54) PYRROLOBENZODIAZEPINES AND CONJUGATES THEREOF

(71) Applicants: MEDIMMUNE LIMITED, Washington, DC (US); Genentech, Inc., South San Francisco, CA (US)

(72) Inventors: John A. Flygare, South San Francisco, CA (US); Janet L. Gunzner-Toste, South San Francisco, CA (US); Thomas Pillow, South San Francisco, CA (US); Philip Wilson Howard, London (GB); Luke Masterson, London (GB)

(73) Assignee: Medimmune Limited, Cambridge (GB)

( * ) Notice: Subject to any disclaimer, the term of this patent is extended or adjusted under 35 U.S.C. 154(b) by 885 days.

(21) Appl. No.: 13/650,277

(22) Filed: Oct. 12, 2012

(65) Prior Publication Data

US 2013/0266595 A1    Oct. 10, 2013

Related U.S. Application Data

(60) Provisional application No. 61/547,187, filed on Oct. 14, 2011.

(51) Int. Cl.
*A61K 47/68* (2017.01)
*C07D 519/00* (2006.01)
*C07D 487/04* (2006.01)

(52) U.S. Cl.
CPC ...... *A61K 47/6803* (2017.08); *A61K 47/6849* (2017.08); *C07D 487/04* (2013.01); *C07D 519/00* (2013.01)

(58) Field of Classification Search
CPC .. C07D 519/00; C07D 487/04; C07D 243/00; A61K 31/55
(Continued)

(56) References Cited

U.S. PATENT DOCUMENTS 4,816,567 A   3/1989   Cabilly et al.
5,362,852 A   11/1994  Geoghegan
(Continued)

FOREIGN PATENT DOCUMENTS

EP   0522868    1/1993
EP   0875569    11/1998
(Continued)

OTHER PUBLICATIONS

Barginear, M.F., et al. Open Breast Cancer Journal vol. 1 pp. 25-30, published 2009.*
(Continued)

*Primary Examiner* — Theodore R. Howell
*Assistant Examiner* — George W Kosturko
(74) *Attorney, Agent, or Firm* — Faegre Drink Biddle & Reath LLP

(57) ABSTRACT

A conjugate of formula (A):

Figure 1:
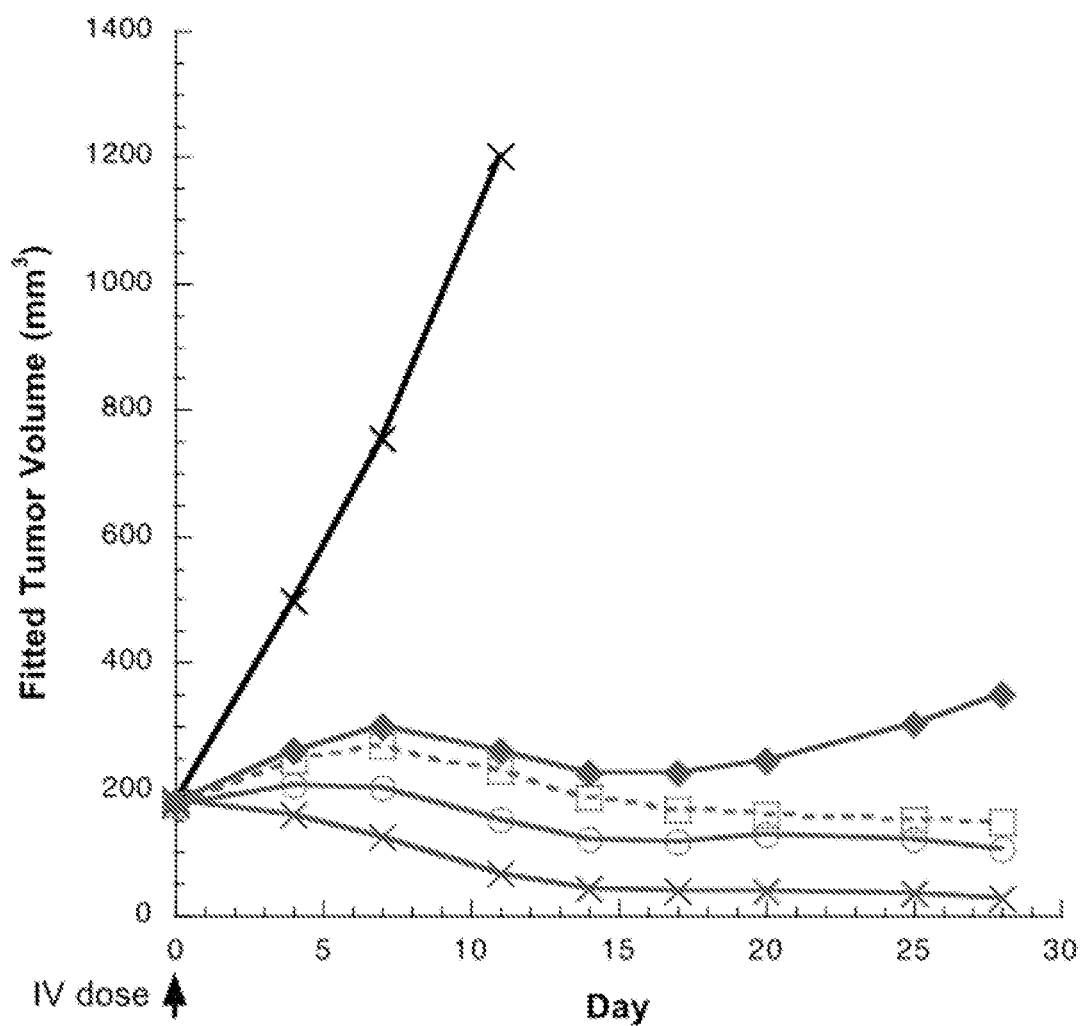

where Y is selected from a single bond, and a group of formulae A1 or A2:

(A1)

(A2)

where N shows where the group binds to the N10 of the PBD moiety;

$R^{L1}$ and $R^{L2}$ are independently selected from H and methyl, or together with the carbon atom to which they are bound form a cyclopropylene group;

CBA represents a cell binding agent;

Q is independently selected from O, S and NH;
(Continued)

$R^{11}$ is either H, or R or, where Q is O, SO$_3$M, where M is a metal cation.

36 Claims, 2 Drawing Sheets

Specification includes a Sequence Listing.

(58) Field of Classification Search
USPC ......... 514/219, 220; 540/484, 485, 492, 496
See application file for complete search history.

(56) References Cited

U.S. PATENT DOCUMENTS

| | | |
|---|---|---|
| 5,440,021 A | 8/1995 | Chuntharapai et al. |
| 5,583,024 A | 12/1996 | McElroy et al. |
| 5,621,002 A | 4/1997 | Bosslet et al. |
| 5,644,033 A | 7/1997 | Seon |
| 5,674,713 A | 10/1997 | McElroy et al. |
| 5,700,670 A | 12/1997 | Yamagishi et al. |
| 5,773,223 A | 6/1998 | Shyamala et al. |
| 5,792,616 A | 8/1998 | Persico et al. |
| 5,854,399 A | 12/1998 | Salomon et al. |
| 5,869,445 A | 2/1999 | Cheever et al. |
| 5,976,551 A | 11/1999 | Mottez et al. |
| 6,011,146 A | 1/2000 | Mottez et al. |
| 6,153,408 A | 11/2000 | Abastado et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,518,404 B1 | 2/2003 | Li et al. |
| 6,534,482 B1 | 3/2003 | Fikes et al. |
| 6,555,339 B1 | 4/2003 | Liaw et al. |
| 6,562,806 B1 * | 5/2003 | Thurston et al. ............. 514/185 |
| 6,602,677 B1 | 8/2003 | Wood et al. |
| 6,677,435 B2 | 1/2004 | Barbas, III et al. |
| 6,759,509 B1 | 7/2004 | King et al. |
| 6,835,807 B1 | 12/2004 | Susaki et al. |
| 7,223,837 B2 | 5/2007 | De Groot et al. |
| 7,375,078 B2 | 5/2008 | Feng |
| 7,521,541 B2 * | 4/2009 | Eigenbrot ........ A61K 47/48538 |
| | | 424/133.1 |
| 7,723,485 B2 | 5/2010 | Junutula et al. |
| 2001/0055751 A1 | 12/2001 | Reiter et al. |
| 2002/0034749 A1 | 3/2002 | Billing-Medel et al. |
| 2002/0042366 A1 | 4/2002 | Thompson et al. |
| 2002/0150573 A1 | 10/2002 | Nussenzweig |
| 2002/0193567 A1 | 12/2002 | Jacobs et al. |
| 2003/0060612 A1 | 3/2003 | Goddard et al. |
| 2003/0062401 A1 | 4/2003 | Hasz et al. |
| 2003/0064397 A1 | 4/2003 | Spancake et al. |
| 2003/0065143 A1 | 4/2003 | Eaton et al. |
| 2003/0091580 A1 | 5/2003 | Mitcham et al. |
| 2003/0096743 A1 | 5/2003 | Senter et al. |
| 2003/0096961 A1 | 5/2003 | Baker et al. |
| 2003/0105292 A1 | 6/2003 | Liaw et al. |
| 2003/0109676 A1 | 6/2003 | Li et al. |
| 2003/0118592 A1 | 6/2003 | Ledbetter et al. |
| 2003/0119121 A1 | 6/2003 | Baker et al. |
| 2003/0119122 A1 | 6/2003 | Baker et al. |
| 2003/0119125 A1 | 6/2003 | Baker et al. |
| 2003/0119126 A1 | 6/2003 | Baker et al. |
| 2003/0119128 A1 | 6/2003 | Baker et al. |
| 2003/0119129 A1 | 6/2003 | Baker et al. |
| 2003/0119130 A1 | 6/2003 | Baker et al. |
| 2003/0119131 A1 | 6/2003 | Baker et al. |
| 2003/0124140 A1 | 7/2003 | Bangur et al. |
| 2003/0124579 A1 | 7/2003 | Mack et al. |
| 2003/0129192 A1 | 7/2003 | Chenault et al. |
| 2003/0130189 A1 | 7/2003 | Senter et al. |
| 2003/0134790 A1 | 7/2003 | Langenfeld |
| 2003/0143557 A1 | 7/2003 | Penner |
| 2003/0157089 A1 | 8/2003 | Xu et al. |
| 2003/0165504 A1 | 9/2003 | Retter et al. |
| 2003/0185830 A1 | 10/2003 | Xu et al. |
| 2003/0186372 A1 | 10/2003 | Baker et al. |
| 2003/0186373 A1 | 10/2003 | Baker et al. |
| 2003/0194704 A1 | 10/2003 | Penn et al. |
| 2003/0206918 A1 | 11/2003 | Fanger et al. |
| 2003/0219806 A1 | 11/2003 | Glucksmann et al. |
| 2003/0224411 A1 | 12/2003 | Stanton et al. |
| 2003/0224454 A1 | 12/2003 | Ryseck et al. |
| 2003/0228319 A1 | 12/2003 | Frantz et al. |
| 2003/0232056 A1 | 12/2003 | Fanger et al. |
| 2003/0232350 A1 | 12/2003 | Afar et al. |
| 2004/0001827 A1 | 1/2004 | Dennis |
| 2004/0005320 A1 | 1/2004 | Thompson et al. |
| 2004/0005538 A1 | 1/2004 | Chen et al. |
| 2004/0005563 A1 | 1/2004 | Mack et al. |
| 2004/0005598 A1 | 1/2004 | DeVaux et al. |
| 2004/0018194 A1 | 1/2004 | Francisco et al. |
| 2004/0018553 A1 | 1/2004 | Billing-Medel et al. |
| 2004/0022727 A1 | 2/2004 | Stanton et al. |
| 2004/0044179 A1 | 3/2004 | Baker et al. |
| 2004/0044180 A1 | 3/2004 | Baker et al. |
| 2004/0052793 A1 | 3/2004 | Carter et al. |
| 2004/0101874 A1 | 5/2004 | Ghosh et al. |
| 2004/0101899 A1 | 5/2004 | Dillon et al. |
| 2004/0121940 A1 | 6/2004 | De Groot et al. |
| 2004/0197325 A1 | 10/2004 | Law et al. |
| 2004/0249130 A1 | 12/2004 | Stanton et al. |
| 2005/0271615 A1 | 12/2005 | Shabat et al. |
| 2006/0116422 A1 | 6/2006 | De Groot et al. |
| 2009/0274713 A1 * | 11/2009 | Chari ................. C07K 5/06026 |
| | | 424/181.1 |

FOREIGN PATENT DOCUMENTS

| | | | |
|---|---|---|---|
| EP | 1295944 | 3/2003 | |
| EP | 1347046 | 9/2003 | |
| EP | 1394274 | 3/2004 | |
| EP | 1439393 | 7/2004 | |
| EP | 1813614 | 8/2007 | |
| FR | WO 2007085930 A1 * | 8/2007 | ........... C07D 487/04 |
| JP | 58-180487 | 10/1983 | |
| JP | 05003790 | 1/1993 | |
| JP | 2004113151 | 4/2004 | |
| WO | WO 199102536 | 3/1991 | |
| WO | WO 199207574 | 5/1992 | |
| WO | WO 199217497 | 10/1992 | |
| WO | WO 199410312 | 5/1994 | |
| WO | WO 199428931 | 12/1994 | |
| WO | WO 199630514 | 10/1996 | |
| WO | WO 199707198 | 2/1997 | |
| WO | WO 199744452 | 11/1997 | |
| WO | WO 199837193 | 8/1998 | |
| WO | WO 199840403 | 9/1998 | |
| WO | WO 199851805 | 11/1998 | |
| WO | WO 199851824 | 11/1998 | |
| WO | WO 199928468 | 6/1999 | |
| WO | WO 199946284 | 9/1999 | |
| WO | WO 199958658 | 11/1999 | |
| WO | WO 0012130 | 3/2000 | |
| WO | WO 0014228 | 3/2000 | |
| WO | WO 200012507 | 3/2000 | |
| WO | WO 2000012508 | 3/2000 | |
| WO | WO 0020579 | 4/2000 | |
| WO | WO 0022129 | 4/2000 | |
| WO | WO 0032752 | 6/2000 | |
| WO | WO 0036107 | 6/2000 | |
| WO | WO 0040614 | 7/2000 | |
| WO | WO 0044899 | 8/2000 | |
| WO | WO 200053216 | 9/2000 | |
| WO | WO 200055351 | 9/2000 | |
| WO | WO 2000053216 | 9/2000 | |
| WO | WO 0075655 | 12/2000 | |
| WO | WO 200100244 | 1/2001 | |
| WO | WO 200116318 | 3/2001 | |
| WO | WO 200138490 | 5/2001 | |
| WO | WO 200140269 | 6/2001 | |
| WO | WO 200140309 | 6/2001 | |
| WO | WO 200141787 | 6/2001 | |
| WO | WO 200145746 | 6/2001 | |
| WO | WO 200146232 | 6/2001 | |

(56) References Cited

FOREIGN PATENT DOCUMENTS

| | | |
|---|---|---|
| WO | WO 200146261 | 6/2001 |
| WO | WO 200148204 | 7/2001 |
| WO | WO 200153463 | 7/2001 |
| WO | WO 200157188 | 8/2001 |
| WO | WO 200162794 | 8/2001 |
| WO | WO 200166689 | 9/2001 |
| WO | WO 200172830 | 10/2001 |
| WO | WO 200172962 | 10/2001 |
| WO | WO 200175177 | 10/2001 |
| WO | WO 200177172 | 10/2001 |
| WO | WO 200188133 | 11/2001 |
| WO | WO 200190304 | 11/2001 |
| WO | WO 200194641 | 12/2001 |
| WO | WO 200198351 | 12/2001 |
| WO | WO 200202587 | 1/2002 |
| WO | WO 200202624 | 1/2002 |
| WO | WO 200202634 | 1/2002 |
| WO | WO 200206317 | 1/2002 |
| WO | WO 200206339 | 1/2002 |
| WO | WO 200210187 | 2/2002 |
| WO | WO 200210382 | 2/2002 |
| WO | WO 200212341 | 2/2002 |
| WO | WO 200213847 | 2/2002 |
| WO | WO 200214503 | 2/2002 |
| WO | WO 200216413 | 2/2002 |
| WO | WO 200222153 | 3/2002 |
| WO | WO 200222636 | 3/2002 |
| WO | WO 200222660 | 3/2002 |
| WO | WO 200222808 | 3/2002 |
| WO | WO 200224909 | 3/2002 |
| WO | WO 200226822 | 4/2002 |
| WO | WO 200230268 | 4/2002 |
| WO | WO 200238766 | 5/2002 |
| WO | WO 200254940 | 7/2002 |
| WO | WO 200259377 | 8/2002 |
| WO | WO 200260317 | 8/2002 |
| WO | WO 200261087 | 8/2002 |
| WO | WO 200264798 | 8/2002 |
| WO | WO 200271928 | 9/2002 |
| WO | WO 200272596 | 9/2002 |
| WO | WO 200278524 | 10/2002 |
| WO | WO 200281646 | 10/2002 |
| WO | WO 200283866 | 10/2002 |
| WO | WO 200286443 | 10/2002 |
| WO | WO 200288170 | 11/2002 |
| WO | WO 200289747 | 11/2002 |
| WO | WO 200292836 | 11/2002 |
| WO | WO 200294852 | 11/2002 |
| WO | WO 2002088172 | 11/2002 |
| WO | WO 200298358 | 12/2002 |
| WO | WO 200299074 | 12/2002 |
| WO | WO 200299122 | 12/2002 |
| WO | WO 2002101075 | 12/2002 |
| WO | WO 2002102235 | 12/2002 |
| WO | WO 200216429 | 1/2003 |
| WO | WO 2003000842 | 1/2003 |
| WO | WO 2003002717 | 1/2003 |
| WO | WO 2003003906 | 1/2003 |
| WO | WO 2003003984 | 1/2003 |
| WO | WO 2003004529 | 1/2003 |
| WO | WO 2003004989 | 1/2003 |
| WO | WO 2003008537 | 1/2003 |
| WO | WO 2003009814 | 2/2003 |
| WO | WO 2003014294 | 2/2003 |
| WO | WO 2003016475 | 2/2003 |
| WO | WO 2003016494 | 2/2003 |
| WO | WO 2003018621 | 3/2003 |
| WO | WO 2003022995 | 3/2003 |
| WO | WO 2003023013 | 3/2003 |
| WO | WO 2003024392 | 3/2003 |
| WO | WO 2003025138 | 3/2003 |
| WO | WO 2003025148 | 3/2003 |
| WO | WO 2003025228 | 3/2003 |
| WO | WO 2003026493 | 4/2003 |
| WO | WO 2003026577 | 4/2003 |
| WO | WO 2003029262 | 4/2003 |
| WO | WO 2003029277 | 4/2003 |
| WO | WO 2003029421 | 4/2003 |
| WO | WO 2003034984 | 5/2003 |
| WO | WO 2003035846 | 5/2003 |
| WO | WO 2003042661 | 5/2003 |
| WO | WO 2003043583 | 5/2003 |
| WO | WO 2003045422 | 6/2003 |
| WO | WO 2003048202 | 6/2003 |
| WO | WO 2003054152 | 7/2003 |
| WO | WO 2003055439 | 7/2003 |
| WO | WO 2003055443 | 7/2003 |
| WO | WO 2003060612 | 7/2003 |
| WO | WO 2003062401 | 7/2003 |
| WO | WO 2003072035 | 9/2003 |
| WO | WO 2003072036 | 9/2003 |
| WO | WO 2003077836 | 9/2003 |
| WO | WO 2003081210 | 10/2003 |
| WO | WO 2003083041 | 10/2003 |
| WO | WO 2003083047 | 10/2003 |
| WO | WO 2003083074 | 10/2003 |
| WO | WO 2003087306 | 10/2003 |
| WO | WO 2003087768 | 10/2003 |
| WO | WO 2003088808 | 10/2003 |
| WO | WO 2003089624 | 10/2003 |
| WO | WO 2003089904 | 10/2003 |
| WO | WO 2003093444 | 11/2003 |
| WO | WO 2003097803 | 11/2003 |
| WO | WO 2003101283 | 12/2003 |
| WO | WO 2003101400 | 12/2003 |
| WO | WO 2003104270 | 12/2003 |
| WO | WO 2003104275 | 12/2003 |
| WO | WO 2003104399 | 12/2003 |
| WO | WO 2003105758 | 12/2003 |
| WO | WO 2004000221 | 12/2003 |
| WO | WO 2004000997 | 12/2003 |
| WO | WO 2004001004 | 12/2003 |
| WO | WO 2004005598 | 1/2004 |
| WO | WO 2004009622 | 1/2004 |
| WO | WO 2004011611 | 2/2004 |
| WO | WO 2004015426 | 2/2004 |
| WO | WO 2004016225 | 2/2004 |
| WO | WO 2004020583 | 3/2004 |
| WO | WO 2004020595 | 3/2004 |
| WO | WO 2004022709 | 3/2004 |
| WO | WO 2004022778 | 3/2004 |
| WO | WO 2004027049 | 4/2004 |
| WO | WO 2004031238 | 4/2004 |
| WO | WO 2004032828 | 4/2004 |
| WO | WO 2004032842 | 4/2004 |
| WO | WO 2004040000 | 5/2004 |
| WO | WO 2004042346 | 5/2004 |
| WO | WO 2004043361 | 5/2004 |
| WO | WO 2004043963 | 5/2004 |
| WO | WO 2004044178 | 5/2004 |
| WO | WO 2004045516 | 6/2004 |
| WO | WO 2004045520 | 6/2004 |
| WO | WO 2004045553 | 6/2004 |
| WO | WO 2004046342 | 6/2004 |
| WO | WO 2004047749 | 6/2004 |
| WO | WO 2004048938 | 6/2004 |
| WO | WO 2004053079 | 6/2004 |
| WO | WO 2004058309 | 7/2004 |
| WO | WO 2004063355 | 7/2004 |
| WO | WO 2004063362 | 7/2004 |
| WO | WO 2004063709 | 7/2004 |
| WO | WO 2004065576 | 8/2004 |
| WO | WO 2004065577 | 8/2004 |
| WO | WO 2004074320 | 9/2004 |
| WO | WO 2005023814 | 3/2005 |
| WO | WO 2005082023 | 9/2005 |
| WO | WO 2005085251 | 9/2005 |
| WO | WO 2006111759 | 10/2006 |
| WO | WO 2007044515 | 4/2007 |
| WO | WO 2007085930 | 8/2007 |
| WO | WO 2007089539 | 8/2007 |
| WO | WO 2007089539 A1 * | 8/2007 ........... C07D 487/04 |
| WO | WO 2009052249 | 4/2009 |

(56) References Cited

FOREIGN PATENT DOCUMENTS

| WO | WO 2010091150 | 8/2010 |
|---|---|---|
| WO | WO 2011130598 | 10/2011 |
| WO | WO 2013055987 | 4/2013 |

OTHER PUBLICATIONS

Vlahov, I.L., et al., Bioorganic and Medicinal Chemistry Letters vol. 16 pp. 5093-5096. Published 2006.*
Berry, J.M. et al., Bioorganic and Medicinal Chemistry Letters vol. 12 pp. 1413-1416. Published 2002.*
Rudikoff et al (Proceedings of the National Academy of Sciences, 1982. vol. 79, p. 1979).*
MacCallum et al. (Journal of Molecular Biology,1996. vol. 262, pp. 732-745).*
Wu et al. (Journal of Molecular Biology,1999. vol. 294, pp. 151-162).*
Kamal, A. et al., Bioorganic and Medicinal Chemistry Letters vol. 18, pp. 3769-3773. Published 2008.*
Howard et al (Bioorganic and Medicinal Chemistry Letters vol. 19 pp. 6463-6466 published 2009) (Year: 2009).*
Kamal (Bioorganic and Medicinal Chemistry vol. 17 pp. 1557-1572 published 2009 (Year: 2009).*
Vhalov et al (Bioorganic and Medicinal Chemistry Letters vol. 16 pp. 5093-5096. Published 2006) (Year: 2006).*
Kamal et al (Bioorganic and Medicinal Chemistry Letters vol. 18 pp. 3769-3773 published 2008 (Year: 2008).*
Kamal (BOMC vol. 17 1557-1572 published 2009) (Year: 2009).*
Hartley (Cancer Research vol. 64 pp. 6693-6699 published 2004). (Year: 2004).*
Adair, J.R. et al., "Antibody-drug conjugates—a perfect synergy," Exp. Opin. Biol. Ther. (2012) 16 p.
Amiel J., et al., "Heterozygous endothelin receptor B {EDNRB) mutations in isolated Hirschsprung disease," Hum. Mol. Genet. 5, 355-357, 1996.
Amir et al., "Self-Immolative Dendrimers," (2003) Angew. Chem. Int. Ed. 42:4494-4499.
Amsberry, et al, "The Lactonization of 2'-Hydroxyhydrocinnamic Acid Amides: A Potential Prodrug for Amines," (1990) J. Org. Chem. 55:5867-5877.
Antonow. D. and Thurston. D.E., "Synthesis of DNA-Interactive Pyrrolo[2, 1-c][1,4]benzodiazepines (PBDs)," Chem. Rev. 2011, 111 (4), 2815-2864.
Arai H., et al., "Molecular cloning of human endothelin receptors and their expressiOn in vascular endothelial cells and smooth muscle cells," Jpn. Circ. J. 56, 1303-1307, 1992.
Arai H., et al., "The Human Endotbelin-B Receptor Gene. Structural Organization and Chromosomal Assignment," J. Biol. Chem. 268, 3463-3470, 1993.
Arima, et al., "Studies on Tomaymycin, A Ne'Iv Antibiotic. Isolation and Properties of Toma Ymycin," J. Antibiotics, 25, 437-444 (1972).
Attie T., et al., "Mutation of the endothelin-receptor B gene in Waardenburg-Hirschsprung disease," Hum. Mol. Genet. 4, 2407-2409, 1995.
Auricchio A., et al., "Endothelin-B receptor mutations in patients with isolated Hirschsprung disease from a non-inbred population," Hum. Mol. Genet. 5:351-354, 1996.
Bahrenberg et al., "Reduced Expression of PSCA, a Member of the LY-6 Family of Cell Surface Antigens, in Bladder, Esophagus, and Stomach Tumors," Biochem. Biophys. Res. Commun. (2000) 275(3):783-788.
Barel M., et al., "Evidence for a new transcript of the Epstein-Barr virus/C3d receptor (CR2, CD21) which is due to alternative exon usage," Mol. lmmunol. 35, 1025-1031, 1998.
Barella et al., "Sequence variation of a novel heptahelical leucocyte receptor through alternative transcript formation," (1995) Biochem. J. 309:773-779.

Barginear, M. F. et al., Open Breast Cancer Journal, 2009, vol. 1, pp. 25-30.
Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.
Beck et al., "DNA Sequence Analysis of 66 kb of the Human MHC Class II Region Encoding a Cluster of Genes for Antigen Processing," (1992) J. Mol. Biol. 228:433-441.
Beck et al., "Evolutionary Dynamics of Non-coding Sequences Within the Class II Region of the Human MHC," (1996) J. Mol. Biol. 25 255:1-13.
Berge, et al., "Pharmaceutical Salts," J. Pharm. Sci., 66, 1-19 (1977).
Blumberg H., et al., "lnterleukin 20: Discovery, Receptor Identification, and Role in Epidermal Function," Cell 104, 9-19, 2001.
Bose, et al., "New Approaches to Pyrrol0[2,1-c][1,4]Benzodiazepines: Synthesis, DNA-Ihnding and Cytotoxicity of DC-81," Tetrahedron, 48, 751-758 (1992).
Bourgeois C., et al., "Endothelin-1 and ETA Receptor Expression in Vascular Smooth Muscle Cells from Human Placenta: A New ETA Receptor Messenger Ribonucleic Acid is Generated by Alternative Splicing of Exon 3," J. Clin. Endocrinol. Metab. 82, 3116-3123, 1997.
Brinster et al., "Introits increase transcriptional efficiency in transgenic mice," (1988) Proc. Natl. Acad. Sci. USA 85:836-840.
Buchman and Berg "Comparison of lntron-Dependent and Intron-Independent Gene Expression," (1988) Mol. Cell. Biol. 8:4395.
Carl et al., "A Novel Connector Linkage Applicable in Prodrug Design," (1981) J. Med. Chern. 24:479-480.
Carlsson et al., "Protein Thiolation and Reversible Protein-Protein Conjugation," (1978) Biochem. J. 173:723-737.
Carter, P., "Potent antibody therapeutics by design," (2006) Nature Reviews Immunology 6:343-357.
CellTiter-Glo Luminescent Cell Viability Assay, Promega Corp. Technical Bulletin TB288, dated Jan. 13, 2012 (14 pages).
Chakravarty et al., "Plasmin-Activated Prodrugs for Cancer Chemotherapy. 2. Synthesis and Biological Activity of Peptidyl Derivatives of Doxorubicin," (1983) J. Med. Chern. 26:638-644.
Chan, J. and Watt, V.M., "eek and erk, new members of the eph subclass of receptor protein-tyrosine kinases," Oncogene 6 (6), 1057-1061 (1991).
Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).
Child et al., "Translational Control by an Upstream Open Reading Frame in the HER-2/neu Transcript," (1999) J. Bioi. Chern. 274: 24335-24341.
Cho et al., "Structure of the extracellular region of HER2 alone and in complex with the Herceptin Fab," Nature 421, 756-760, 2003.
Ciccodicola, A , et al., "Molecular characterization of a gene of the 'EGF family' expressed in undifferentiated human NTERA2 teratocarcinoma cells," EMBO J. 8 (7):1987-1991 (1989).
Clackson et al., "Making antibody fragments using phage display libraries," (1991) Nature, 352:624-628.
Clark H.F., et al., "The Secreted Protein Discovery Initiative (SPDI], a Large-Scale Effort to Identify Novel Human Secreted and Transmembrane Proteins: A Bioinformatics Assessment," Genome Res. 13, 2265-2270, 2003.
Collins, "Generation and initial analysis of more than 15,000 full-length human and mouse eDNA sequences," Proc. Natl. Acad. Sci. U.S.A. 99 (26):16899-16903 (2002).
Corey E. Quinn JE, Buhler KR, et al., "LuCap35: a new model of prostate cancer progression to androgen independence." The Prostate 2003;55:239-46.
Coussens L., et al., "Tyrosine Kinase Receptor with Extensive Homology to EGF Receptor Shares Chromosomal Location With neu Oncogene," Science (1985) 230(4730):1132-1139.
Cragg et al., "The alternative transcript of CD79b is overexpressed in B-CLL and inhibits signaling for apoptosis," Blood (2002) 100 (9):3068-3076.

(56) References Cited

OTHER PUBLICATIONS

Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.
Crouch et al., "The use• of ATP bioluminescence as a measure of cell proliferation and cytotoxicity," (1993) J. Immunol. Meth. 160:81-88.
Davis et al., "Identification of a family of Fe receptor homo logs with preferential B cell expression," (2001) Proc. Natl. Acad. Sci. USA 98(17):9772-9777.
de Groot et al., ""Cascade-Release Dendrimers" Liberate All End Groups upon a Single Triggering Event in the Dendritic Core," (2003) Angew. Chem. Int. Ed. 42:4490-4494.
de Groot et al., "Elongated Multiple Electronic Cascade and Cyclization Spacer Systems in Activatible Anticancer Prodrug for Enhanced Drug Release," (2001) J. Org. Chem. 66:8815-8830.
Dennis et al., (2002) "Albumin Binding as a General Strategy for Improving The Pharmacokinetics of Proteins" J Biol Chem. 277:35035-35043.
Dijke, P., et al., "Characterization of Type I Receptors for Transforming Growth Factor-beta and Activin," Science 264 (5155):101-104 (1994).
Dobner et al., "Differentiation-specific expression of a novel G protein-coupled receptor from Burkitt's lymphoma," (1992) Eur. J. lmmunol. 22:2795-2799.
Dono et al., "Isolation and Characterization of the CRI PTO Autosomal Gene and its X-linked Related Sequence," Am. J. Hum. Genet. 49:555-565, 1991.
Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.
Doronina et al., "Enhanced Activity of Monomethylauristatin F through Monoclonal Antibody Delivery: Effects of Linker Technology on Efficacy and Toxicity," (2006) Bioconj. Chem. 17:114-124.
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chemistry, 2002, 13,855-869.
Dubowchik, et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.
Dumoutier L., et al., "Cutting Edge: STAT Activation by IL-19, IL-20 and mda-7 Through IL-20 Receptor Complexes of Two Types," J. Immunol 167, 3545-3549, 2001.
Ehsani A., et al., "Characterization of a New Allele of the Human ERBB2 Gene by Allele-Specific Competition Hybridization," (1993) Genomics 15, 426-429.
Eliel, E. and Wilen. S., "Stereochemistry of Organic Compounds", John Wiley & Sons. Inc., New York, 1994.
Elshourbagy N.A., et al., "Molecular Characterization and Regulation of the Human Endothelin Receptors," J. Biol. Chem. 268, 3873-3879, 1993.
Erickson et al., "Antibody-Maytansinoid Conjugates are Activated in Targeted Cancer Cells by Lysosomal Degradation and Linker-Dependent Intracellular Processing," (2006) Cancer Res. 66(8): 1-8.
Feild, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.
Fields, G. and Noble, R. (1990) "Solid phase peptide synthesis utilizing 9-fluoroenylmethoxycarbonyl amino acids", Int. J. Peptide Protein Res. 35:161-214.
Flanagan et al., "The Ephrins and EPH Receptors in Neural Development," Annu. Rev. Neurosci. 21:309-345 (1998).
Fox et al., "cDNA cloning and tissue distribution of five human EPH-like receptor protein-tyrosine kinases," Oncogene 10 (5):897-905 (1995).

Fuchs S., et al., "Functional Characterization of Three Mutations of the Endothelin B Receptor Gene in Patients With Hirschsprung's Disease: Evidence for Selective Loss of Gi Coupling," Mol. Med. 7, 115-124, 2001.
Fujisaku et al., "Genomic Organization and Polymorphisms of the Human C3d/Epstein-Barr Virus Receptor," (1989) J. Biol. Chem. 264 (4):2118-2125.
Gary S.C., et al., "cDNA cloning chromosomal localization, and expression analysis of human BEHAB/brevican, a brain specific proteoglycan regulated during cortical development and in glioma," Gene 256, 139-147, 2000.
Gaugitsch, H.W., et al., "A Novel Transiently Expressed, Integral Membrane Protein Linked to Cell Activation. Molecular Cloning Via the Rapid Degradation Signal Auuua," (1992) J. Biol. Chem. 267 (16):11267-11273.
Geiser et al "Automation of solid-phase peptide synthesis" in Macromolecular Sequencing and Synthesis, Alan R. Liss, Inc., 1988, pp. 199-218.
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz et al., "A Comparison between the Sulthydryl Reductants Tris(2-carboxyethyl)phosphine and Dithiothreitol for Use in Protein Biochemistry," (1999) Anal. Biochem. vol. 273:73-80.
Glynne-Jones et al., "TENB2, A Proteogl YCAN Identified in Prostate Cancer that is Associated With Disease Progression and Androgen Independence," (2001) Int J Cancer. Oct. 15; 94(2): 178-184.
Gordon et al., "Somatic hypermutation of the B cell receptor genes 829 (lgf3, CD79b) and mbl (lga, CD79a)," PNAS, Apr. 1, 2003, vol. 100, No. 7, 4126-4131.
Gregson et al., "Design, Synthesis, and Evaluation of a Novel Pyrrolobenzodiazepine DNA-Interactive Agent with Highly Efficient Cross-Linking Ability and Potent Cytotoxicity," J. Med. Chem. 2001 , 44, 737-748.
Gregson et al., "Synthesis of a novel C2/C2'-exo unsaturated pyrrolobenzodiazepine cross-linking agent with remarkable DNA binding affinity and cytotoxicity," Chem. Commun. 1999, 797-798.
Gu Z., et al., "Prostate stem cell antigen (PSCA) expression increases with high gleason score, advanced stage and bone metastasis in prostate cancer," Oncogene 19, 1288-1296, 2000.
Guselnikov et al., "A family of highly diverse human and mouse genes structurally links leukocyte FcR, gp42 and PECAM-1," Immunogenetics 54 (2):87-95 (2002).
Ha et al., "Molecular Cloning and Expression Pattern of a Human Gene Homologous to the Murine mb-1 Gene," (1992) J. lmmunol. 148(5):1526-1531.
Haendler B., et al., "Molecular Cloning of Human Endothelin (ET) Receptors ETA and ETB," J. Cardiovasc. Pharmacal. 20, s1-S4, 1992.
Hamann P. "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.
Hara, et al., "DC 102, A New Glycosidic Pyrrolo(1,4)Benzodiazepine Antibiotic Produced by *Streptomyces* Sp.," J. Antibiotics, 41 , 702-704 (1988).
Hartley JA: "The development of pyrrolobenzodiazepines as antitumour agents", Expert Opinion on Investigational Drugs, Ashley Publications Ltd., vol. 28, No. 6, Jan. 1, 2011, pp. 733-744.
Hashimoto et al., "Chromosomal localization, genomic structure, and allelic polymorphism of the human CD79a (lg-alpha/mb-l) gene," (1994) Immunogenetics 40(4 ):287-295.
Hay et al., "A 2-Nitroimidazole Carbamate Prodrug of 5-Amin0-1-(Chloromethyl)-3-[(5,6,7-Trimethoxyindol-2-YL)Carbonyl] -1,2-Dihydr0-3H-Benz[E]Indole (Amino-SECO-CBI-TMI) for Use With ADEPT and GDEPT," (1999) Bioorg. Med. Chem. Lett. 9:2237-2242.
Herdwijn et al., "Synthesis of trans(+ )6-phenoxyacetamido-1-methylene-3,3-dicarboxymethyl-1-carbapenam," Canadian Journal of Chemistry. 1982, 60, 2903-2907.

(56) References Cited

OTHER PUBLICATIONS

Hermanson, G.T., "Heterobifunctional Cross-linkers," (1996) Bioconjugate Techniques; Academic Press: New York, p. 234-242.
Hochlowski, et al., "Abbeymycin, A New Anthramycin-Type Antibiotic Produced by a Streptomycete," J. Antibiotics, 40, 145-148 (1987).
Hofstra R.M.W., et al., "A homozygous mUtation in the endothelin-3 gene associated with a combined Waardenburg type 2 and Hirschsprung phenotype (Shah-Waardenburg syndrome)," Eur. J. Hum. Genet. 5, 180-185, 1997.
Hofstra R.M.W., et al., "Mutations in Hirschsprung Disease: When Does a Mutation Contribute to the Phenotype," Nat. Genet. 12, 445-447, 1996.
Horie et al., "Identification and Characterization of TMEFF2, a Novel Surviv Factor for Hippocampal and Mesencephalic Neurons," (2000) Genornics 67: 146-152.
Hubert, R.S., et al., "STEAP: A prostate-specific cell-surface antigen highly expressed in human prostate tumors," (1999) Proc. Natl. Acad. Sci. U.S.A. 96 (25):14523-14528.
Hurley and Needham-VanDevanter, "Covalent Binding of Antitumor Antibiotics in the Minor Groove of DNA. Mechanism of Action of CC-1065 and the Pyrrolo( 1,4) benzodiazepines," Ace. Chem. Res., 19, 230-237 (1986).
Ide et al., "Cloning of human bone morphogenetic protein type IB receptor (BMPRIB) and its expression in prostate cancer in comparison with other BMPRs," Oncogene (1997) 14, 1377-1382.
Itoh et al., "Sibanomicin, A New Pyrrolo[1,4]-Benzodiazepine Antitumor Antibiotic Produced by a *Micromonospora* Sp.," Antibiotics, 41, 1281-1284 (1998).
Remmers et al., "Conformations of complexes between pyrrolo[1,4]benzodiazepines and DNA segments," J Med Chem. Dec. 1986;29(12):2492-2503.
Janjigian et al: "A phase I trial of SJG-136 (NSC#694501) in advanced solid tumors", Cancer Chemotherapy and Pharmacology, Springer, vo 1. 65, No. 5, Aug. 12, 2009, pp. 833-838.
Jeffrey et al., "Design, Synthesis, and in Vitro Evaluation of Dipeptide-Based Antibody Minor Groove Binder Conjugates," (2005) J. Med. Chem. 48: 1344-1358.
Jones et al., "Releasable Luciferin—Transporter Conjugates: Tools for the Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Junutula et al., "Rapid identification of reactive cysteine residues for site-specific labeling of antibody-Fabs," (2008) Jour of lmmun. Methods 332:41-52.
Junutula, et al., "Site-specific conjugation of a cytotoxic drug to an antibody improves the therapeutic index," 2008b Nature Biotech., 26(8):925-932.
Kamal et al: "Development of Pyrrolo[2,1-c] [1,4]benzodiazepine a-Galactoside Prodrugs for Selective Therapy of Cancer by ADEPT and PMT", Chemmedchem, Wiley-VCH Verlag., vol. 3, No. 5, May 19, 2008, pp. 794-802.
Kang, G-D., et al., "Synthesis of a novel C2-aryl substituted 1,2-unsaturated pyrrolobenzodiazepine," Chem. Commun, 2003, 1680-1689.
Kasahara et al., "Nucleotide sequence of a chimpanzee DOB eDNA clone," (1989) Immunogenetics 30(1):66-68.
King et al., "Facile synthesis of maleimide bifunctional Jinkers," (2002) Tetrahedron Letters 43:1987-1990.
Kingsbury et al., "A Novel Peptide Delivery System Involving Peptidase Activated Prodrugs as Antimicrobial Agents. Synthesis and Biological Activity of Peptidyl Derivatives of 5 Fluorouracil," (1984) J. Med. Chern. 27:1447-1451.
Kohler et al., "Continuous cultures of fused cells secreting antibody of predefined specificity," (1975) Nature 256:495-497.
Kohn, "Anthramycin," In Antibiotics Ill. Springer-Verlag, New York, pp. 3-11 (1975).

Kojima et al., "Molecular Cloning and Expression of Megakaryocyte Potentiating Factor eDNA," The Journal of Biological Chemistry, vol. 270, No. 37, Issue of Sep. 15, pp. 21984-21990, 1995.
Konishi, et al., "Chicamycin, A New Antitumor Antibiotic. II. Structure Determination of Chicamycins A and B," J. Antibiotics, 37, 200-206 (1984).
Kovtun et al., "Antibody-Drug Conjugates Designed to Eradicate Tumors with Homogeneous and Heterogeneous Expression of the Target Antigen," (2006) Cancer Res. 66(6):3214-3121.
Kuhns J.J., et al., "Poor Binding of a HER-2/neu Epitope (GP2) to HLA-A2.1 is due to a Lack of Interactions with the Center of the Peptide," J. Biol. Chem. 274, 36422-36427, 1999.
Kuminoto, et al., "Mazethramycin, A New Member of Anthramycin Group Antibiotics," J. Antibiotics, 33, 665-667 (1980).
Kurebayashi et al., "Isolation and characterization of a new human breast cancer cell line, KPL-4, expressing the Erb B family receptors and interleukin•6," (1999) Brit. Jour. Cancer 79(5-6):707-717.
Lambert J., "Drug-conjugated monoclonal antibodies for the treatment of cancer," (2005) Current Opin. in Pharmacal. 5:543-549.
Langley and Thurston, "A Versatile and Efficient Sy n t hesis of Carbinolamine-Containing Pyrrolo[1,4]benzodiazepines via the Cyclization of N-(2-Aminobenzoyl)pyrrolidine-2-carboxaldehyde Diethyl Thioacetals: Total Synthesis of Prothracar cin," J. Org. Chem. , 52, 91-97 (1987).
Larhammar et al., "Sequence of Gene and eDNA Encoding Murine Major Histocompatibility Complex Class II Gene AP2*," (1985) J. Biol. Chem. 260(26):14111-14119.
Launcy et al., "TRPM4 is a Ca2+-Activated Nonselective Cation Channel Mediating Cell Membrane Depolarization," Cell 109 (3):397-407 (2002).
Law et al., "Lymphocyte Activation Antigen CD70 Expressed by Renal Cell Carcinoma is a Potential Therapeutic Target for Anti-CD70 Antibody-Drug Conjugates," (2006) Cancer Res. 66(4):2328-2337.
Le et al., "Primary structure and expression of a naturally truncated human P2X ATP receptor subunit from brain and immune system," (1997) FEBS Lett. 418(1-2):195-199.
Leber, et al.,"A Revised Structure for Sibiromycin," J. Am. Chern. Soc., 110, 2992-2993 (1988).
Leimgruber, et at., "The Structure of Anthramycin," J. Am. Chem. Soc., 87, 5791-5795 (1965).
Levenson et al., "MCF-7: The First Hormone-responsive Breast Cancer Cell Line," (1997) Cancer Res. 57(15):3071-3078.
Liang et al., "The Gene for a Novel Transmembrane Protein Containing Epidermal Growth Factor and Follistatin Domains is Frequently Hypermethylated in Human Tumor Cells," (2000) Cancer Res. 60:4907-4912.
Manfre et al., "Syntheses of Proline Analogues as Potential Mechanism-Based Inhibitors of Proline Dehydrogenase: 4-Methylene-L-, (E)- and (Z)-4-(Fluoromethylene)-L-, cis- and trans-5-Ethynyl-(±)-, and cis- and trans-5-Vinyl-L-proline," J. Org. Chem. 1992, 57, 2060-2065.
Marks et al., "By-passing Immunization, Human Antibodies from V-gene Libraries Displayed on Phage," (1991) J. Mol. Biol., 222:581-597.
Mastroberardino et al., "Amino-acid transport by heterodimers of 4F2hc/CD98 and members of a permease family," Nature 395 (6699):288-291 (1998).
McDonagh, "Engineered antibody-drug conjugates with defined sites and stoichiometries of drug attachment," (2006) Protein Eng. Design & Sel. 19(7): 299-307.
Mendoza et al., "Inhibition of Ligand-mediated HER2 Activation in Androgen-independent Prostate Cancer," (2002) Cancer Res. 62:5485-5488.
Miller et al., "Design, Construction, and In Vitro Analyses of Multivalent Antibodies," (2003) Jour. of Immunology 170:4854-4861.
Miller et al., "IRTAs: a new family of immunoglobulinlike receptors differentially expressed in B cells," Blood 99(8):2662-2669 (2002).
Miura et al., "RP1OS is Associated With MD-1 and Transmits an Activation Signal in Human B Cells," (1996) Genomics 38(3):299-304.

(56) References Cited

OTHER PUBLICATIONS

Miura et al., "RP1OS is Associated With MD-1 and Transmits an Activation Signal in Human B Cells," (1998) Blood 92:2815-2822.
Moore M., et al., "Molecular cloning of the eDNA encoding the Epstein-Barr virus/C3d receptor (complement receptor type 2) of human B lymphocytes," Proc. Natl. Acad. Sci. U.S.A. 84, 9194-9198, 1987.
Morrison et al., "Chimeric human antibody molecules: Mouse antigen-binding domains with human constant region domains," (1984) Proc. Natl. Acad. Sci. USA, 81:6851-6855.
Muller et al., "Cloning and sequencing of the eDNA encoding the human homologue of the murine immunoglobulin-associated protein B29," (1992) Eur. J. lmmunol. 22 (6): 1621-1625.
Mungall A.J., et al., "The DNA sequence and analysis of human chromosome 6," Nature 425, 805-811, 2003.
Nagase T., et al., "Prediction of the Coding Sequences of Unidentified Human Genes. XVII. The Complete Sequences of 100 New eDNA Clones from Brain Which Code for Large Proteins in vitro," (2000) DNA Res. 7(2):143-150.
Nakamuta M., et al., "Cloning and Sequence Analysis of a cDNA Encoding Human Non-Selective Type of Endothelin Receptor," Biochem. Biophys. Res. Commun. 177, 34-39, 1991.
Nakayama et al., "Altered Gene Expression upon BCR Cross-Linking in Burkitt's Lymphoma B Cell Line," (2000) Biochem. Biophys. Res. Commun. 277(1):124-127.
Naruse et al., "The HLA-DOB gene displays limited polymorphism with only one amino acid substitution," (2002) Tissue Antigens 59:512-519.
Neuberger and Williams, "The intron requirement for immunoglobulin gene expression is dependent upon the promoter," (1988) Nucleic Acids Res. 16:6713-6724.
Nicolaou et al., "Calicheamicin 01: A Rationally Designed Molecule with Extremely Potent and Selective DNA Cleaving Properties and Apoptosis Inducing Activity," Angew Chem. Intl. Ed. Engl. (1994) 33:183-186.
Nilius et al., "Voltage Dependence of the Ca2+-activated Cation Channel TRPM4," The Journal of Biological Chemistry, vol. 278, No. 33, Issue of Aug. 15, pp. 30813-30820, 2003.
Ogawa Y., et al., "Molecular Cloning of a Non-Isopeptide-Selective Human Endothelin Receptor," Biochem. Biophys. Res. Commun. 178, 248-255, 1991.
Okamoto Y., et al. "Palmitoylation of Human EndothelinB," Biol. Chem. 272, 21589-21596, 1997.
Parrish-Novak J., et al., "lnterleukins 19, 20, and 24 Signal through Two Distinct Receptor Complexes," J. Biol. Chem. 277, 47517-47523, 2002.
Payne, G. "Progress in immunoconjugate cancer therapeutics," (2003) Cancer Cell 3:207-212.
PCT/US2012/059864 International Search Report and Written Opinion dated Dec. 21, 2012 (10 pages).
Phillips et al., "Targeting HER2-Positive Breast Cancer with Trastuzumab-DM1, an Antibody-Cytotoxic Drug Conjugate," (2008) Cancer Res. 68(22):9280-9290.
Pingault V., et al., "SOX10 mutations in chronic intestinal pseudo-obstruction suggest a complex physiopathological mechanism," (2002) Hum. Genet. 111, 198-206.
Pletnev S., et al., "Characterization of the Recombinant Extracellular Domains of Human Interleukin-20 Receptors and Their Complexe with Interleukin-19 and Interleukin-20," (2003) Biochemistry 42:12617-12624.
Porkaa et al., "Cloning and Characterization of a Novel Six-Transmembrane Protein STEAP2, Expressed in Normal and Malignant Prostate," Lab. Invest. 82 (11):1573-1582 (2002).
Prasad et al.,"Human LAT1, a Subunit of System L Amino Acid Transporter: Molecular Cloning and Transport Function," Biochem. Biophys. Res. Commun. 255 (2), 283-288 (1999).
Preud'homme et al., "Structure and expression of the mb-1 transcript in human lymphoid cells," (1992) Clin. Exp. lmmunol. 90(1):141-146.

Puffenberger E.G., et al., "A Missense Mutation of the Endothelin-B Receptor Gene in Multigenic Hirschsprung's Disease," Cell 79, 1257-1266, 1994.
Rao et al., "Influence of diet on mammary cancer in transgenic mice bearing an oncogene expressed in mammary tissue," (1997) Breast Cancer Res. and Treatment 45:149-158.
Reiter R.E., et al., "Prostate stem cell antigen: A cell surface marker overexpressed in prostate cancer," Proc. Natl. Acad. Sci. U.S.A. 95, 1735-1740, 1998.
Rodrigues et al., "Synthesis and beta-lactamase-mediated activation of a cephalosporin-taxol prodrug," (1995) Chemistry Biology 2:223-227.
Ross et al., "Prostate Stem Cell Antigen as Therapy Target: Tissue Expression and in Vivo Efficacy of an Immunoconjugate," (2002) Cancer Res. 62:2546-2553.
Sakaguchi et al., "8 lymphocyte lineage-restricted expression of mb-1, a gene with CD3-Iike structural properties," (1988) EMBO J. 7(11):3457-3464.
Sakamoto A, Yanagisawa M., et al., "Cloning and Functional Expression of Human cDNA for the ETB Endothelin Receptor," Biochem. Biophys. Res. Commun. 178, 656-663, 1991.
Sanderson et al., "In vivo Drug-Linker Stability of an Anti-CD30 Dipeptide-Linked Auristatin Immunoconjugate," (2005) Clin. Cancer Res. 11:843-852.
Scholler et al., "Soluble member(s) of the mesothelin/ megakaryocyte potentiating factor family are detectable in sera from patients with ovarian carcinoma," Proc. Natl. Acad. Sci. USA vol. 96, pp. 11531-11536, Sep. 1999.
Schroder and Lubke, The Peptides, vol. 1. pp. 76-136 (1965) Academic Press.
Segawa et al., "Growth-related Renal Type II Na/Pi Cotransporter," The Journal of Biolocjcal Chemistry, vol. 277. No. 22, Issue of May 31, pp. 19665-19672, 2002.
Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A 82, 6497-6501, 1985.
Servenius et al., "Class II Genes of the Human Major Histocompatibility Complex, The DOBeta Gene is a Divergent Member of the Class II P Gene Family," (1987) J. Biol. Chem. 262:8759-8766.
Shamis et al., "Bioactivation of Self-lmmolative Dendritic Prodrugs by Catalytic Antibody 38C2," (2004) J . Am. Chem. Soc. 126:1726-1731.
Sheikh F., et al., "Cutting Edge: IL-26 Signals through a Novel Receptor Complex Composed of IL-20 Receptor 1 and IL-10 Receptor 21," (2004) J.Immunol, 172, 2006-2010.
Shen et al., "Conjugation site modulates the in vivo stability and therapeutic activity of antibody-drug conjugates," (2012) Nature Biotech., 30(2):184-191.
Sinha S.K., et al., "Characterization of the EBV /C3d Receptor on the Human Jurkat T Cell Line: Evidence for a Novel Transcript," (1993) J.lmmunol. 150, 5311-5320.
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse eDNA sequences," (2002) Proc. Natl. Acad. Sci USA 99:16899-16903.
Sun et al., "Enabling ScFvs as Multi-Drug Carriers: A Dendritic Approach," (2003) Bioorganic & Medicinal Chemistry 11:1761-1768.
Sun et al., "Syntheses of Dendritic Linkers Containing Chlorambucil Residues for the Preparation of Antibody-Multidrug Immunoconjugates," (2002) Bioorganic & Medicinal Chemistry Letters 12:2213-2215.
Svensson P.J., et al., "Phenotypic variation in a family with mutations in two Hirschsprung-related genes (RET and endothelin receptor B)," Hum. Genet. 103, 145-148, 1998.
Swiercz J.M., et al., "Plexin-81 /RhoGEF-mediated Rho A activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.

(56) References Cited

OTHER PUBLICATIONS

Takeuchi, et al., "Neothramycins A and B, New Antitumor Antibiotics.," J. Antibiotics, 29, 93-96 (1976).
Tawaragi Y., et al., "Primary Structure of Nonspecific Crossreacting Antigen (NCA), A Member of Carcinoembryonic Antigen (CEA) Gene Family, Deduced From cDNA Sequence," Biochem. Biophys. Res. Commun. 150, 89-96, 1988.
Thompson, J.S., et al., "BAFF-R, a Newly Identified TNF Receptor That Specifically Interacts with BAFF," Science 293 (5537), 2108-2111 (2001).
Thurston, et al., "The molecular recognition of DNA," Chem. Brit., 26, 767-772 (1990).
Thurston, et at., "Synthesis of DNA-Interactive Pyrrolo[2,1-c][1,4]benzodlazepines," Chem. Rev. 1994, 433-465 (1994).
Toki et al., "Protease-Mediated Fragmentation of p-Amidobenzyl Ethers: A New Strategy for the Activation of Anticancer Prodrugs,"(2002) J. Org. Chem. 67:1866-1872.
Tonnelle et al., "DOBeta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Segment and Discovery of a Novel Gene within the Common Cystinosis-Causing Deletion," (2000) Genome Res. 10:165-173.
Trail et al., "Monoclonal antibody drug immunoconjugates for targeted treatment of cancer," (2003) Cancer lmmunol. Immunother. 52:328-337.
Tsunakawa, et al., "Porothramycin, A New Antibiotic of the Anthramyclin Group: Production, Isolation, Structure and Biological Activity," J. Antibiotics, 41, 1366-1373 (1988).
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
United States Patent Office Action for U.S. Appl. No. 13/650,277 dated Mar. 3, 2014 (12 pages).
Verheij J.B., et al., "ABCD Syndrome is Caused by a Homozygous Mutation in the EDNRB Gene," Am. J. Med. 15 Genet. 108, 223-225, 2002.
Von Hoegen et al., "Identifigation of a Human Protein Homologous to the Mouse Lyb-2 B Cell Differentiation Antigen and Sequence of the Corresponding cDNA," (1990) J. lmmunol. 144(12):4870-4877.
Webster et al., "Mammary tumorigenesis and metastasis in transgenic mice," (1994) Semin. Cancer Biol. 5:69-76.
Weis J.J., et al., "Identification of a partial eDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.
Weis J.J., et al., "Structure of the Human B Lymphocyte Receptor for C3d and the Epstein-Barr Virus and Relatedness to Other Members of the Family of C3/C4 Binding Proteins," J. Exp. Med. 167, 1047-1066, 1988.
Wilkinson, "Eph Receptors and Ephrins: Regulators of Guidance and Assembly," Int. Rev. Cytol. 196:177-244 (2000).
Wilson et al., "eDNA Cloning of the B Cell Membrane Protein CD22: A Mediator of B—B Cell Interactions," (1991) J. Exp. Med. 173:137-146.
Wu et al., "Arming antibodies: prospects and challenges for immunoconjugates," (2005) Nature Biotech. 23(9):1137-1145.
Xie et al., "In vivo behaviour of antibody-drug conjugates for the targeted treatment of cancer," (2006) Expert. Opin Biol. Ther. 6(3):281-291.
Xu et al., "Molecular Cloning, Functional Characterization, Tissue Distribution, and Chromosomal Localization of a Human, Small Intestinal Sodium-Phosphate (Na + -Pi) Transporter (SLC34A2)," Genomics 62 (2):281-284 (1999).
Xu, M.J., et al., "Molecular Cloning and Characterization of SPAP1, an Inhibitory Receptor," (2001) Biochem. Biophys. Res. Commun. 280 (3):768-775.
Xu, X.Z., et al., "Regulation of melastatin, a TRP-related protein, through interaction with a cytoplasmic isoform," Proc. Natl. Acad. Sci. U.S.A. 98 (19):10692-10697 (2001).
Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).
Yamamoto T., et al., "Similarity of protein encoded by the human c-erb-B-2 gene to epidermal growth factor receptor," Nature 319, 230-234, 1986.
Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.
Yin & Lloyd, "Molecular Cloning of the CA125 Ovarian Cancer Antigen," J. Biol. Chem. 276 (29):27371-27375 (2001).
Yu et al., "Human mb-1 Gene: Complete eDNA Sequence and its Expression in B Cells Bearing Membrane Ig of Various Isotypes," (1992) J. lmmunol. 148(2) 633-637.

* cited by examiner

PYRROLOBENZODIAZEPINES AND CONJUGATES THEREOF

This application claims priority to U.S. Provisional Patent Application No. 61/547,187 filed Oct. 14, 2011, which is incorporated herein by reference in its entirety.

INCORPORATION OF SEQUENCE LISTING

The instant application contains a Sequence Listing which has been submitted in ASCII format via EFS-Web and is hereby incorporated by reference in its entirety. Said ASCII copy, created on Jun. 6, 2013, is named ASFILED_SequenceListing-Text.txt and is 661 bytes in size.

BACKGROUND TO THE INVENTION

The present invention relates to pyrrolobenzodiazepines (PBDs), in particular pyrrolobenzodiazepines having a labile N10 protecting group, in the form of a linker to a cell binding agent.

Pyrrolobenzodiazepines

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994); Antonow, D. and Thurston, D. E., *Chem. Rev.* 2011 111 (4), 2815-2864). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)); neothramycins A and B (Takeuchi, et al., *J. Antibiotics*. 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102) (Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

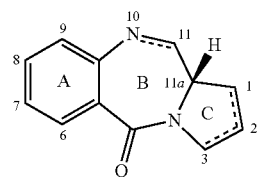

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

The present inventors have previously disclosed in WO 2005/085251, dimeric PBD compounds bearing C2 aryl substituents, such as:

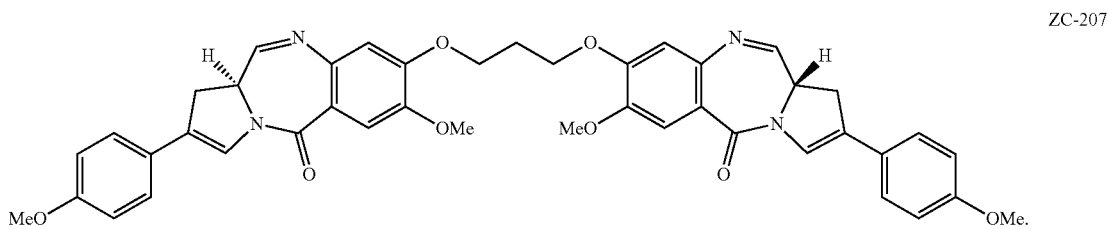 [SMILES: COc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

ZC-207

These compounds have been shown to be highly useful cytotoxic agents.

A particularly advantageous pyrrolobenzodiazepine compound is described by Gregson at al. (*Chem. Commun.* 1999, 797-798) as compound 1, and by Gregson et al. (*J. Med. Chem.* 2001, 44, 1161-1174) as compound 4a. This compound, also known as SJG-136, is shown below:

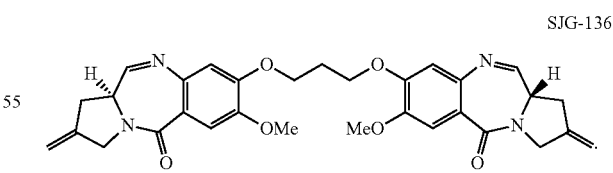

SJG-136

The present inventors have previously disclosed that PBD compounds can be employed as prodrugs by protecting them at the N10 position with a nitrogen protecting group which is removable in vivo (WO 00/12507). Many of these protecting groups are carbamates, and are, for example, of the structure:

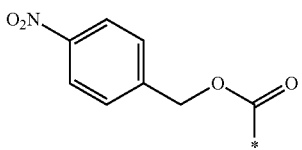 [SMILES: *C(=O)OCc1ccc([N+](=O)[O-])cc1]

where the asterisk (*) indicates the attachment point to the N10 atom of the PBD.

The present inventors have also described the preparation of PBD compounds having a nitrogen carbamate protecting group at the N10 position (WO 2005/023814). The protecting groups are removable from the N10 position of the PBD moiety to leave an N10-C11 imine bond. A range of protecting groups is described, including groups that can be cleaved by the action of enzymes.

WO 2007/085930 describes the preparation of dimer PBD compounds having linker groups for connection to a cell binding agent, such as an antibody. The linker is present in the bridge linking the monomer PBD units of the dimer.

Antibody-Drug Conjugates

Antibody therapy has been established for the targeted treatment of patients with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells as well as the tumor cells sought to be eliminated (Xie et al (2006) Expert. Opin. Biol. Ther. 6(3):281-291; Kovtun et al (2006) Cancer Res. 66(6):3214-3121; Law et al (2006) Cancer Res. 66(4):2328-2337; Wu et al (2005) Nature Biotech 23(9):1137-1145; Lambert J. (2005) Current Opin. in Pharmacol 5:543-549; Hamann P. (2005) Expert Opin. Ther. Patents 15(9):1087-1103; Payne, G. (2003) Cancer Cell 3:207-212; Trail et al (2003) Cancer Immunol. Immunother. 52:328-337; Syrigos and Epenetos (1999) Anticancer Research 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Junutula, et al., 2008b Nature Biotech., 26(8):925-932; Doman eta) (2009) Blood 114(13):2721-2729; U.S. Pat. Nos. 7,521,541; 7,723,485; WO2009/052249; McDonagh (2006) Protein Eng. Design & Sel. 19(7): 299-307; Doronina et al (2006) Bioconj. Chem. 17:114-124; Erickson et al (2006) Cancer Res. 66(8):1-8; Sanderson et al (2005) Clin. Cancer Res. 11:843-852; Jeffrey et al (2005) J. Med. Chem. 48; 1344-1358; Hamblett et al (2004) Clin. Cancer Res. 10:7063-7070). Drug moieties may impart their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

The present inventors have developed a novel approach to forming PBD conjugates with cell binding agents, and in particular PBD antibody conjugates.

SUMMARY OF THE INVENTION

In a general aspect the present invention provides a conjugate comprising a PBD dimer compound connected through the N10 position via a specific sulfur linker to a cell binding agent. The cell binding agent is preferably an antibody.

In a first aspect, the present invention provides novel conjugate compounds of formula (A):

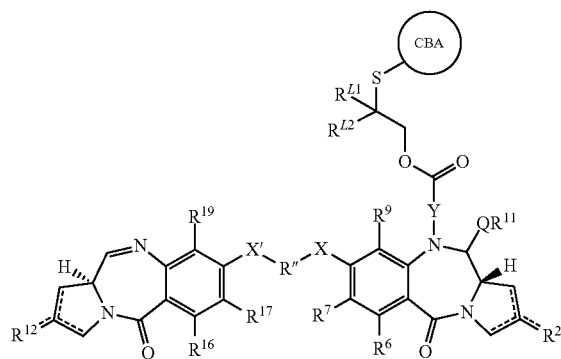

and salts and solvates thereof, wherein:
the dotted lines indicate the optional presence of a double bond between C1 and C2 or C2 and C3;
$R^2$ is independently selected from H, OH, =O, =CH$_2$, CN, R, OR, =CH—$R^D$, =C($R^D$)$_2$, O—SO$_2$—R, CO$_2$R and COR, and optionally further selected from halo or dihalo;
where $R^D$ is independently selected from R, CO$_2$R, COR, CHO, CO$_2$H, and halo;
$R^6$ and $R^9$ are independently selected from H, R, OH, OR, SH, SR, NH$_2$, NHR, NRR', NO$_2$, Me$_3$Sn and halo;
$R^7$ is independently selected from H, R, OH, OR, SH, SR, NH$_2$, NHR, NRR', NO$_2$, Me$_3$Sn and halo;
Y is selected from a single bond, and a group of formulae A1 or A2:

(A1)

(A2)

where N shows where the group binds to the N10 of the PBD moiety;
$R^{L1}$ and $R^{L2}$ are independently selected from H and methyl, or together with the carbon atom to which they are bound form a cyclopropylene group;
CBA represents a cell binding agent;
Q is independently selected from O, S and NH;
$R^{11}$ is either H, or R or, where Q is O, SO$_3$M, where M is a metal cation;
R and R' are each independently selected from optionally substituted C$_{1-12}$ alkyl, C$_{3-20}$ heterocyclyl and C$_{5-20}$ aryl groups, and optionally in relation to the group NRR', R and R' together with the nitrogen atom to which they are attached form an optionally substituted 4-, 5-, 6- or 7-membered heterocyclic ring;
wherein $R^{12}$, $R^{16}$, $R^{19}$ and $R^{17}$ are as defined for $R^2$, $R^6$, $R^9$ and $R^7$ respectively;
wherein R" is a C$_{3-12}$ alkylene group, which chain may be interrupted by one or more heteroatoms, e.g. O, S, N(H), NMe and/or aromatic rings, e.g. benzene or pyridine, which rings are optionally substituted;
X and X' are independently selected from O, S and N(H).
Thus formula A is selected from the following formulae A-I, A-II and A-III, depending on Y:

| Y | A |
|---|---|
| Single bond | 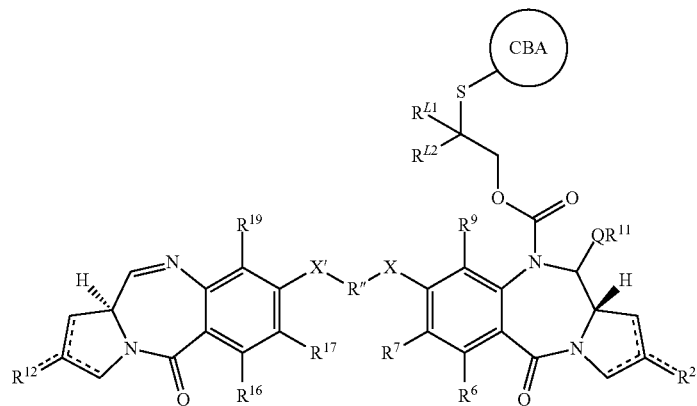<br>A-I |
| 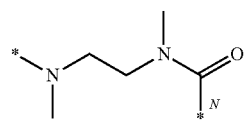<br>(A1) | 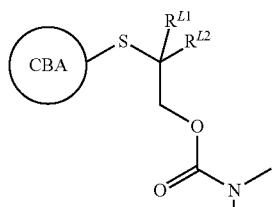<br>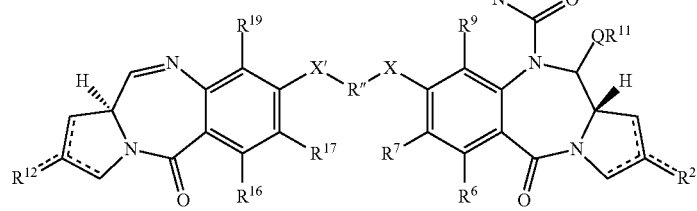<br>A-II |
| 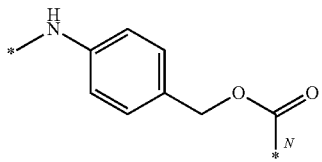<br>(A2) | 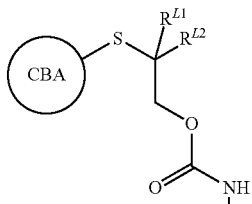<br>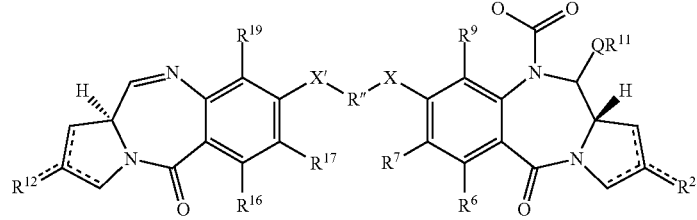<br>A-III |

In compounds of formula A:

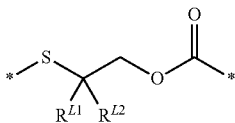

is the sulfur linking group.

A second aspect of the present invention pertains to the use of a conjugate of the first aspect to provide a compound of formula (B) or (C) at a target location:

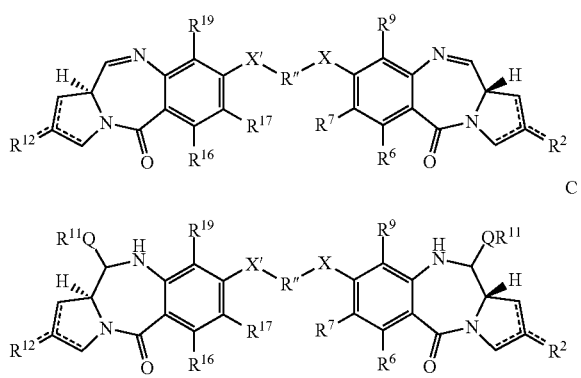

and salts and solvates thereof, wherein the groups are as for the first aspect, except that Q is independently selected from O, S and NH; and $R^{11}$ is either H, or R or, where Q is O, $SO_3M$, where M is a metal cation.

A third aspect of the present invention also provides compounds of formula (D) for use in the preparation of the conjugate compounds of the invention:

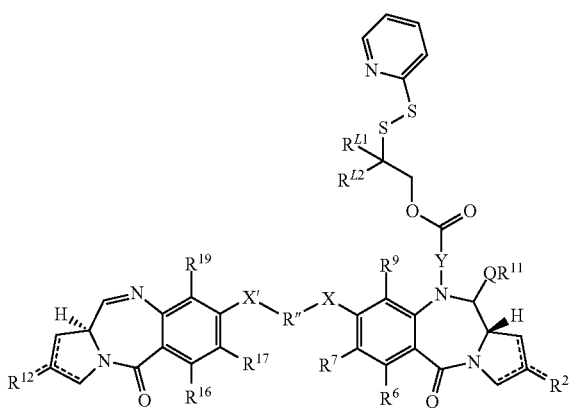

and salts and solvates thereof, wherein the groups are as defined in the first aspect of the invention.

In the compounds above, the 5-membered rings represented by

may be replaced by a ring selected from:

(a)

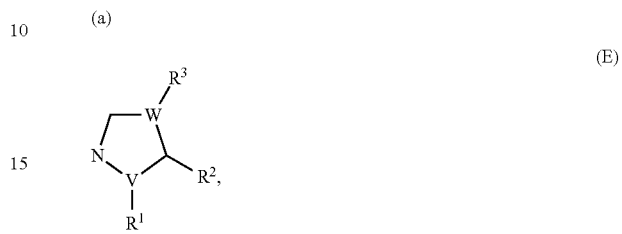

where $R^2$ with either of $R^1$ or $R^3$, together with the carbon atoms of the C ring to which they are attached, form an optionally substituted benzene ring;

V and W are each selected from $(CH_2)_n$, O, S, NR, CHR, and CRR' where n is 1, 2 or 3, except that V is C when $R^1$ and $R^2$, together with the carbon atoms of the C ring to which they are attached, form an optionally substituted benzene ring, and W is C when $R^3$ and $R^2$, together with the carbon atoms of the C ring to which they are attached, form an optionally substituted benzene ring; and (b)

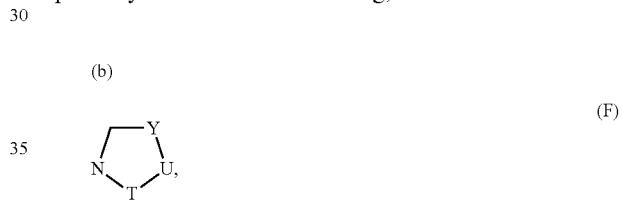

where T is selected from $CH_2$, NR, CO, BH, SO, and $SO_2$;

U is selected from $CH_2$, NR, O and S;

Y is $(CH_2)_n$, where n is 1, 2, 3 or 4;

except that T, U and Y are not all $CH_2$.

DETAILED DESCRIPTION OF THE INVENTION

The resent invention provides a conjugate comprising a PBD dimer connected through the N10 position on one of the PBD moieties via the specified linker to a cell binding agent.

The present invention is suitable for use in providing a PBD compound to a preferred site in a subject. The conjugate allows the release of an active PBD compound that does not retain any part of the linker. There is no stub present that could affect the reactivity of the PBD compound.

Preferences

The following preferences may apply to all aspects of the invention as described above, or may relate to a single aspect. The preferences may be combined together in any combination.

Double Bond

In one embodiment, there is no double bond present between C1 and C2, and C2 and C3.

In one embodiment, the dotted lines indicate the optional presence of a double bond between C2 and C3, as shown below:

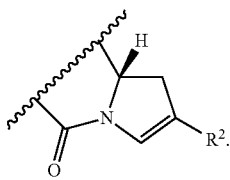

In one embodiment, a double bond is present between C2 and C3 when $R^2$ is $C_{5-20}$ aryl or $C_{1-12}$ alkyl.

In one embodiment, the dotted lines indicate the optional presence of a double bond between C1 and C2, as shown below:

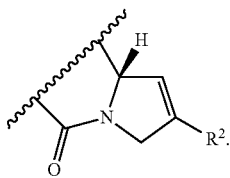

In one embodiment, a double bond is present between C1 and C2 when $R^2$ is $C_{5-20}$ aryl or $C_{1-12}$ alkyl.

$R^2$

In one embodiment, $R^2$ is independently selected from H, OH, =O, =CH$_2$, CN, R, OR, =CH—$R^D$, =C($R^D$)$_2$, O—SO$_2$—R, CO$_2$R and COR, and optionally further selected from halo or dihalo.

In one embodiment, $R^2$ is independently selected from H, OH, =O, =CH$_2$, CN, R, OR, =CH—$R^D$, =C($R^D$)$_2$, O—SO$_2$—R, CO$_2$R and COR.

In one embodiment, $R^2$ is independently selected from H, =O, =CH$_2$, R, =CH—$R^D$, and =C($R^D$)$_2$.

In one embodiment, $R^2$ is independently H.

In one embodiment, $R^2$ is independently =O.

In one embodiment, $R^2$ is independently =CH$_2$.

In one embodiment, $R^2$ is independently =CH—$R^D$. Within the PBD compound, the group =CH—$R^D$ may have either configuration shown below:

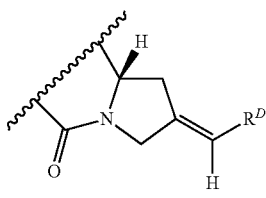
(I)

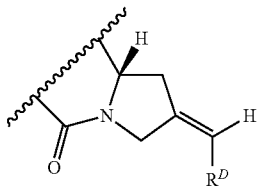
(II)

In one embodiment, the configuration is configuration (I).

In one embodiment, $R^2$ is independently =C($R^D$)$_2$.

In one embodiment, $R^2$ is independently =CF$_2$.

In one embodiment, $R^2$ is independently R.

In one embodiment, $R^2$ is independently optionally substituted $C_{5-20}$ aryl.

In one embodiment, $R^2$ is independently optionally substituted $C_{1-12}$ alkyl.

In one embodiment, $R^2$ is independently optionally substituted $C_{5-20}$ aryl.

In one embodiment, $R^2$ is independently optionally substituted $C_{5-7}$ aryl.

In one embodiment, $R^2$ is independently optionally substituted $C_{8-10}$ aryl.

In one embodiment, $R^2$ is independently optionally substituted phenyl.

In one embodiment, $R^2$ is independently optionally substituted thienyl.

In one embodiment, $R^2$ is independently optionally substituted napthyl.

In one embodiment, $R^2$ is independently optionally substituted pyridyl.

In one embodiment, $R^2$ is independently optionally substituted quinolinyl or isoquinolinyl.

In one embodiment, $R^2$ bears one to three substituent groups, with 1 and 2 being more preferred, and singly substituted groups being most preferred. The substituents may be any position.

Where $R^2$ is a $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

In one embodiment, $R^2$ is selected from:

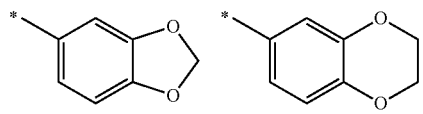

where the asterisk indicates the point of attachment.

Where $R^2$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

In one embodiment, where $R^2$ is optionally substituted, the substituents are selected from those substituents given in the substituent section below.

Where R is optionally substituted, the substituents are preferably selected from:

Halo, Hydroxyl, Ether, Formyl, Acyl, Carboxy, Ester, Acyloxy, Amino, Amido, Acylamido, Aminocarbonyloxy, Ureido, Nitro, Cyano and Thioether.

In one embodiment, where R or $R^2$ is optionally substituted, the substituents are selected from the group consisting of R, OR, SR, NRR', NO$_2$, halo, CO$_2$R, COR, CONH$_2$, CONHR, and CONRR'.

Where $R^2$ is $C_{1-12}$ alkyl, the optional substituent may additionally include $C_{3-20}$ heterocyclyl and $C_{5-20}$ aryl groups.

Where $R^2$ is $C_{3-20}$ heterocyclyl, the optional substituent may additionally include $C_{1-12}$ alkyl and $C_{5-20}$ aryl groups.

Where $R^2$ is aryl groups, the optional substituent may additionally include $C_{5-20}$ heterocyclyl and $C_{1-12}$ alkyl groups.

It is understood that the term "alkyl" encompasses the sub-classes alkenyl and alkynyl as well as cycloalkyl. Thus, where $R^2$ is optionally substituted $C_{1-12}$ alkyl, it is understood that the alkyl group optionally contains one or more carbon-carbon double or triple bonds, which may form part of a conjugated system. In one embodiment, the optionally substituted $C_{1-12}$ alkyl group contains at least one carbon-carbon double or triple bond, and this bond is conjugated with a double bond present between C1 and C2, or C2 and C3. In one embodiment, the $C_{1-12}$ alkyl group is a group selected from saturated $C_{1-12}$ alkyl, $C_{2-12}$ alkenyl, $C_{2-122}$ alkynyl and $C_{3-12}$ cycloalkyl.

If a substituent on $R^2$ is halo, it is preferably F or Cl, more preferably F.

If a substituent on $R^2$ is ether, it may in some embodiments be an alkoxy group, for example, a $C_{1-7}$ alkoxy group (e.g. methoxy, ethoxy) or it may in some embodiments be a $C_{5-7}$ aryloxy group (e.g phenoxy, pyridyloxy, furanyloxy).

If a substituent on $R^2$ is $C_{1-7}$ alkyl, it may preferably be a $C_{1-4}$ alkyl group (e.g. methyl, ethyl, propyl, butyl).

If a substituent on $R^2$ is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups.

If a substituent on $R^2$ is bis-oxy-$C_{1-3}$ alkylene, this is preferably bis-oxy-methylene or bis-oxy-ethylene.

Particularly preferred substituents for $R^2$ include methoxy, ethoxy, fluoro, chloro, cyano, bis-oxy-methylene, methyl-piperazinyl, morpholino and methyl-thienyl.

Particularly preferred substituted $R^2$ groups include, but are not limited to, 4-methoxy-phenyl, 3-methoxyphenyl, 4-ethoxy-phenyl, 3-ethoxy-phenyl, 4-methyl-phenyl, 4-fluoro-phenyl, 4-chloro-phenyl, 3,4-bisoxymethylene-phenyl, 4-methylthienyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl.

In one embodiment, $R^2$ is halo or dihalo. In one embodiment, $R^2$ is —F or —$F_2$, which substituents are illustrated below as (III) and (IV) respectively:

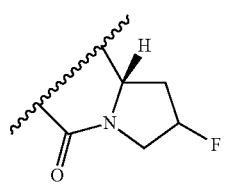
(III)

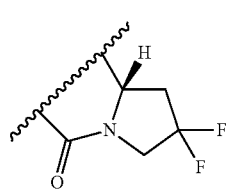
(IV)

In some embodiments, it is preferred that there is either a double bond between C2 and C3 or the C2 substituent is bound to the PBD ring by a double bond (i.e. that the C atom at C2 is a sp$^2$ centre)

$R^D$

In one embodiment, $R^D$ is independently selected from R, $CO_2R$, COR, CHO, $CO_2H$, and halo.

In one embodiment, $R^D$ is independently R.

In one embodiment, $R^D$ is independently halo.

$R^6$

In one embodiment, $R^6$ is independently selected from H, R, OH, OR, SH, SR, $NH_2$, NHR, NRR', $NO_2$, $Me_3Sn$— and Halo.

In one embodiment, $R^6$ is independently selected from H, OH, OR, SH, $NH_2$, $NO_2$ and Halo.

In one embodiment, $R^6$ is independently selected from H and Halo.

In one embodiment, $R^6$ is independently H.

In one embodiment, $R^6$ and $R^7$ together form a group —O—$(CH_2)_p$—O—, where p is 1 or 2.

$R^7$ $R^7$ is independently selected from H, R, OH, OR, SH, SR, $NH_2$, NHR, NRR', $NO_2$, $Me_3Sn$ and halo.

In one embodiment, $R^7$ is independently OR.

In one embodiment, $R^7$ is independently $OR^{7A}$, where $R^{7A}$ is independently optionally substituted $C_{1-6}$ alkyl.

In one embodiment, $R^{7A}$ is independently optionally substituted saturated $C_{1-6}$ alkyl.

In one embodiment, $R^{7A}$ is independently optionally substituted $C_{2-4}$ alkenyl.

In one embodiment, $R^{7A}$ is independently Me.

In one embodiment, $R^{7A}$ is independently $CH_2Ph$.

In one embodiment, $R^{7A}$ is independently allyl.

$R^9$

In one embodiment, $R^9$ is independently selected from H, R, OH, OR, SH, SR, $NH_2$, NHR, NRR', $NO_2$, $Me_3Sn$— and Halo.

In one embodiment, $R^9$ is independently H.

In one embodiment, $R^9$ is independently R or OR.

Linking Group

The linking group is removable from the N10 position of the PBD moiety in the conjugate of formula A to leave an N10-C11 imine bond, a carbinolamine, a substituted carbinolamine, where $QR^{11}$ is $OSO_3M$, a bisulfite adduct, a thiocarbinolamine, a substituted thiocarbinolamine, or a substituted carbinalamine (compound of formulae B or C) as illustrated below:

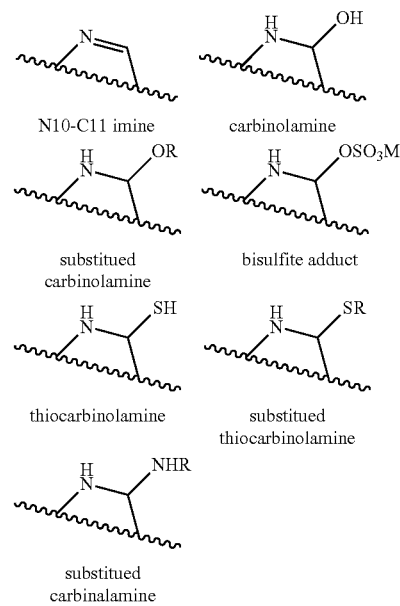

where R and M are as defined for the conjugates of the invention.

In one embodiment, the linking group is removable from the N10 position of the PBD moiety to leave an N10-C11 imine bond.

The specified link between the PBD dimer and the cell binding agent, e.g. antibody, in the present invention is preferably stable extracellularly. Before transport or delivery into a cell, the antibody-drug conjugate (ADC) is preferably stable and remains intact i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS.

Delivery of the compounds of formulae B or C is achieved at the desited activation site of the conjugates of formula A by the action of an enzyme on the linking group. The S of the conjugate of formula A is linked by a disulfide bond to a free S (active thiol) on the cell binding agent.

The linking group may be cleavable by the action of an enzyme. In one embodiment, the enzyme is a thioreductase.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

$R^{L1}$ and $R^{L2}$ are selected from H and methyl, or together with the carbon atom to which they are bound form a cyclopropylene group. In some embodiments, both are H. In other embodiment, both are methyl. In further embodiments, one is H and the other is methyl; in these embodiments, the carbon atom to which they are bound is a chiral centre.

In some embodiments, Y is a single bond.

In rather embodiments, Y is

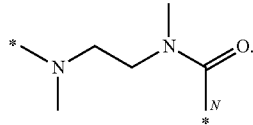

(A1)

In further embodiments, Y is

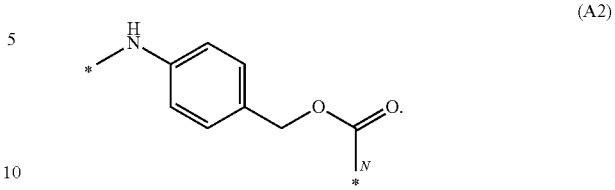

(A2)

Q

In one embodiment, Q is selected from O, S, or N(H).
Preferably, Q is O.
$R^{11}$ In one embodiment, $R^{11}$ is either H, or R or, where Q is O, $SO_3M$, where M is a metal cation.

In one embodiment, $R^{11}$ is H.

In one embodiment, $R^{11}$ is R.

In one embodiment, where Q is O, $R^{11}$ is $SO_3M$, where M is a metal cation. The cation may be $Na^+$.

Cell Binding Agent

A cell binding agent may be of any kind, and include peptides and non-peptides. These can include antibodies or a fragment of an antibody that contains at least one binding site, lymphokines, hormones, growth factors, nutrient-transport molecules, or any other cell binding molecule or substance.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known.

Examples of cell binding agents include those agents described for use in WO 2007/085930, which is incorporated herein.

The cell binding agent may be, or comprise, a polypeptide. The polypeptide may be a cyclic polypeptide. The cell binding agent may be antibody. Thus, in one embodiment, the present invention provides an antibody-drug conjugate (ADC).

Drug Loading

The drug loading is the average number of PBD drugs per antibody. Drug loading may range from 1 to 8 drugs (D) per antibody (Ab), i.e. where 1, 2, 3, 4, 5, 6, 7, and 8 drug moieties are covalently attached to the antibody. Compositions of ADC include collections of antibodies conjugated with a range of drugs, from 1 to 8. The average number of drugs per antibody in preparations of ADC from conjugation reactions may be characterized by conventional means such as mass spectroscopy, ELISA assay, electrophoresis, and HPLC. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limiting reductive conditions for cysteine thiol modification.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. Nos. 7,521,541; 7,723,485; WO2009/052249, Shen et al (2012) Nature Biotech., 30(2): 184-191; Junutula et al (2008) Jour of Immun. Methods 332.41-52). The engineered cysteine thiols may react with linker reagents or the drug-linker reagents, of the present invention which have thiol-reactive, electrophilic groups such as maleimide or alpha-halo amides to form ADC with cysteine engineered antibodies (ThioMabs) and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved and near homogeneity of the conjugation product ADC.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per cell binding agent is in the range 1 to 20. In some embodiments the range is selected from 1 to 8, 2 to 8, 2 to 6, 2 to 4, and 4 to 8.

In some embodiments, there is one dimer pyrrolobenzodiazepine groups per cell binding agent.

Peptides

In one embodiment, the cell binding agent is a linear or cyclic peptide comprising 4-20, preferably 6-20, contiguous amino acid residues. In this embodiment, it is preferred that one cell binding agent is linked to one monomer or dimer pyrrolobenzodiazepine compound.

In one embodiment the cell binding agent comprises a peptide that binds integrin $\alpha_v\beta_6$. The peptide may be selective for $\alpha_v\beta_6$ over XYS.

In one embodiment the cell binding agent comprises the A20FMDV-Cys polypeptide. The A20FMDV-Cys has the sequence: NAVPNLRGDLQVLAQKVARTC. Alternatively, a variant of the A20FMDV-Cys sequence may be used wherein one, two, three, four, five, six, seven, eight, nine or ten amino acid residues is substituted with another amino acid residue.

In one embodiment the antibody is a monoclonal antibody; chimeric antibody; humanized antibody; fully human antibody; or a single chain antibody. One embodiment the antibody is a fragment of one of these antibodies having biological activity. Examples of such fragments include Fab, Fab', F(ab')$_2$ and Fv fragments.

In these embodiments, each antibody may be linked to one or several dimer pyrrolobenzodiazepine groups. The preferred ratios of pyrrolobenzodiazepine to cell binding agent are given above.

The antibody may be a domain antibody (DAB).

In one embodiment, the antibody is a monoclonal antibody.

Antibodies for use in the present invention include those antibodies described in WO 2005/082023 which is incorporated herein. Particularly preferred are those antibodies for tumour-associated antigens. Examples of those antigens known in the art include, but are not limited to, those tumour-associated antigens set out in WO 2005/082023. See, for instance, pages 41-55.

The conjugates of the invention are designed to target tumour cells via their cell surface antigens. The antigens are usually normal cell surface antigens which are either overexpressed or expressed at abnormal times. Ideally the target antigen is expressed only on proliferative cells (preferably tumour cells), however this is rarely observed in practice. As a result, target antigens are usually selected on the basis of differential expression between proliferative and healthy tissue.

Antibodies have been raised to target specific tumour related antigens including:

Cripto, CD30, CD19, CD33, Glycoprotein NMB, CanAg, Her2 (ErbB2/Neu), CD56 (NCAM), CD22 (Siglec2), CD33 (Siglec3), CD r'9, CD138, PSCA, PSMA (prostate specific membrane antigen), BCMA, CD20, CD70, E-selectin, EphB2, Melanotransferin, Muc16 and TMEFF2.

Tumor-associated antigens (TAA) are known in the art, and can prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, TAA (1)-(36) listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI), Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Tumor-Associated Antigens (1)-(36):

(1) BMPR1B (bone morphogenetic protein receptor-type IB, Genbank accession no. NM_001203) ten Dijke, P., et al *Science* 264 (5155):101-104 (1994), *Oncogene* 14 (11): 1377-1382 (1997)); WO2004/063362 (Claim 2); WO2003/042661 (Claim 12); US2003/134790-A1 (Page 38-39); WO2002/102235 (Claim 13; Page 296); WO2003/055443 (Page 91-92); WO2002/99122 (Example 2; Page 528-530); WO2003/029421 (Claim 6); WO2003/024392 (Claim 2; FIG. 112); WO2002/98358 (Claim 1; Page 183); WO2002/54940 (Page 100-101); WO2002/59377 (Page 349-350); WO2002/30268 (Claim 27; Page 376); WO2001/48204 (Example; FIG. 4); NP_001194 bone morphogenetic protein receptor, type IB/pid=NP_001194.1. Cross-references: MIM:603248; NP_001194.1; AY065994

(2) E16 (LAT1, SLC7A5, Genbank accession no. NM_003486) *Biochem. Biophys. Res. Commun.* 255 (2), 283-288 (1999), *Nature* 395 (6699):288-291 (1998), Gaugitsch, K W., et al (1992) *J. Biol. Chem.* 267 (16):11267-11273); WO2004/048938 (Example 2), WO2004/032842 (Example IV); WO2003/042661 (Claim 12); WO2003/016475 (Claim 1); WO2002/78524 (Example 2); WO2002/99074 (Claim 19; Page 127-129); WO2002/86443 (Claim 27; Pages 222, 393); WO2003/003906 (Claim 10 Page 293); WO2002/64798 (Claim 33; Page 93-95); WO2000/14228 (Claim 5; Page 133-136); US2003/224454 (FIG. 3); WO2003/025138 (Claim 12; Page 150); NP_003477 solute carrier family 7 (cationic amino acid transporter, y+system), member 5/pid=NP_003477.3—*Homo sapiens*; Cross-references: MIM:600182; NP_0034773; NM_015923; NM_003486_1

Figure 2:
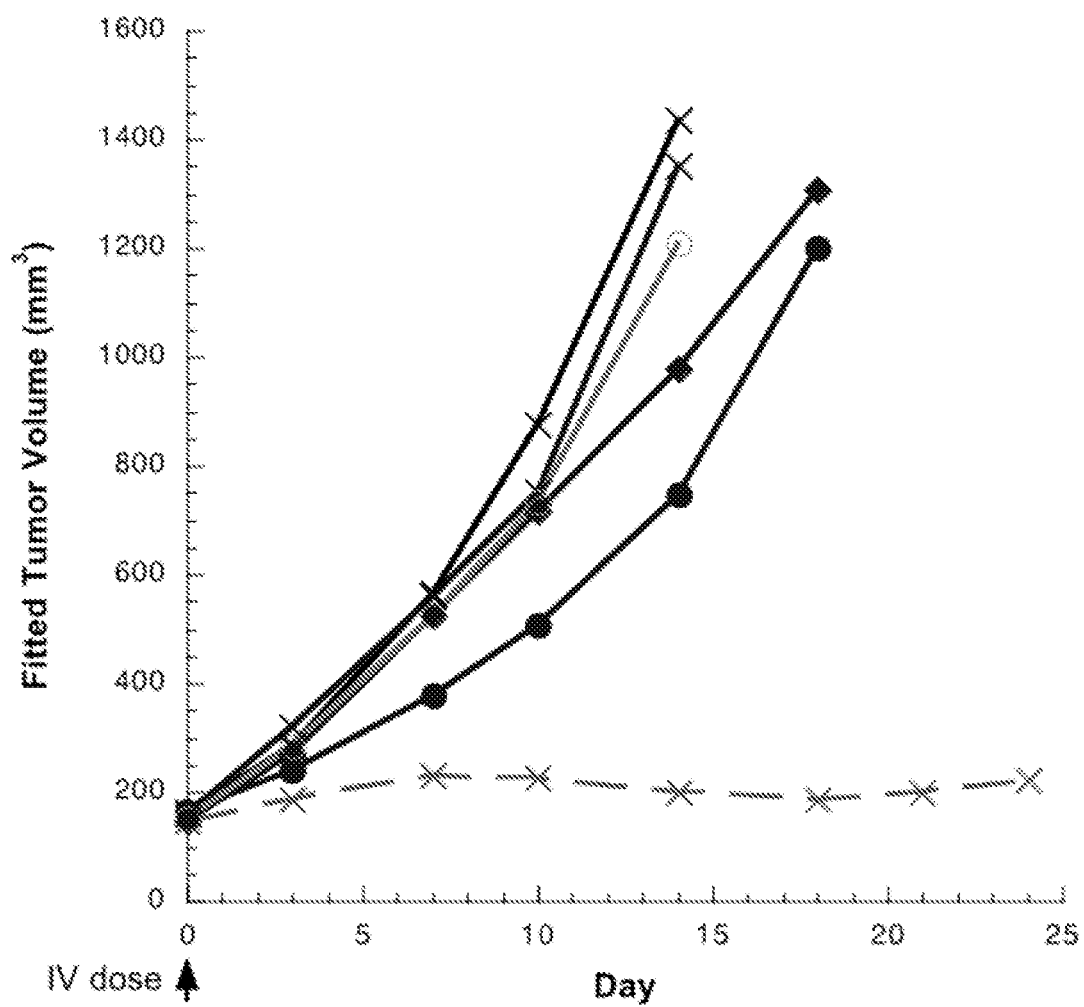

(3) STEAP1 (six transmembrane epithelial antigen of prostate, Genbank accession no. NM_012449); *Cancer Res.* 61 (15), 5857-5860 (2001), Hubert, R. S., et al (1999) *Proc. Natl. Acad. Sci. USA.* 96 (25):14523-14528); WO2004/065577 (Claim 6); WO2004/027049 (FIG. 1L); EP1394274 (Example 11); WO2004/016225 (Claim 2); WO2003/042661 (Claim 12); US2003/157089 (Example 5); US2003/185830 (Example 5); US2003/064397 (FIG. 2); WO2002/89747 (Example 5; Page 618-619); WO2003/022995 (Example 9; FIG. 13A, Example 53; Page 173, Example 2; FIG. 2A); NP_036581 six transmembrane epithelial antigen of the prostate; Cross-references: MIM:604415; NP_036581.1; NM_012449_1

(4) 0772P (CA125, MUC16, Genbank accession no. AF361486); *J. Biol. Chem.,* 276 (29):27371-27375 (2001)); WO2004/045553 (Claim 4); WO2002/92836 (Claim 6; FIG. 12); WO2002/83866 (Claim 15; Page 116-121); US2003/124140 (Example 16); Cross-references: GI:3.4501467; AAK74120.3; AF361486_1

(5) MPF (MPF, MSLN, SMR, megakaryocyte potentiating factor, mesothelin, Genbank accession no NM_005823) Yamaguchi, N., et al *Biol. Chem.* 269 (2), 805-808 (1994), *Proc. Natl. Aced. Sci. U.S.A.* 96 (20):11531-11536 (1999), *Proc. Natl. Aced. Sci. U.S.A.* 93 (1):136-140 (1996), *J. Biol. Chem.* 270 (37):21984-21990 (1995)); WO2003/101283 (Claim 14); (WO2002/102235 (Claim 13; Page 287-288); WO2002/101075 (Claim 4; Page 308-309); WO2002/71928 (Page 320-321); WO94/10312 (Page 52-57); Cross-references: MIM:601051; NP_005814.2; NM_005823_1

(6) Napi3b (NAPI-38, NPTIIb, SLC34A2, solute carrier family 34 (sodium phosphate), member 2, type II sodium-dependent phosphate transporter 3b, Genbank accession no. NM_006424) *J. Biol. Chem.,* 277 (22):19665-19672 (2002), *Genomics* 62 (2):281-284 (1999), Feild, J. A., et al (1999) *Biochem. Biophys. Res. Commun.* 258 (3):578-582); WO2004/022778 (Claim 2); EP1394274 (Example 11); WO2002/102235 (Claim 13; Page 326); EP0875569 (Claim 1; Page 17-19); WO2001/57188 (Claim 20; Page 329); WO2004/032842 (Example IV); WO2001/75177 (Claim 24; Page 139-140)); Cross-references: MIM:604217; NP_006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878); Nagase T., et al (2000) *DNA Res.* 7 (2):143-150); WO2004/000997 (Claim 1); WO2003/003984 (Claim 1); WO2002/06339 (Claim 1; Page 50); WO2001/88133 (Claim 1; Page 41-43, 48-58); WO2003/054152 (Claim 20); WO2003/101400 (Claim 11); Accession; Q9P283; EMBL; AB040878; BAA95969.1. Genew; HGNC:10737

(8) PSCA hlg (2700050C12Rik, C530008O16Rik, RIKEN cDNA 2700050C12, RIKEN cDNA 2700050C12 gene, Genbank accession no. AY358628), Ross et al (2002) *Cancer Res.* 62:2546-2553; US2003/129192 (Claim 2); US2004/044180 (Claim 12); US2004/044179 (Claim 11); US2003/096961 (Claim 11), US2003/232056 (Example 5); WO2003/105758 (Claim 12); US2003/206918 (Example 5); EP1347046 (Claim 1); WO2003/025148 (Claim 20); Cross-references: GI:37182373; AAQ88991.1; AY358628_1

(9) ETBR (Endothelin type B receptor, Genbank accession no. AY275463); Nakamuta M., et al *Biochem. Biophys. Res. Commun,* 177, 34-39, 1991; Ogawa Y., et al *Biochem. Biophys. Res. Commun.* 178, 248-255, 1991; Arai H. et al *Jpn. Circ. J.* 56, 1303-1307, 1992; Arai H., et al *J. Biol. Chem.* 268, 3463-3470, 1993; Sakamoto A., Yanagisawa M., et al *Biochem. Biophys. Res. Commun.* 178, 656-663, 1991; Elshourbagy N. A., et al *J. Biol. Chem.* 268, 3873-3879, 1993; Haendler B., et al *J. Cardiovasc. Pharmacol* 20, s1-S4, 1992; Tsutsumi M., et al *Gene* 228, 43-49, 1999; Strausberg R. L., et al *Proc. Natl. Acad. Sci. U.S.A.* 99, 16899-16903, 2002; Bourgeois C., et al *J. Clin. Endocrinol. Metab.* 82, 3116-3123, 1997; Okamoto Y., et al *Biol. Chem.* 272, 21589-21596, 1997; Verheij J. B., et al *Am. J. Med. Genet.* 108, 223-225, 2002; Hofstra R. M. W., et al *Eur. J. Hum. Genet.* 5, 180-185, 1997; Puffenberger E. G., et al *Cell* 79, 1257-1266, 1994; Attie T., et al, *Hum. Mol. Genet.* 4, 2407-2409, 1995; Auricchio A., et al *Hum. Mol. Genet,* 5:351-354, 1996; Amiel J., et al *Hum. Mol. Genet.* 5, 355-357, 1996; Hofstra R. M. W., et al *Nat. Genet.* 12, 445-447, 1996; Svensson P. J., et al *Hum. Genet.* 103, 145-143, 1993; Fuchs S., et al *Mol. Med.* 7, 115-124, 2001; Pingault V., et al (2002) *Hum. Genet.* 111, 198-206); WO2004/045516 (Claim 1); WO2004/048938 (Example 2); WO2004/040000 (Claim 151); WO2003/087768 (Claim 1); WO2003/016475 (Claim 1); WO2003/016475 (Claim 1); WO2002/61087 (FIG. 1); WO2003/016494 (FIG. 6); WO2003/025138 (Claim 12; Page 144); WO2001/98351 (Claim 1; Page 124-125); EP0522868 (Claim 8; FIG. 2); WO2001/77172 (Claim 1; Page 297-299); US2003/109676; U.S. Pat. No. 6,518,404 (FIG. 3); U.S. Pat. No. 5,773,223 (Claim 1a; Col 31-34); WO2004/001004

(10) MSG783 (RNF124, hypothetical protein FLJ20315, Genbank accession no NM_017763); WO2003/104275 (Claim 1); WO2004/046342 (Example 2); WO2003/042661 (Claim 12); WO2003/083074 (Claim 14; Page 61); WO2003/018621 (Claim 1); WO2003/024392 (Claim 2; FIG. 93); WO2001/66989 (Example 6); Cross-references: LocusID:54894; NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138); Lab. Invest. 82 (11):1573-1582 (2002)); WO2003/087306; US2003/064397 (Claim 1; FIG. 1); WO2002/72596 (Claim 13; Page 54-55); WO2001/72962 (Claim 1; FIG. 4B); WO2003/104270 (Claim 11); WO2003/104270 (Claim 16); US2004/005598 (Claim 22); WO2003/042661 (Claim 12); US2003/060612 (Claim 12; FIG. 10); WO2002/26822 (Claim 23; FIG. 2); WO2002/16429 (Claim 12; FIG. 10); Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636); Xu, X. Z., et al Proc. Natl. Acad. Sci. U.S.A. 98 (19):10692-10697 (2001), Cell 109 (3): 397-407 (2002), J. Biol. Chem. 278 (33):30813-30820 (2003)); US2003/143557 (Claim 4); WO2000/40614 (claim 14; Page 100-103); WO2002/10382 (Claim 1; FIG. 9A); WO2003/042661 (Claim 12); WO2002/30268 (Claim 27; Page 391); US2003/219806 (Claim 4); WO2001/62794 (Claim 14; FIG. 1A-D); Cross-references: MIM:606936; NP_060106.2; NM_017636_1

(13) CRIPTO (CR, CR1, CRGF, CRIPTO, TDGF1, teratocarcinoma-derived growth factor, Genbank accession no NP_003203 or NM_003212); Ciccrodicola, A., et al *EMBO J.* 8 (7):1987-1991 (1989), *Am. J. Hum. Genet.* 49 (3):555-565 (1991)); US2003/224411 (Claim 1); WO2003/083041 (Example 1); WO2003/034984 (Claim 12); WO2002/88170 (Claim 2; Page 52-53); WO2003/024392 (Claim 2; FIG. 58); WO2002/16413 (Claim 1; Page 94-95, 105); WO2002/22808 (Claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1

(14) CD21 (CR2 (Complement receptor 2) or C3DR (C3d/Epstein Barr virus receptor) or Hs.73792 Genbank accession no. M26004); Fujisaku et al (1989) *J. Biol. Chem.* 264 (4):2118-2125); Weis J. J., et al *J. Exp. Med.* 167, 1047-1066, 1988; Moore M., et al *Proc. Natl. Acad. Sci. U.S.A.* 84, 9194-9198, 1987; Barel M., et al *Mol. Immunol.* 35, 1025-1031, 1998; Weis J. J., et al *Proc. Natl. Acad. Sci. U.S.A.* 83, 5639-5643, 1986; Sinha S. K., et al (1993) *J. Immunol.* 150, 5311-5320; WO2004/045520 (Example 4); US2004/005538 (Example 1); WO2003/062401 (Claim 9); WO2004/045520 (Example 4); WO91/02538 (FIG. 9.1-9.9); WO2004/020595 (Claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674); *Proc. Natl. Acad. Sci. U.S.A.* (2003) 100 (7):4126-4131, *Blood* (2002) 100 (9):3068-3076, Muller et al (1992) *Eur. J. Immunol.* 22 (8):1621-1625); WO2004/016225 (Claim 2, FIG. 140); WO2003/087768, US2004/101874 (Claim 1, page 102); WO2003/062401 (Claim 9); WO2002/78524 (Example 2); US2002/150573 (claim 5, page 15); U.S. Pat. No. 5,644,033; WO2003/048202 (Claim 1, pages 306 and 309); WO 99/58658, U.S. Pat. No. 6,534,482 (Claim 13, FIG. 17A/B); WO2000/55351 (Claim 11, pages 1145-1146); Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130); *Genome Res.* 13 (10):2265-2270 (2003), *Immunogenetics* 54 (2):87-95 (2002), *Blood* 99 (8):2662-2669 (2002), *Proc. Natl. Acad. Sci. U.S.A.* 98 (17):9772-9777 (2001), Xu M. J., et al (2001) *Biochem. Biophys. Res. Commun.* 280 (3):768-775; WO2004/016225 (Claim 2); WO2003/077836; WO2001/38490 (Claim 5; FIG. 18D-1-18D-2); WO2003/097803 (Claim 12); WO2003/089624 (Claim 25); Cross-references: MIM:606509; NP_110391.2; NM_030764_1

(17) HER2 (ErbB2, Genbank accession no, M11730); Coussens L., et al *Science* (1985) 20(4730):1132-1139); Yamamoto T., et al *Nature* 319, 230-234, 1986; Samba K., et al *Proc. Natl. Acad. Sci. U.S.A.* 82, 6497-6501, 1985; Swiercz J. M., et al *J. Cell Biol.* 165, 869-880, 2004; Kuhns J. J., et al *J. Biol. Chem.* 274, 36422-36427, 1999; Cho H.-S., et al *Nature* 421, 756-760, 2003; Ehsani A. et al (1993) *Genomics* 15, 426-429; WO2004/048938 (Example 2); WO2004/027049 (FIG. 11); WO2004/009622; WO2003/081210; WO2003/089904 (Claim 9); WO2003/016475 (Claim 1); US2003/118592; WO2003/008537 (Claim 1); WO2003/055439 (Claim 29; FIG. 1A-B); WO2003/025228 (Claim 37; FIG. 5C); WO2002/22636 (Example 13; Page 95-107); WO2002/12341 (Claim 68; FIG. 7); WO2002/13847 (Page 71-74); WO2002/14503 (Page 114-117); WO2001/53463 (Claim 2; Page 41-46); WO2001/41787 (Page 15); WO2000/44899 (Claim 52; FIG. 7); WO2000/20579 (Claim 3; FIG. 2); U.S. Pat. No. 5,869,445 (Claim 3; Col 31-38); WO9630514 (Claim 2; Page 56-61); EP1439393 (Claim 7); WO2004/043361 (Claim 7); WO2004/022709; WO2001/00244 (Example 3; FIG. 4); Accession: P04626; EMBL; M11767; AAA35808.1. EMBL; M11761; AAA35808.1

(18) NCA (CEACAM6, Genbank accession no. M18728); Barnett T., et al *Genomics* 3, 59-88, 1988 Tawaragi Y., et al *Biochem. Biophys. Res. Commun.* 150, 89-96, 1988; Strausberg R. L., et al *Proc. Natl. Acad. Sci. U.S.A.* 99:16899-16903, 2002; WO2004/063709; EP1439393 (Claim 7); WO2004/044178 (Example 4); WO2004/031238; WO2003/042661 (Claim 12); WO2002/78524 (Example 2); WO2002/86443 (Claim 27; Page 427); WO2002/60317 (Claim 2); Accession: P40199; Q14920; EMBL; M29541; AAA59915.1. EMBL; M18728

(19) MDP (DPEP1, Genbank accession no. BC017023); *Proc. Natl. Acad. Sci. U.S.A.* 99 (26):16899-16903 (2002)); WO2003/016475 (Claim 1); WO2002/64798 (Claim 33; Page 85-87); JP05003790 (FIG. 6-8); WO99/46284 (FIG. 9); Cross-references: MIM:179780; AAH17023.1; BC017023_1

(20) IL20Rα (IL20Rα, ZCYTOR7, Genbank accession no. AF184971); Clark H. F., et al *Genome Res.* 13, 2265-2270, 2003; Mungall A. J., et al *Nature* 425, 805-811, 2003; Blumberg H., et al *Cell* 104, 9-19, 2001; Dumoutier L, et al *J. Immunol.* 167, 3545-3549, 2001; Parrish-Novak J., et al *J. Biol. Chem.* 277, 47517-47523, 2002; Pletnev S., et al (2003) *Biochemistry* 42:12617-12624; Sheikh F., et al (2004) *J. Immunol.* 172, 2006-2010; EP1394274 (Example 11); US2004/005320 (Example 5); WO2003/029262 (Page 74-75); WO2003/002717 (Claim 2; Page 63); WO2002/22153 (Page 45-47); US2002/042366 (Page 20-21); WO2001/46261 (Page 57-59); WO2001/46232 (Page 63-65); WO98/37193 (Claim 1; Page 55-59); Accession: Q9UHF4; Q6UWA9; Q96SH8; EMBL; AF184971; AAF01320.1.

(21) Brevican (BCAN, REHAB, Genbank accession no. AF229053); Gary S. C., et al *Gene* 256, 139-147, 2000; Clark H. F., et al *Genome Res.* 13, 2265-2270, 2003; Strausberg et al *Proc. Natl. Aced. Sci. U.S.A.* 99, 16899-16903, 2002; US2003/186372 (Claim 11); US2003/186373 (Claim 11); US2003/119131 (Claim 1; FIG. 52); US2003/119122 (Claim 1; FIG. 52); US2003/119126 (Claim 1); US2003/119121 (Claim 1; FIG. 52); US2003/119129 (Claim 1); US2003/119130 (Claim 1); US2003/119128 (Claim 1; FIG. 52); US2003/119125 (Claim 1); WO2003/016475 (Claim 1); WO2002/02634 (Claim 1)

(22) EphB2R (DRT, ERK, Hek5, EPHT3, Tyro5, Genbank accession no. NM_004442); Chan, J. and Watt, V. M., *Oncogene* 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); Cross-references: MIM:600997; NP_004433.2; NM_004442_1

(23) ASLG659 (B7h, Genbank accession no. AX092328); US2004/0101899 (Claim 2); WO2003104399 (Claim 11); WO2004000221 (FIG. 3); US2003/165504 (Claim 1); US2003/124140 (Example 2); US2003/065143 (FIG. 60); WO2002/102235 (Claim 13; Page 299); US2003/091580 (Example 2); WO2002/10187 (Claim 6; FIG. 10); WO2001/94641 (Claim 12; FIG. 7b); WO2002/02624 (Claim 13; FIG. 1A-1B); US2002/034749 (Claim 54; Page 45-46); WO2002/06317 (Example 2; Page 320-321, Claim 34; Page 321-322); WO2002/71928 (Page 468-469); WO2002/02587 (Example 1; FIG. 1); WO2001/40269 (Example 3; Pages 190-192); WO2000/36107 (Example 2; Page 205-207); WO2004/053079 (Claim 12); WO2003/004989 (Claim 1); WO2002/71928 (Page 233-234, 452-453); WO 01/16318

(24) PSCA (Prostate stem cell antigen precursor, Genbank accession no. AJ297436); Reiter R. E., et al *Proc. Natl. Acad. Sci. USA* 95, 1735-1740, 1998; Gu Z., et al *Oncogene* 19, 1288-1296, 2000; *Biochem. Biophys. Res. Common.* (2000) 275(3):783-788; WO2004/022709; EP1394274 (Example 11); US2004/018553 (Claim 17); WO2003/008537 (Claim 1); WO2002/81646 (Claim 1; Page 164); WO2003/003906 (Claim 10; Page 288); WO2001/40309 (Example 1 FIG. 17); US2001/055751 (Example 1; FIG. 1b); WO2000/32752 (Claim 18; FIG. 1); WO98/51805 (Claim 17; Page 97); WO98/51824 (Claim 10; Page 94); WO98/40403 (Claim 2; FIG. 1B); Accession: O43653; EMBL; AF043498; AAC39607.1

(25) GEDA (Genbank accession No. AY260763); AAP14954 lipoma HMGIC fusion-partner-like protein/pid=AAP14954.1—*Homo sapiens* (human); WO2003/054152 (Claim 20); WO2003/000842 (Claim 1); WO2003/023013 (Example 3, Claim 20); US2003/194704 (Claim 45); Cross-references; GI:30102449; AAP14954.1; AY260763_1

(26) BAFF-R (B cell-activating factor receptor, BLyS receptor 3, BR3, Genbank accession No. AF116456); BAFF receptor/pid=NP_443177.1—*Homo sapiens.* Thompson, J. S., et al *Science* 293 (5537), 2108-2111 (2001); WO2004/058309; WO2004/011611; WO2003/045422 (Example; Page 32-33); WO2003/014294 (Claim 35; FIG. 6B); WO2003/035846 (Claim 70; Page 615-616); WO2002/94852 (Col 136-137); WO2002/38766 (Claim 3; Page 133); WO2002/24909 (Example 3; FIG. 3); Cross-references: MIM:606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession No. AK026467); Wilson et al (1991) *J. Exp. Med.* 173:137-146; WO2003/072036 (Claim 1; FIG. 1); Cross-references: MIM:107266; NP_001762.1; NM_001771_1

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10); WO2003/088808, US2003/0228319; WO2003/062401 (claim 9); US2002/150573 (claim 4, pages 13-14); WO99/58658 (claim 13, FIG. 16) WO92/07574 (FIG. 1), U.S. Pat. No. 5,644,033; Ha et al (1992) *J. Immunol.* 148(5):1526-1531; Müller et al (1992) *Eur. J. Immunol.* 22:1821-1825; Hashimoto et al (1994) *Immunogenetics* 40(4):287-295; Preud'homme et al (1992) *Clin. Exp. Immunol.* 90(1):141-146; Yu et al (1992) *J. Immunol.* 148(2) 633-637; Sakaguchi et al (1988) *EMBO J.* 7(11): 3457-3464

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP 0017071); WO2004/040000; WO2004/015426; US2003/105292 (Example 2); U.S. Pat. No. 6,555,339 (Example 2); WO2002/61087 (FIG. 1); WO2001/57188 (Claim 20, page 269); WO2001/72830 (pages 12-13); WO2000/22129 (Example 1, pages 152-153, Example 2, pages 254-256); WO99/28468 (claim 1, page 38); U.S. Pat. No. 5,440,021 (Example 2, col 49-52); WO94/28931 (pages 56-58); WO92/17497 (claim 7, FIG. 5); Dobner et al (1992) *Eur. J. Immunol.* 22:2795-2799; Barella et al (1995) *Biochem. J.* 309:773-779

(30) HLA-DOB (Beta subunit of MHC class II molecule (Ia antigen) that binds peptides and presents them to CD4+ T lymphocytes); 273 ea, pI: 6.56, MW: 30820. TM: 1 [P] Gene Chromosome: 6p21.3, Genbank accession No. NP_002111.1); Tonnelle et al (1985) *EMBO J.* 4(11):2839-2847; Jonsson et al (1989) *Immunogenetics* 29(6):411-413; Beck et al (1992) *J. Mol. Biol.* 228:433-441; Strausberg et al (2002) *Proc. Natl. Acad. Sci USA* 99:16899-16903; Servenius et al (1987) *J. Biol. Chem.* 262:8759-8766; Beck et al (1996) *J. Mol. Biol.* 255:1-13; Naruse et al (2002) *Tissue Antigens* 59:512-519; WO99/58658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) *Immunogenetics* 30(1):66-68; Larhammar et al (1985) *J. Biol. Chem.* 260(26):14111-14119

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa, pI: 7.63, MW: 47206 TM: 1 [P] Gene Chromosome: 17p13.3, Genbank accession No. NP_002552.2); Le et al (1997) *FEBS Lett.* 418(1-2):195-199; WO2004/047749; WO2003/072035 (claim 10); Touchman et al (2000) *Genome Res.* 10:165-173; WO2002/22660 (claim 20); WO2003/093444 (claim 1); WO2003/087768 (claim 1); WO2003/029277 (page 82)

(32) CD72 (B-cell differentiation antigen CD72, Lyb-2); 359 aa, pI: 8.66, MW: 40225, TM: 1 [P] Gene Chromosome; 9p13.3, Genbank accession No. NP_001773.1); WO2004042346 (claim 65); WO2003/026493 (pages 51-52, 57-58); WO2000/75655 (pages 105-106); Von Hoegen et al (1990) *J. Immunol.* 144(12):4870-4877; Strausberg et al (2002) *Proc. Natl. Acad. Sci. USA* 99:16899-16903.

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1); US2002/193567; WO97/07198 (claim 11, pages 39-42); Miura et al (1996) *Genomics* 38(3):299-304; Miura et al (1998) *Blood* 92:2815-2822; WO2003/083047 WO97/44452 (claim 8, pages 57-61); WO2000/12130 (pages 24-26)

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI; 5.28, MW: 46925 TM: 1 [P] Gene Chromosome: 1q21-1q22, Genbank accession No. NP_443170.1); WO2003/077836; WO2001/38490 (claim 6, FIG. 18E-1-18-E-2); Davis et all (2001) *Proc. Natl. Acad. Sci. USA* 98(17):9772-9777; WO2003/089624 (claim 8); EP1347046 (claim 1); WO2003/089624 (claim 7)

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI; 6.88. MW: 106468, TM: 1 [P] Gene Chromosome: 1q21, Genbank accession No. Human: AF343662, AF343663, AF343664, AF343665, AF369794, AF397453, AK090423, AK090475, AL834187, AY358085; Mouse: AK089756, AY158090, AY506558; NP_112571.1; WO2003/024392 (claim 2, FIG. 97); Nakayama et al (2000) *Biochem. Biophys. Res. Commun.* 277(1):124-127; WO2003/077836; WO2001/38490 (claim 3, FIG. 18B-1-18B-2)

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436; WO2004/074320; JP2004113151; WO2003/042661; WO2003/009814; EP1295944 (pages 69-70); WO2002/30268 (page 329); WO2001/90304; US2004/249130; US2004/022727; WO2004/063355; US2004/197325; US2003/232350; US2004/005563; US2003/124579; Horie et al (2000) *Genomics* 67:146-152; Uchida et al (1999) *Biochem. Biophys. Res. Commun.* 266:593-602; Liang et al (2000) *Cancer Res.* 60:4907-12; Glynne-Jones et al (2001) *Int J Cancer.* October 15; 94(2):178-84.

The parent antibody may also be a fusion protein comprising an albumin-binding peptide (ABP) sequence (Dennis et al. (2002) "Albumin Binding As A General Strategy For Improving The Pharmacokinetics Of Proteins" *J Biol Chem.* 277:35035-35043; WO 01/45746). Antibodies of the invention include fusion proteins with ABP sequences taught by: (i) Dennis et al (2002) *J Biol Chem.* 277:35035-35043 at Tables III and IV, page 35038; (ii) US 2004/0001827 at [0076]; and (iii) WO 01/45746 at pages 12-13, and all of which are incorporated herein by reference.

In one embodiment, the antibody has been raised to target specific the tumour related antigen $\alpha_v\beta_6$.

The cell binding agent may be labelled, for example to aid detection or purification of the agent either prior to incorporation as a conjugate, or as part of the conjugate. The label may be a biotin label. In another embodiment, the cell binding agent may be labelled with a radioisotope.

R and R'

In one embodiment, R is independently selected from optionally substituted $C_{1-12}$ alkyl, $C_{3-20}$ heterocyclyl and $C_{5-20}$ aryl groups. These groups are each defined in the substituents section below.

In one embodiment, R is independently optionally substituted $C_{1-12}$ alkyl.

In one embodiment, R is independently optionally substituted $C_{3-20}$ heterocyclyl.

In one embodiment, R is independently optionally substituted $C_{5-20}$ aryl.

In one embodiment, R is independently optionally substituted $C_{1-12}$ alkyl.

Described above in relation to $R^2$ are various embodiments relating to preferred alkyl and aryl groups and the identity and number of optional substituents. The preferences set out for $R^2$ as it applies to R are applicable, where appropriate, to all other groups R, for examples where $R^6$, $R^7$, $R^8$ or $R^9$ is R.

The preferences for R apply also to R'.

In some embodiments of the invention there is provided a compound having a substituent group —NRR'. In one embodiment, R and R' together with the nitrogen atom to which they are attached form an optionally substituted 4-, 5-, 6 or 7-membered heterocyclic ring. The ring may contain a further heteroatom, for example N, O or S.

In one embodiment, the heterocyclic ring is itself substituted with a group R. Where a further N heteroatom is present, the substituent may be on the N heteroatom.

R"

R" is a $C_{3-12}$ alkylene group, which chain may be interrupted by one or more heteroatoms, e.g. O, S, N(H), NMe and/or aromatic rings, e.g. benzene or pyridine, which rings are optionally substituted.

In one embodiment, R" is a $C_{3-12}$ group, which chain may be interrupted by one or more heteroatoms and/or aromatic rings, e.g. benzene or pyridine.

In one embodiment, the alkylene group is optionally interrupted by one or more heteroatoms selected from O, S, and NMe and/or aromatic rings, which rings are optionally substituted.

In one embodiment, the aromatic ring is a $C_{5-20}$ arylene group, where arylene pertains to a divalent moiety obtained by removing two hydrogen atoms from two aromatic ring atoms of an aromatic compound, which moiety has from 5 to 20 ring atoms.

In one embodiment, R" is a $C_{3-12}$ alkylene group, which chain may be interrupted by one or more heteroatoms, e.g. O, S, N(H), NMe and/or aromatic rings, e.g. benzene or pyridine, which rings are optionally substituted by $NH_2$.

In one embodiment, R" is a $C_{3-12}$ alkylene group.

In one embodiment, R" is selected from a $C_3$, $C_5$, $C_7$, $C_9$ and a $C_{11}$ alkylene group.

In one embodiment, R" is selected from a $C_3$, $C_5$ and a $C_7$ alkylene group.

In one embodiment, R" is selected from a C and a $C_5$ alkylene group.

In one embodiment, R" is a $C_3$ alkylene group.

In one embodiment, R" is a $C_5$ alkylene group.

The alkylene groups listed above may be optionally interrupted by one or more heteroatoms and/or aromatic rings, e.g. benzene or pyridine, which rings are optionally substituted.

The alkylene groups listed above may be optionally interrupted by one or more heteroatoms and/or aromatic rings, e.g. benzene or pyridine.

The alkylene groups listed above may be unsubstituted linear aliphatic alkylene groups.

X

In one embodiment, X is selected from O, S, or N(H).

Preferably, X is O.

E

The compounds where one or both C rings is replaced by a ring of formula E, have a group $R^2$ which with either of $R^1$ or $R^3$, together with carbon atoms of the C ring to which they are attached, form an optionally substituted benzene ring. The optionally substituted benzene ring may be regarded as fused to the C ring of the pyrrolobenzodiazepine. The fused benzene ring may be referred to as the D ring. The structure of the fused ring is illustrated below:

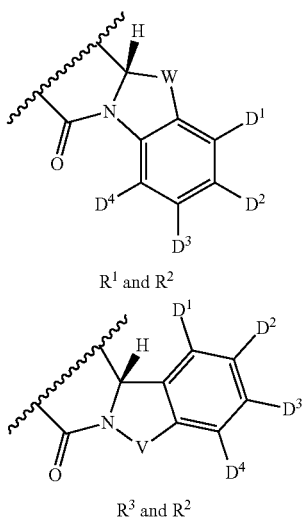

R¹ and R²

R³ and R² where each of $D^1$, $D^2$, $D^3$ and $D^4$ represents H or a substituent.

In one embodiment, the benzene ring is unsubstituted.

In one embodiment, the benzene ring is optionally substituted with one, two, three of four groups selected from OH, CN, R, OR, O—SO$_2$—R, CO$_2$R, COR, SH, SR, NH$_2$, NHR, NRR', NO$_2$, Me$_3$Sn and halo.

In one embodiment, the benzene ring is monosubstituted. The monosubstituent may be any one of $D^1$, $D^2$, $D^3$ or $D^4$ (the rest being H). In one embodiment the benzene ring is substituted at $D^2$, and $D^1$, $D^3$ and $D^4$ are each H. In one embodiment the benzene ring is substituted at $D^3$, and $D^1$, $D^2$ and $D^4$ are each H.

In one embodiment, $R^2$ with $R^1$, together with carbon atoms of the C ring to which they are attached, form an optionally substituted benzene ring.

The preferences for V and W are set out below.

F

In the compounds where one or both C rings is replaced by a ring of formula F:

In one embodiment, U is CH$_2$ when T is NR, BH, SO, or SO$_2$.

In one embodiment, T is CH$_2$ or CO when U is NR, O or S.

In one embodiment, T is selected from CH$_2$ and CO.
In one embodiment, U is selected from NR, O and S.
In one embodiment, Y is (CH$_2$)$_n$, where n is 1 or 2.
In one embodiment, the C ring of the compound A-B has a structure selected from those shown below:

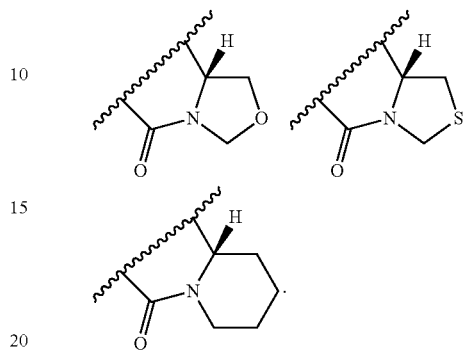

V and W

V and W are each selected from (CH$_2$)$_n$, O, S, NR, CHR, and CRR' where n is 2, 3 or 4, except that V is C when $R^1$ and $R^2$, together with carbon atoms of the C ring to which they are attached, form an optionally substituted benzene ring, and W is C when $R^3$ and $R^2$, together with carbon atoms of the C ring to which they are attached, form an optionally substituted benzene ring.

In one embodiment, when one of V and W is C, the other of V and W is selected from CH$_2$ and NR.

In one embodiment, when one of V and W is C, the other of V and W is CH$_2$.

Preferred Compounds

In one embodiment, the conjugate is a dimer wherein each of the PBD moieties has a C2 methylene group i.e. each $R^2$ is =CH$_2$. It is preferred that the cell binding agent is an antibody.

In another embodiment, the conjugate is a dimer wherein each of the monomers has a C2 aryl group i.e. each $R^2$ is optionally substituted C$_{5-20}$ aryl, and there is a double bond between C2 and C3 in each PBD moiety. R is preferred that the cell binding agent is an antibody.

C2 Alkylene

In one embodiment, the conjugate is a compound:

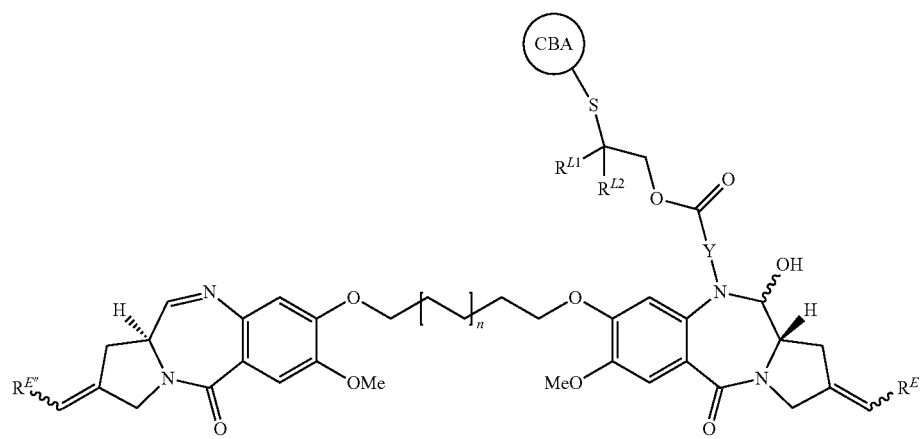

and more preferably:

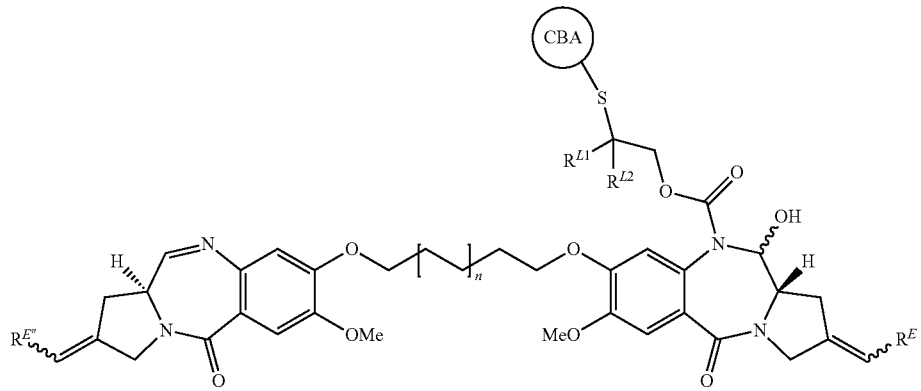

wherein CBA is a cell binding agent such as an antibody or a cyclic or linear peptide, and n is 0 or 1. Y, $R^{L1}$ and $R^{L2}$ are as previously defined, and $R^E$ and $R^{E''}$ are each independently selected from H or $R^D$.

For each of the compounds above, the following preferences may apply, where appropriate:
n is 0;
n is 1;
$R^E$ is H;
$R^E$ is $R^D$, where $R^D$ is optionally substituted alkyl;
$R^E$ is $R^D$, where $R^D$ is methyl;
CBA is an antibody;
CBA is a cyclic peptide;
$R^{L1}$ and $R^{L2}$ are H;
$R^{L1}$ and $R^{L2}$ are Me.

C2 Aryl

In one embodiment, the conjugate is a compound:

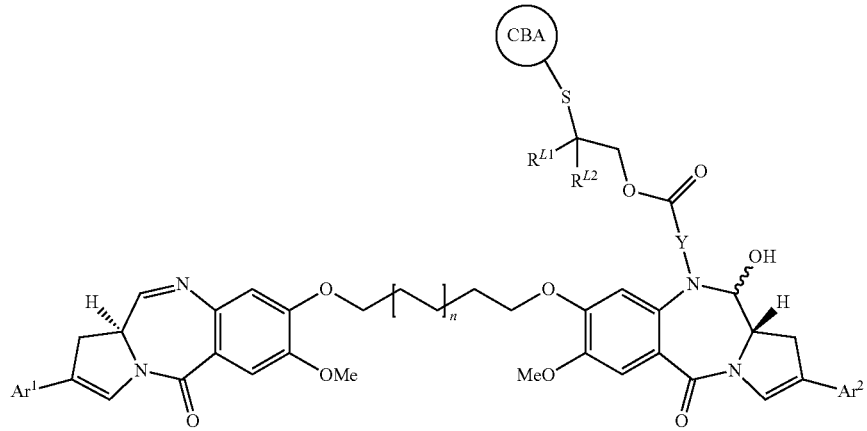

and more preferably:

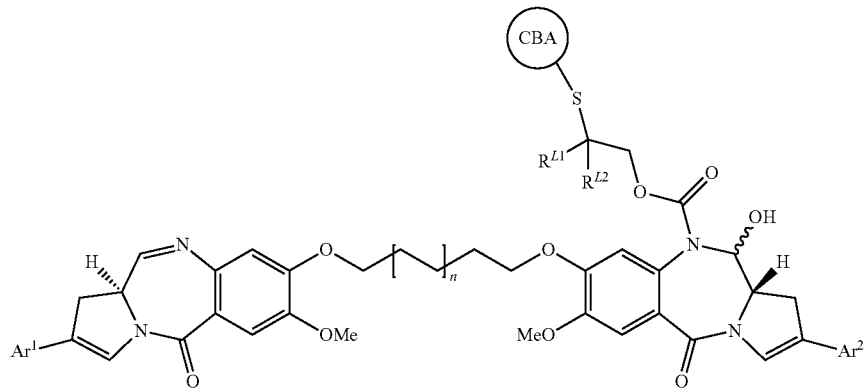

wherein CBA is a cell binding agent such as an antibody or a cyclic or linear peptide, Y, $R^{L1}$ and $R^{L2}$ are as previously defined $Ar^1$ and $Ar^2$ are each independently optionally substituted $C_{5-20}$ aryl, and n is 0 or 1. $Ar^1$ and $Ar^2$ may be the same or different.

In one embodiment, $Ar^1$ and $Ar^2$ in each of the embodiments above are each independently selected from optionally substituted phenyl, furanyl, thiophenyl and pyridyl.

In one embodiment, $Ar^1$ and $Ar^2$ in each of the embodiments above is optionally substituted phenyl.

In one embodiment, $Ar^1$ and $Ar^2$ in each of the embodiments above is optionally substituted thien-2-yl or thien-3-yl.

In one embodiment, $Ar^1$ and $Ar^2$ in each of the embodiments above is optionally substituted quinolinyl or isoquinolinyl.

The quinolinyl or isoquinolinyl group may be bound to the PBD core through any available ring position. For example, the quinolinyl may be quinolin-2-yl, quinolin-3-yl, quinolin-4-yl, quinolin-5-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4-yl, isoquinolin-5-yl, isoquinolin-6-yl, isoquinolin-7-yl and isoquinolin-8-yl. Of these isoquinolin-3-yl and isoquinolin-6-yl may be preferred.

C2 Vinyl

In one embodiment, the conjugate is a compound:

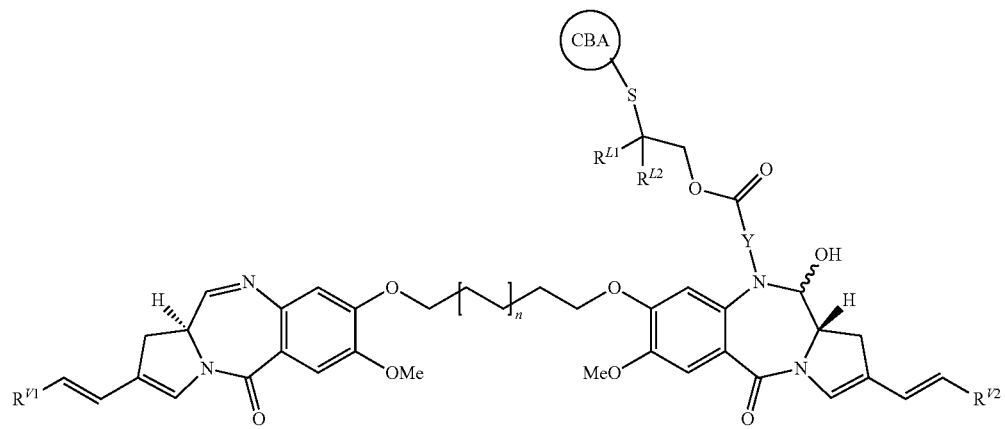

and more preferably:

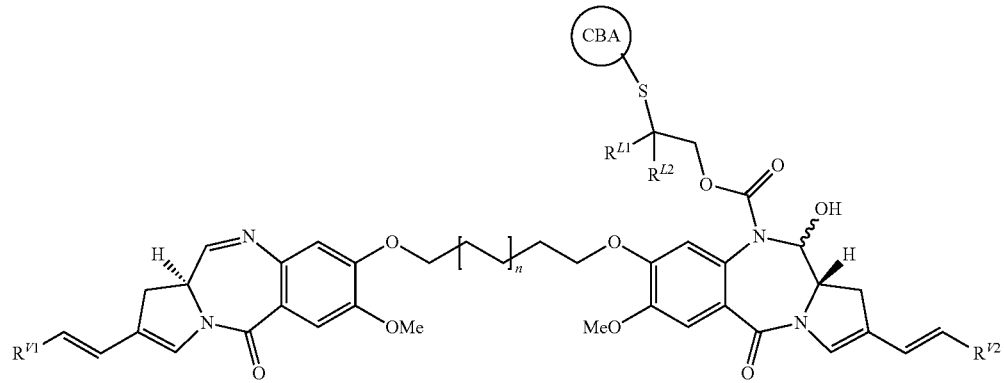

wherein CBA is a cell binding agent such as an antibody or a cyclic or linear peptide, Y, $R^{L1}$ and $R^{L2}$ are as previously defined, $R^{V1}$ and $R^{V2}$ are independently selected from H, methyl, ethyl and phenyl (which phenyl may be optionally substituted with fluoro, particularly in the 4 position) and $C_{5-6}$ heterocyclyl, and n is 0 or 1. $R^{V1}$ and $R^{V2}$ may be the same or different.

In some of the above embodiments, $R^{V1}$ and $R^{V2}$ may be independently selected from H, phenyl, and 4-fluorophenyl.

Preferred Intermediates

The present invention also provides intermediates for use in the preparation of the conjugate compounds described herein.

Preferred intermediates are described below, and correspond closely to the preferred conjugates described above.

In one embodiment, the intermediate is a compound:

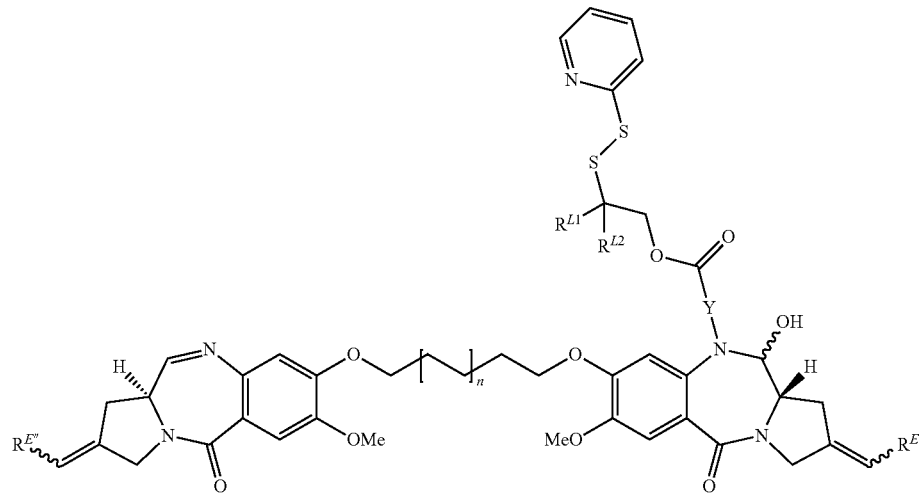

and more preferably:

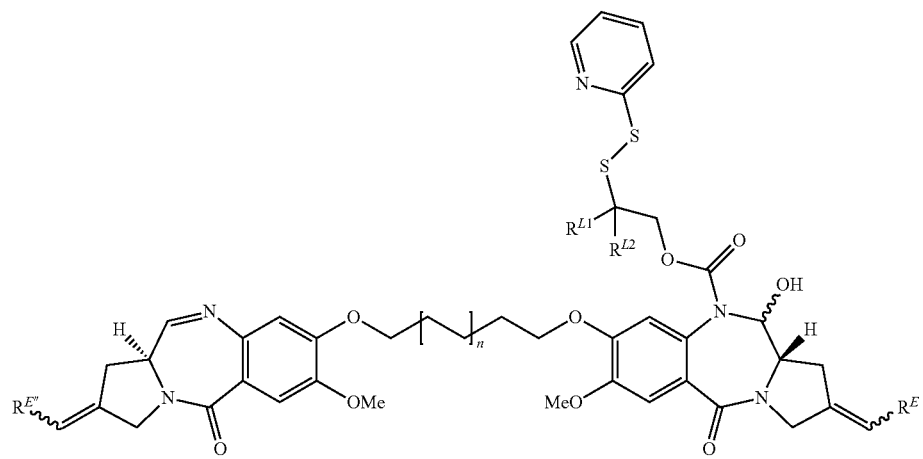

wherein n is 0 or 1, Y, $R^{L1}$ and $R^{L2}$ are as previously defined, and $R^E$ and $R^{E''}$ are each independently selected from H or $R^D$.

In one embodiment, the intermediate is a compound:
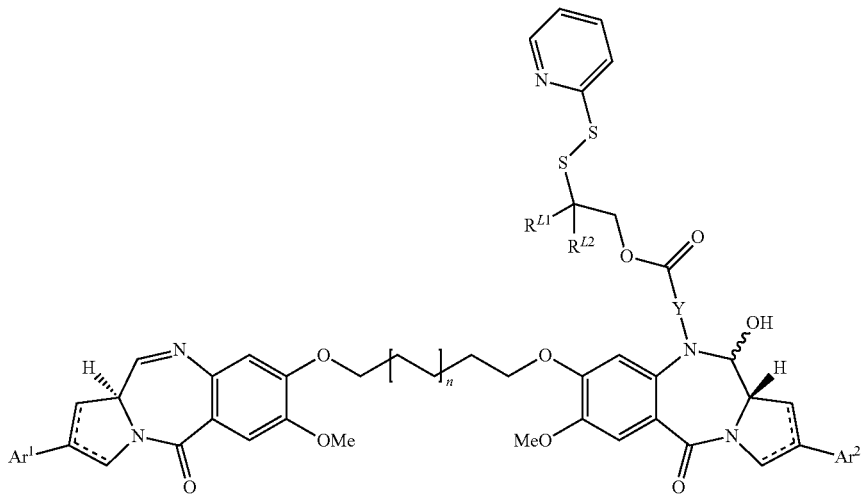
and more preferably:
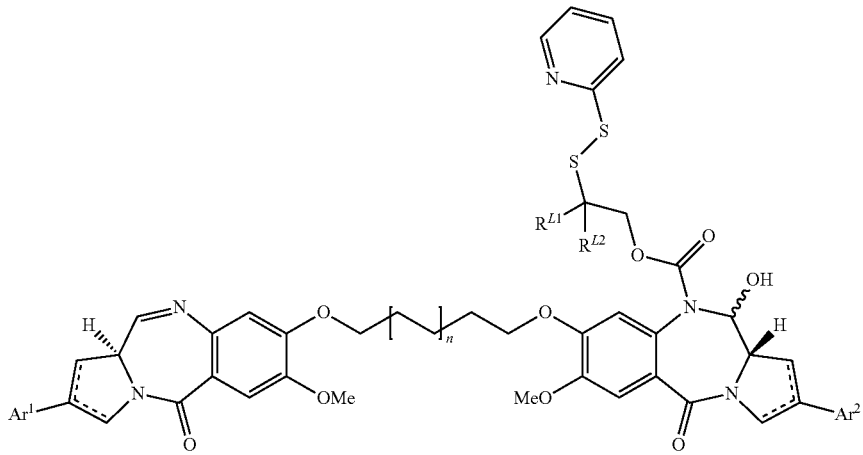
wherein Y, $R^{L1}$ and $R^{L2}$ are as previously defined $Ar^1$ and $Ar^2$ are each independently optionally substituted $C_{5-20}$ aryl, and n is 0 or 1. $Ar^1$ and $Ar^2$ may be the same or different.

In one embodiment, the intermediate is a compound:

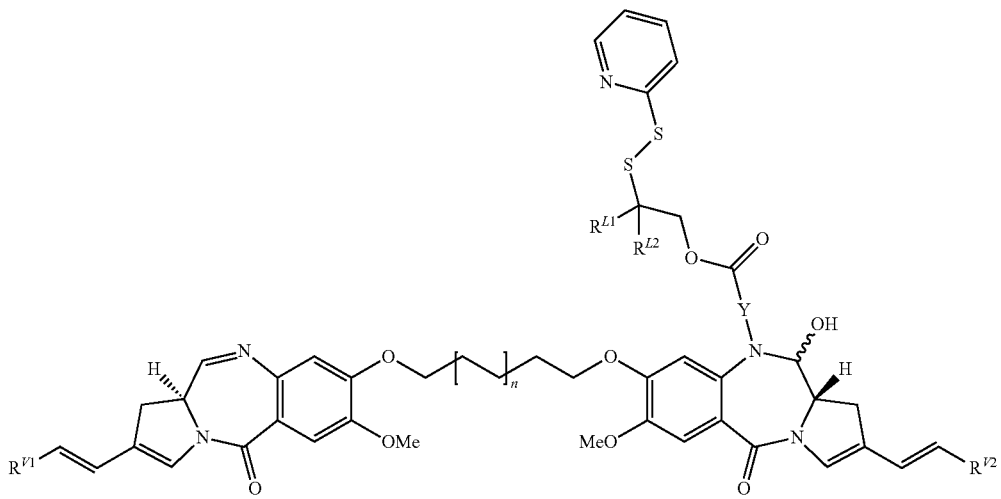

and more preferably:

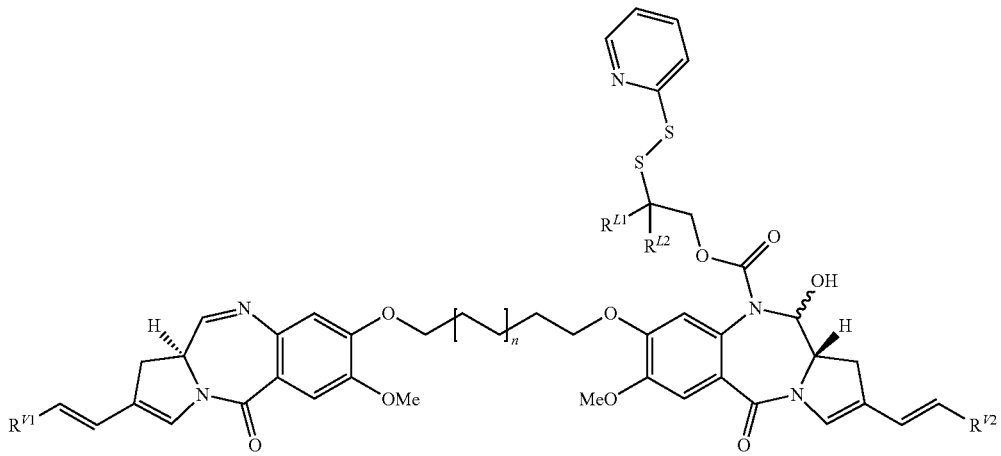

wherein Y, $R^{L1}$ and $R^{L2}$ are as previously defined, $R^{V1}$ and $R^{V2}$ are independently selected from H, methyl, ethyl and phenyl (which phenyl may be optionally substituted with fluoro, particularly in the 4 position) and $C_{5-6}$ heterocyclyl, and n is 0 or 1. $R^{V1}$ and $R^{V2}$ may be the same or different.

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

In a preferred embodiment, the substituents described herein (which include optional substituents) are limited to those groups that are not reactive to a cell binding agent. The link to the cell binding agent in the present case is formed from the N10 position of the PBD compound through a linker group (comprising, for example, $L^1$, $L^2$ and A) to the cell binding agent. Reactive functional groups located at other parts of the PBD structure may be capable of forming additional bonds to the cell binding agent (this may be referred to as crosslinking). These additional bonds may alter transport and biological activity of the conjugate. Therefore, in some embodiment, the additional substituents are limited to those lacking reactive functionality.

In one embodiment, the substituents are selected from the group consisting of R, OR, SR, NRR', $NO_2$, halo, $CO_2R$, COR, $CONH_2$, CONHR, and CONRR'.

In one embodiment, the substituents are selected from the group consisting of R, OR, SR, NRR', $NO_2$, $CO_2R$, COR, $CONH_2$, CONHR, and CONRR'.

In one embodiment, the substituents are selected from the group consisting of R, OR, SR, NRR', $NO_2$, and halo.

In one embodiment, the substituents are selected from the group consisting of R, OR, SR, NRR', and $NO_2$.

Any one of the embodiment mentioned above may be applied to any one of the substituents described herein.

Alternatively, the substituents may be selected from one or more of the groups listed below.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$) hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

An alkyl group may optionally be interrupted by one or more heteroatoms selected from O, N(H) and S. Such groups may be referred to as "heteroalkyl".

$C_{2-20}$ Heteroalkyl: The term "$C_{2-12}$ heteroalkyl" as used herein, pertains to a monovalent moiety obtained by removing a hydrogen atom from a carbon atom of a hydrocarbon compound having from 2 to 12 carbon atoms, and one or more heteroatoms selected from O, N(H) and S, preferably O and S.

Examples of heteroalkyl groups include, but are not limited to those comprising one or more ethylene glycol units of the type —(OCH$_2$CH$_2$)—. The terminal of a heteroalkyl group may be the primary form of a heteroatom, e.g. —OH, —SH or —NH$_2$. In a preferred embodiment, the terminal is —CH$_3$.

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —CH$_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_5$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_6$), triazine ($C_6$); and,
$N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_9$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine (N pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.
Hydroxy: —OH.
Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a heterocyclyloxy group), or a $C_{5-20}$ aryl group (also referred to as a $C_{5-20}$ aryloxy group), preferably a $C_{1-7}$alkyl group.
Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH($OR^1$)($OR^2$), wherein $R^1$ and are independently acetal substituents, for example, a $C_{1-7}$ alkyl group, a $C_{3-20}$ heterocyclyl group, or a $C_{5-20}$ aryl group, preferably a $C_{1-7}$ alkyl group, or in the case of a "cyclic" acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_7$, and —CH(OMe)(OEt).

Hemiacetal: —CH(OH)($OR^1$), wherein $R^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR($OR^1$)($OR^2$), where $R^1$ and $R^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)($OR^1$), where $R^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.
Thione (thioketone): =S.
Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.
Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.
Thiocarboxy (thiocarboxylic acid): —C(=S)SH.
Thiolocarboxy (thiolocarboxylic acid): —C(=O)SH.
Thionocarboxy (thionocarboxylic acid): —C(=S)OH.
Imidic acid: —C(=NH)OH.
Hydroxamic acid: —C(=NOH)OH.
Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

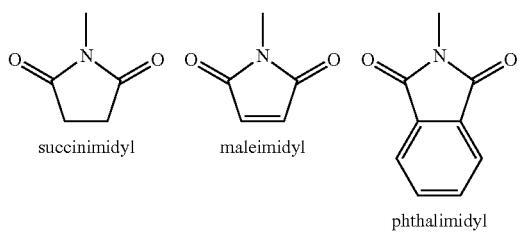

succinimidyl    maleimidyl    phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

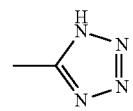

Imino =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.

Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(O)$_2$OR, wherein R is a sulfonate substituent, for example, a $C_{1-7}$ group, a $C_{3-20}$ heterocyclyl group, or a $C_{5-20}$ aryl group, preferably a $C_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR: wherein R is a sulfate substituent, for example, a $O_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example: —H, a $C_{1-7}$ alkyl group, a $C_{3-20}$ heterocyclyl group, or a $C_{5-2}$, aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O)(CH$_3$)$_2$, —P(=O)(CH$_2$CH$_3$)$_2$; —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene $C_{3-12}$ alkylene: The term "$C_{3-12}$ alkylene", as used herein, pertains to a tridentate moiety obtained by removing two hydrogen atoms, both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated $C_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH—$_2$CH$_2$CH$_2$CH$_2$— (heptylene).

Examples of branched saturated C$_{3-12}$ alkylene groups include, but are not limited to, —CH(CH$_3$)CH$_2$—, —CH(CH$_3$)CH$_2$H$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{3-12}$ alkylene groups (C$_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH=CH—CH$_2$—, —CH=CH—CH$_2$—, —CH=CH—CH$_2$—CH$_2$—CH=CH—, and —CH$_2$—C≡C—CH$_2$—.

Examples of branched partially unsaturated C$_{3-12}$ alkylene groups (C$_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated C$_{3-12}$ alkylene groups (C$_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated C$_{3-12}$ alkylene groups (C$_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Includes Other Forms

Unless otherwise specified, included in the above are the well known ionic, salt, solvate, and protected forms of these substituents. For example, a reference to carboxylic acid (—COOH) also includes the anionic (carboxylate) form (—COO), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ stay be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acid 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term 'solvate' is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

The invention includes compounds where a solvent adds across the imine bond of the PBD moiety, which is illustrated below where the solvent is water or an alcohol (R$^A$OH, where R$^A$ is C$_{1-4}$ alkyl):

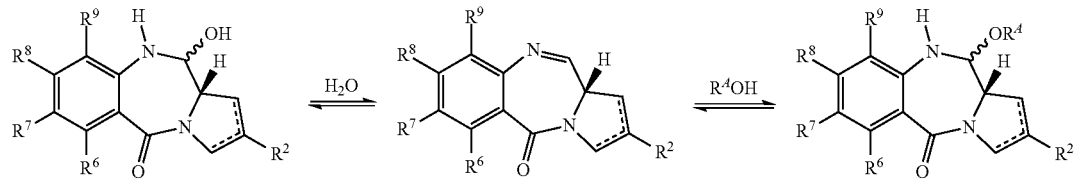

These forms can be called the carbinolamine and carbinolamine ether forms of the PBD (as described in the section relating to R$^{10}$ above). The balance of these equilibria depend on the conditions in which the compounds are found, as well as the nature of the moiety itself.

These particular compounds may be isolated in solid form, for example, by lyophilisation.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S. "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

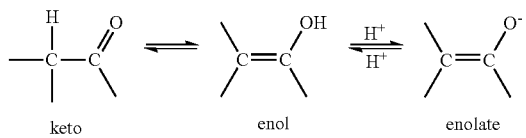

keto      enol      enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T), C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Biological Activity

In Vitro Cell Proliferation Assays

Generally, the cytotoxic or cytostatic activity of an antibody-drug conjugate (ADC) is measured by: exposing mammalian cells having receptor proteins, e.g. HER2, to the antibody of the ADC in a cell culture medium; culturing the cells for a period from about 6 hours to about 5 days; and measuring cell viability. Cell-based in vitro assays are used to measure viability (proliferation), cytotoxicity, and induction of apoptosis (caspase activation) of an ADC of the invention.

The in vitro potency of antibody-drug conjugates can be measured by a cell proliferation assay. The CellTiter-Glo® Luminescent Cell Viability Assay is a commercially available (Promega Corp., Madison. Wis.), homogeneous assay method based on the recombinant expression of *Coleoptera* luciferase (U.S. Pat. Nos. 5,583,024; 5,674,713 and 5,700, 670). This cell proliferation assay determines the number of viable cells in culture based on quantitation of the ATP present, an indicator of metabolically active cells (Crouch et al (1993) *J. Immunol. Meth.* 160:81-88; U.S. Pat. No. 6,602,677). The CellTiter-Glo® Assay is conducted in 96 well format, making it amenable to automated high-throughput screening (HTS) (Cree et al (1995) *Anticancer Drugs* 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

In Vivo Efficacy

The in vivo efficacy of antibody-drug conjugates (ADC) of the invention can be measured by tumor xenograft studies in mice. For example, the in vivo efficacy of an anti-HER2 ADC of the invention can be measured by a high expressing HER2 transgenic explant mouse model. An allograft is propagated from the Fo5 mmtv transgenic mouse which does not respond to, or responds poorly to, HERCEPTIN® therapy. Subjects were treated once with ADC at certain dose levels (mg/kg) and PBD drug exposure (µg/m$^2$); and placebo buffer control (Vehicle) and monitored over two weeks or more to measure the time to tumor doubling, log cell kill, and tumor shrinkage.

Use

The conjugates of the invention may be used to provide a PBD compound at a target location.

The target location is preferably a proliferative cell population. The antibody is an antibody for an antigen present in a proliferative cell population.

In one embodiment the antigen is absent or present at a reduced level in a non-proliferative cell population compared to the amount of antigen present in the proliferative cell population, for example a tumour cell population.

At the target location the linker may be cleaved so as to release a compound of formulae B or C Thus, the conjugate may be used to selectively provide a compound of formulae B or C to the target location.

The linker may be cleaved by an enzyme present at the target location.

The target location may be in vitro, in vivo or ex vivo.

The antibody-drug conjugate (ADC) compounds of the invention include those with utility for anticancer activity. In particular, the compounds include an antibody conjugated, i.e. covalently attached by a linker, to a PBD drug moiety, i.e. toxin. When the drug is not conjugated to an antibody, the PBD drug has a cytotoxic effect. The biological activity of the PBD drug moiety is thus modulated by conjugation to an antibody. The antibody-drug conjugates (ADC) of the invention selectively deliver an effective dose of a cytotoxic agent to tumor tissue whereby greater selectivity, i.e. a lower efficacious dose, may be achieved.

Thus, in one aspect, the present invention provides a conjugate compound as described herein for use in therapy.

In a further aspect there is also provides a conjugate compound as described herein for use in the treatment of a proliferative disease. A second aspect of the present invention provides the use of a conjugate compound in the manufacture of a medicament for treating a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

In one embodiment, the treatment is of a pancreatic cancer.

In one embodiment, the treatment is of a tumour having $\alpha_v\beta_6$ integrin on the surface of the cell.

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, antiphospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteritis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Methods of Treatment

The conjugates of the present invention may be used in a method of therapy. Also provided is a method of treatment, comprising administering to a subject in need of treatment a therapeutically-effective amount of a conjugate compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound of the invention may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®. Genentech), temozolomide (4-methyl-5-oxo-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyatt)), lapatinib (TYKERB®, GSK572016, Glaxo Smith Kline), lonafarnib (SARASAR™, SCH 66336, Sobering Plough), sorafenib (NEXAVAR®, BAY43-9006, Bayer Labs), gefitinib (IRESSA®, AstraZeneca), irinoteran (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571

(SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; caltystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omega1I (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine: mercaptopurine; methotrexate; platinum analogs such as cisplatin and carboplatin; vinblastine; etoposide (VP-16); ifosfamide, mitoxantrone; vincristine; vinorelbine (NAVELBINE®); novantrone, teniposide; edatrexate; daunomycin; aminopterin; capecitabine (XELODA®, Roche); ibandronate; CPT-11; topoisomerase inhibitor RFS 2000; difluoromethylomithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®, tamoxifen citrate), raloxifene, droloxifene, 4-hydroxytamoxifen, trioxifene, keoxifene. LY117018, onapristone, and FARESTON® (toremifene citrate); (ii) aromatase inhibitors that inhibit the enzyme aromatase, which regulates estrogen production in the adrenal glands, such as for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such, as bevacizumab (AVASTiN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); paniturnumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the conjugates of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present invention, and for use in accordance with the present invention, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringers Injection. Preservatives, stabilisers, buffers, antioxidants and/or other additives may be included, as required, Formulations While it is possible for the conjugate compound to be used (e.g., administered) alone, it is often preferable to present it as a composition or formulation.

In one embodiment, the composition is a pharmaceutical composition (e.g., formulation, preparation, medicament) comprising a conjugate compound, as described herein, and a pharmaceutically acceptable carrier, diluent, or excipient.

In one embodiment, the composition is a pharmaceutical composition comprising at least one conjugate compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives,* 2nd Edition (eds. M. Ash and I. Ash), 2001 (Synapse Information Resources, Inc., Endicott, N.Y., USA), *Remington's Pharmaceutical Sciences,* 20th edition, pub. Lippincott, Williams & Wilkins, 2000; and *Handbook of Pharmaceutical Excipients,* 2nd edition, 1994.

Another aspect of the present invention pertains to methods of making a pharmaceutical composition comprising admixing at least one [$^{11}$C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride injection, Ringer's Solution, or Lactated Ringer's Injection. Typically, the concentration of the active ingredient in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the conjugate compound, and compositions comprising the conjugate compound, can vary from patient to patient. Determining the optimal dosage will generally involve the balancing of the level of therapeutic benefit against any risk or deleterious side effects. The selected dosage level will depend on a variety of factors including, but not limited to the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the conjugate compound is administered to a human patient according to the following dosage regime: about 50 or about 75 mg, 3 or 4 times daily.

In one embodiment, the conjugate compound is administered to a human patient according to the following dosage regime: about 100 or about 125 mg, 2 times daily.

The dosage amounts described above may apply to the conjugate (including the PBD moiety and the linker to the antibody) or to the effective amount of PBD compound provided, for example the amount of compound that is releasable after cleavage of the linker.

For the prevention or treatment of disease, the appropriate dosage of an ADC of the invention will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an ADC. Other dosage regimens may be useful. The progress of this therapy is easily monitored by conventional techniques and assays.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Preparation of Antibody Drug Conjugates

Antibody drug conjugates may be prepared by several routes, employing organic chemistry reactions, conditions, and reagents known to those skilled in the art, including: (1) reaction of a nucleophilic group of an antibody with a bivalent linker reagent, to form antibody-linker intermediate Ab-L, via a covalent bond, followed by reaction with an activated drug moiety reagent; and (2) reaction of a drug moiety reagent with a linker reagent, to form drug-linker reagent D-L, via a covalent bond, followed by reaction with the nucleophilic of an antibody. Conjugation methods (1) and (2) may be employed with a variety of antibodies, and linkers to prepare the antibody-drug conjugates of the invention.

Nucleophilic groups on antibodies include, but are not limited to side chain thiol groups, e.g. cysteine. Thiol groups are nucleophilic and capable of reacting to form covalent bonds with electrophilic groups on linker moieties such as those of the present invention. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Trees reagent) resulting in conversion of an amine into a thiol The Subject/Patient The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

In one embodiment, the patient is a population where each patient has a tumour having $\alpha_v\beta_6$ integrin on the surface of the cell.

Synthesis

One possible synthesis route to a dimer intermediate of formula VIII is shown below:

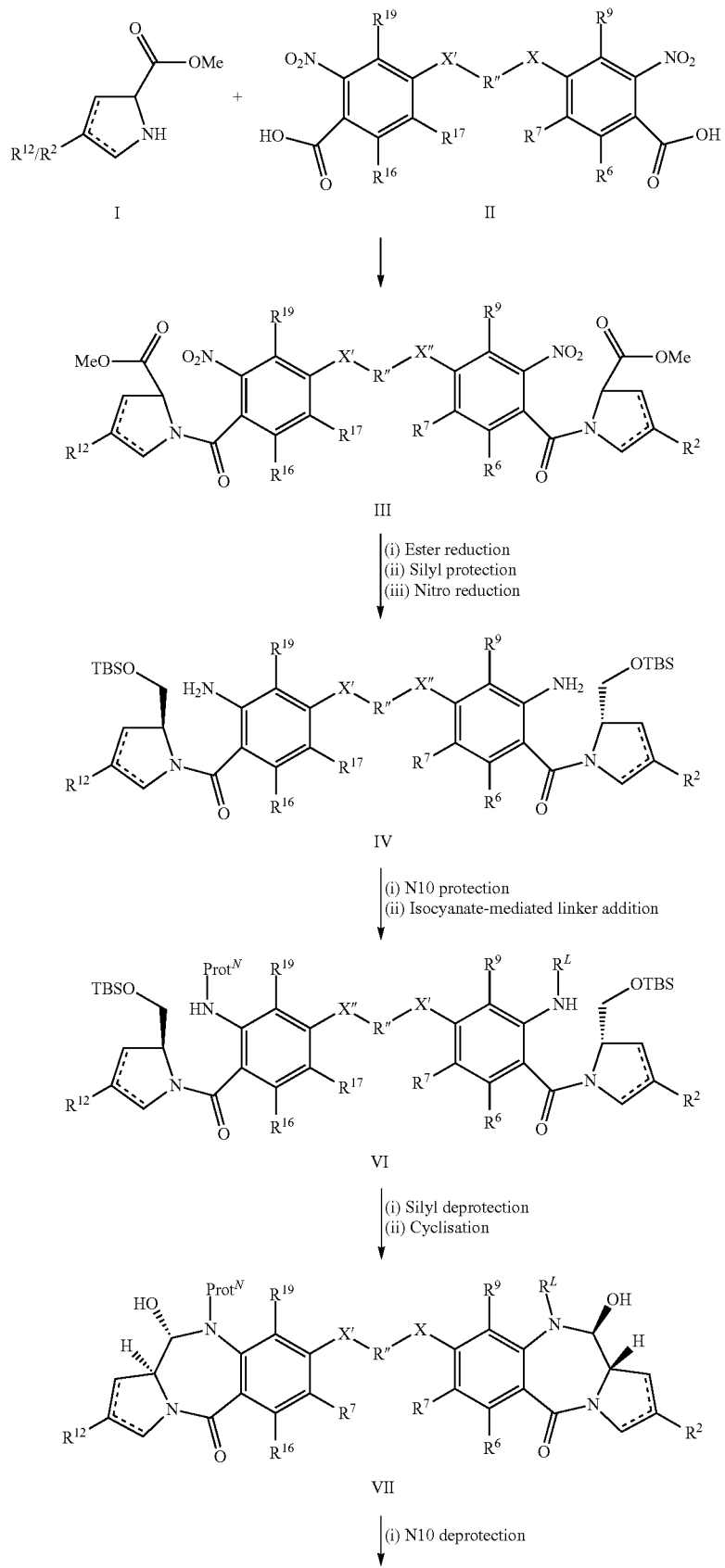

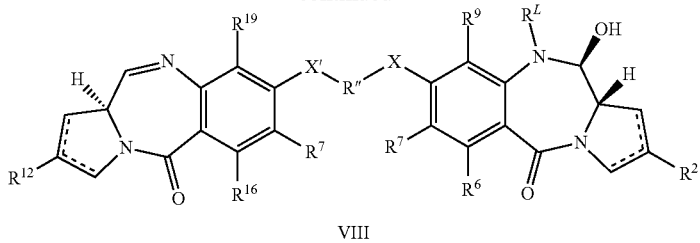

VIII

In the above scheme, $R^L$ represents:

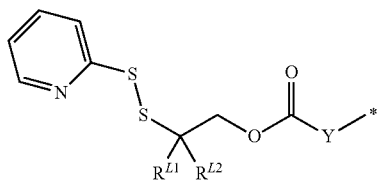

In general, unsymmetrical dimers, with respect to their N10-C11 bonds, may be prepared by treating bis-amino compounds of formula IV with one equivalent of a commercially available (or readily prepared) chloroformate reagent in order to break the symmetry of the molecules. The remaining free amine can then be functionalised independently to introduce the linking group precursor ($R^L$). Further functional group manipulation to close the PBD B-ring, remove protecting groups affords the target molecule.

Compounds of formula IV are typically prepared by coupling a suitably functionalised C-ring fragment (I) to an A-ring containing dimer core of formula II. C-ring fragments may be prepared from known carbamate protected methyl 4-oxoprolinate building blocks. Olefination under Wittig or Horner-Emmons conditions can be employed to furnish endo- or exo-unsaturated alkenes. C-ring and A-ring fragments can be coupled under standard conditions in the presence of triethylamine, using acid chloride derivatives of the A-ring fragments to give molecules of formula III. Symmetry may also be broken at this stage by introducing different C-rings. Compounds of type III can be reduced, without affecting endo or exo C-ring unsaturation, with zinc in acetic or formic acid to afford molecules of formula IV.

Alternatively, a suitable 4-hydroxy pyrrolidine building block may be coupled to a dimer core of formula II. The hydroxyl groups can be oxidized to ketones and then converted to enol triflates. Suzuki coupling can be used to introduce the pro C2 substituents (e.g. aryl, alkenyl etc). The nitro groups can then be reduced to amines, one amine is protected leaving the other free to bear the linker group.

Unsymmetrical carbamates of type VI can be prepared by treating bis-amines of type IV with a single equivalent of a commercially available (or readily prepared) chloroformates in the presence of pyridine or triethylamine. Chloroformates may be selected to afford appropriate carbamate based nitrogen protecting groups ($Prot^N$) which are orthogonal to those used in the pro-linker group ($R^L$). The $R^L$ carbamate may be introduced by converting the remaining amino group to an isocyanate and quenching it with the $R^L$ alcohol. Alternatively the $R^L$ alcohol can be converted to a chloroformate or functional equivalent (fluoroformate, p-nitrocarbonate, pentafluorocarbonate or hydroxybenzotriazole carbonate). Finally, the remaining amino group can be converted to a reactive p-nitrocarbamate, pentafluorocarbamate or hydroxybenzotriazole carbamate which can be displaced with the $R^L$ alcohol to afford molecules of formula VI.

Molecules of formula VII can be prepared from molecules of formula VI by removing the silyl protecting groups, with, for example, aqueous acetic acid. Oxidation with Dess-Martin periodinane (or alternatively TPAP/NMO, PDC or under Swern conditions) affords the ring closed product.

Conjugates of formula V may be prepared from molecules of formula VII by removal of the carbamate based nitrogen protection group.

In another embodiment, a conjugate of formula XVIII may be prepared from compound IX as shown in Scheme 2. Compound II The synthesis of compounds of formula (II) is described in the applicants earlier application, WO 2006/111759 and is also described by Gregson et al. (J. Med. Chem., 2001, 44, 1161-1174). The preparation of compound (II) as described therein is specifically incorporated by reference herein.

Reference is also made to the known methods of synthesising PBD dimers, including those reviewed in Antonow, D. and Thurston, D. E., Chem. Rev. 2011 111 (4), 2815-2864.

Further relevant disclosure may be found in WO 2010/091150. The intermediate compounds described in WO 2010/091150 may also be employed in the methods described above.

For example, the dimer compound (15) shown in paragraph [164] may be used as compound (III) in Scheme I above. This and further adaptations, would be apparent to one of skill in the art.

EXAMPLES

General Experimental Methods

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1H$ and $^{13}C$ NMR spectra were acquired at 300 K using a Bruker Avance NMR spectrometer at 400 and 100 MHz, respectively. Chemical shifts are reported relative to TMS ($\delta$=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA, Waters Micromass ZQ parameters used were: Capillary (kV), 3.38 Cone (V), 35, Extractor (V), 3.0; Source temperature (° C.), 100; Desolvation Temperature (° C.), Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, $F_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

General LC/MS conditions: The HPLC (Waters Alliance 2695) was run using a mobile phase of water (A) (formic acid 0.1%) and acetonitrile (B) (formic acid 0.1%). Gradient initial composition 5% B over to min then 5% B to 95% B within 3 min. The composition was held for 0.5 min at 95% B, and then returned to 5% B in 0.3 minutes. Total gradient run time equals 5 min. Flow rate 3.0 mL/min. 400 μL was split via a zero dead volume tee piece which passes into the mass spectrometer. Wavelength detection range: 220 to 400 nm. Function type: diode array (535 scans). Column: Phenomenex Onyx Monolithic C18 50×4.60 mm Example 1

(a) (S)-2-(methoxycarbonyl)-4-methylenepyrrolidinium chloride (3)

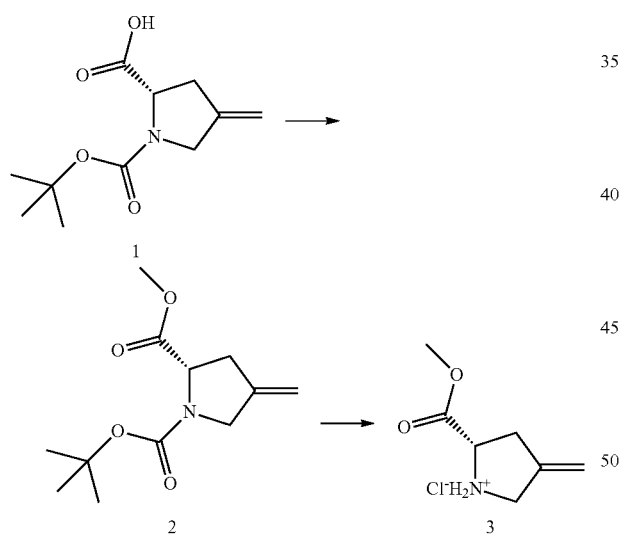

(i) (S)-1-tert-butyl 2-methyl 4-methylenepyrrolidine-1,2-dicarboxylate (2)

Potassium carbonate (19.92 g, 14 mmol, 3 eq.) was added to a stirred solution of the carboxylic acid (1) (10.92 g, 48 mmol, 1 eq.) in DMF (270 mL). The resulting white suspension was stirred at room temperature for 30 minutes, at which point iodomethane (21.48 g, 9.5 mL, 151 mmol, 3.15 eq.) was added. The reaction mixture was allowed to stir at room temperature for 3 days. The DMF was removed by rotary evaporation under reduced pressure to afford a yellow residue which was partitioned between ethylacetate and water. The organic layer was separated and the aqueous phase was extracted with ethylacetate. The combined organic layers were washed with water, brine and dried over magnesium sulphate. The ethylacetate was removed by rotary evaporation under reduced pressure to give the crude product as a yellow oil. The crude product was purified by flash chromatography [85% n-hexane/15% ethylacetate] to afford the product as a colorless oil. (Known compound F Manfré et al., *J. Org. Chem.* 1992, 57, 2060-2065)

(ii) (S)-2-(methoxycarbonyl)-4-methylenepyrrolidinium chloride (3)

A solution of 4 M hydrochloric acid in dioxane (63 mL, 254.4 mmol, 4.5 eq.) was added to the Boc protected C-ring fragment (2) (13.67 g, 56.6 mmol, 1 eq.) at room temperature. Effervescence was observed indicating liberation of $CO_2$ and removal of the Boc group. The product precipitated as a white solid and additional dioxane was added to facilitate stirring. The reaction mixture was allowed to stir for an hour and then diluted with ether. The precipitated product was collected by vacuum filtration and washed with additional ether. Air drying afforded the desired product as a white powder (9.42 g, 94%) (P Herdwijn et al., *Canadian Journal of Chemistry.* 1982, 60, 2903-7)

(b) tert-butyl (5-((5-(5-amino-4-((S)-2-(((tert-butyldimethylsilyl)oxy)methyl)-4-methylenepyrrolidine-1-carbonyl)-2-methoxyphenoxy)pentyl)oxy)-2-((S)-2-((tert-butyldimethylsilyl)oxy)methyl)-4-methylenepyrrolidine-1-carbonyl)-4-methoxyphenyl) carbamate (9)

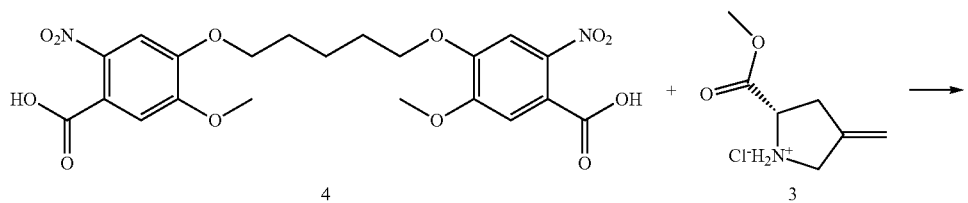

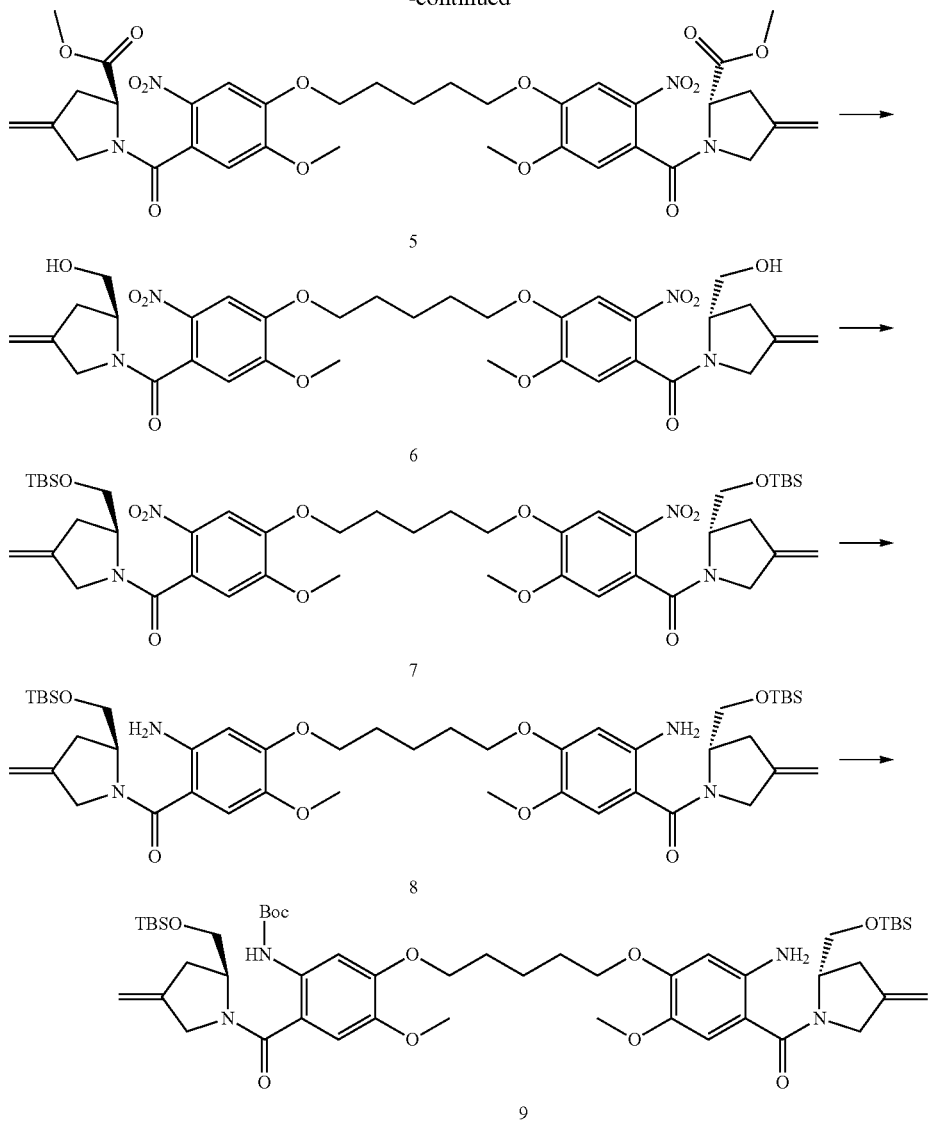

(i) (S)-(4,4'-(pentane-1,5-diylbis(oxy))bis(5-methoxy-2-nitro-4,1-phenylene))bis(((S)-2-(methoxycarbonyl)-4-methylenepyrrolidin-1-yl)methanone) (5)

A catalytic amount of anhydrous DMF (0.5 mL) was added to a stirred suspension of oxalyl chloride (9.1 g, 6.25 mL, 71.7 mmol, 3 eq.) and dimer core (4) (11.82 g, 23.9 mmol, 1 eq.) in anhydrous DCM (180 mL) at room temperature. Vigorous effervescence was observed after the addition of DMF and the reaction mixture was allowed to stir for 18 h in a round bottom flask fitted with a calcium chloride drying tube. The resulting clear solution was evaporated under reduced pressure and the solid triturated with ether. The solid product was collected by vacuum filtration, washed with additional ether and dried in vacuo at 40° C. for 1.5 hours. This solid was then added portion wise to a suspension of the C-ring (3) (9.35 g, 52.6 mmol, 2.2 eq.) in TEA (12.08 g, 119.6 mmol, 5 eq.) and dry DCM (110 mL), maintaining the temperature between −40 and −50° C. with the aid of a dry ice/acetonitrile bath. The reaction mixture was allowed to stir at −40° C. for 1 hour and then allowed to warm to room temperature at which point LCMS indicated the complete consumption of the starting material. The reaction mixture was diluted with additional DCM and washed sequentially with aqueous hydrochloric acid (1M, 2×200 mL), saturated aqueous sodium bicarbonate (2×250 mL), water (250 mL), brine (250 mL) dried (MgSO$_4$). DCM was removed by rotary evaporation under reduced pressure to afford the product as a yellow foam (13.94 g, 79%). Analytical Data: RT 3.95 min: MS (ES$^+$) m/z (relative intensity) 741 ([M+1]$^+$, 100).

(ii) (S)-(4,4'-(pentane-1,5-diylbis(oxy))bis(5-methoxy-2-nitro-4,1-phenylene))bis(((S)-2-(hydroxymethyl)-4-methylenepyrrolidin-1-yl)methanone) (6)

Solid lithium borohydride (0.093 g, 4.3 mmol, 3 eq.) was added in one portion to a solution of the ester (5) (1.05 g, 142 mmol, 1 eq.) in dry THF (10 mL) under a nitrogen atmosphere at 0° C. (ice bath). The reaction mixture was allowed to stir at 0° C. for 30 minutes and then allowed to warm to room temperature at which point precipitation of an orange gum was observed. The reaction mixture was allowed to stir at room temperature for a further 2 hours and then cooled in an ice bath and treated with water (20 mL) to give a yellow suspension. Hydrochloric acid (1M) was carefully added (vigorous effervescence!) until effervescence ceased. The reaction mixture was extracted with ethylacetate (4×50 mL) and the combined organic layers were washed with water (100 mL), brine (100 mL) and dried (MgSO$_4$). Ethylacetate was removed by rotary evaporation under reduced pressure to yield the product as a yellow foam (0.96 g, 99%). The reaction was repeated on a 12.4 g scale to yield 11.06 g of product (96%). Analytical Data: RT 3.37 min; MS (ES$^+$) m/z (relative Intensity) 685 ([M+H]$^+$, 100).

(iii) (S)-((pentane-1,5-diylbis(oxy))bis(5-methoxy-2-nitro-4,1-phenylene))bis(((S)-2-(((tert-butyldimethylsilyl)oxy)methyl)-4-methylenepyrrolidin-1-yl)methanone) (7)

A solution of bis-nitro alcohol (6) (7.94 g, 11.6 mmol, 1 eq), tert-butyldimethylsilylchloride (4.54 g, 30.15 mmol, 2.6 eq) and imidazole (4.1 g, 60.3 mmol, 5.2 eq) in anhydrous DMF (100 mL) under an argon atmosphere was stirred at room temperature for 3 hours. The reaction mixture was diluted with water (250 mL) and extracted with DCM (4×100 mL). The combined extracts were washed with water (200 mL), saturated brine (200 mL), dried (MgSO$_1$) and evaporated under reduced pressure. The residue was purified by flash column chromatography [50% ethylacetate/50% n-hexane to 100% ethylacetate in 10% increments] to afford the product as a yellow foam (10.0 g, 94%). Analytical Data: RT 4.57 min; MS (ES$^+$) m/z (relative intensity) 913 ([M+H]$^+$, 100).

(iv) (S)-((pentane-1,5-diylbis(oxy))bis(2-amino-5-methoxy-4,1-phenylene))bis(((S)-2-(tert-butyldimethylsilyl)oxy)methyl)-4-methylenepyrrolidin-1-yl)methanone) (8)

Formic acid solution (5% v/v, 15 mL) was added in one portion to a mixture of zinc powder (29.56 g, 0.45 mol, 40 eq.) and compound (7) (10.34 g, 11.32 mmol, 1 eq.) in ethylacetate/ethanol (80 mL/150 mL). An exotherm of 12° C. was observed. After 15 minutes the reaction mixture was filtered through celite washing with ethylacetate (excess). The filtrate was washed with saturated sodium bicarbonate (3×150 mL), water (200 mL), saturate brine (200 mL), dried (MgSO$_4$) and evaporated under reduced pressure. Purification by flash column chromatography [ethylacetate] gave the product as a white foam (8.09 g, 84%). Analytical Data: RT 4.43 min; MS (ES$^+$) m/z (relative intensity) 853 ([M+H]$^+$, 100).

(v) tert-butyl (5-((5-(5-amino-4-((S)-2-(((tert-butyldimethylsilyl)oxy)methyl)-4-methylenepyrrolidine-1-carbonyl)-2-methoxyphenoxy)pentyl)oxy)-2-((S)-2-(((tert-butyldimethylsilyl)oxy)methyl)-4-methylenepyrrolidine-1-carbonyl)-4-methoxyphenyl)carbamate (9)

A solution of the bis-aniline (8) (6.02 g, 7.1 mmol, 1 eq.) and di-t-butyl-dicarbonate (1.54 g, 7.1 mmol, 1 eq.) in anhydrous THF (50 mL) was heated at reflux for 16 hours. The solvent was evaporated under reduced pressure and the residue was purified by flash column chromatography [40% ethylacetate/60% n-hexane to 60% ethylacetate/40% n-hexane to 100% ethylacetate] to give the product as a white foam (3.22 g, 48%). Analytical Data: RT 4.27 min MS (ES$^+$) m/z (relative intensity) 953 ([M+H]$^+$, 100), MS (ES$^-$) m/z (relative intensity) 951 ([M−H]$^-$, 100).

(c) (11S,11aS)-2-(pyridin-2-yldisulfanyl)ethyl 11-hydroxy-7-methoxy-8-((5-(((S)-7-methoxy-2-methylene-5-oxo-2,3,5,11a-tetrahydro-1H-pyrrolo[2,1-c][1,4]benzodiazepin-8-yl)oxy)pentyl)oxy)-2-methylene-5-oxo-2,3,11,11a-tetrahydro-1H-pyrrolo[2,1-c][1,4]benzodiazepine-10(5H)-carboxylate (14)

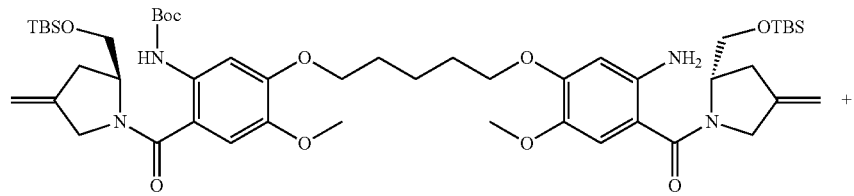

9

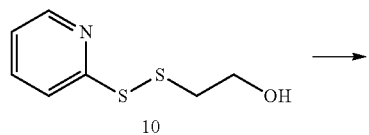

10

-continued
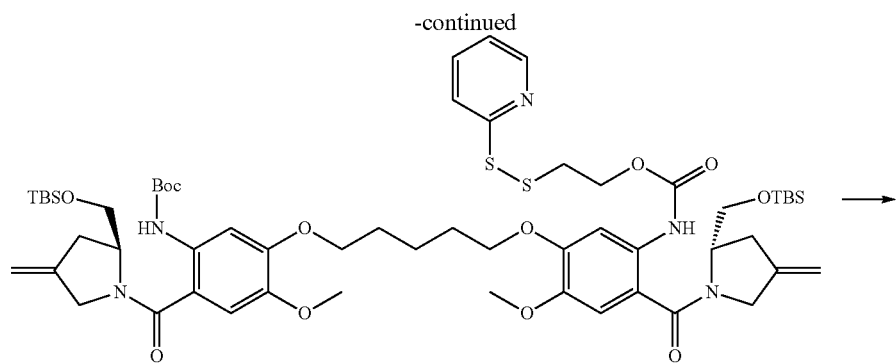
11
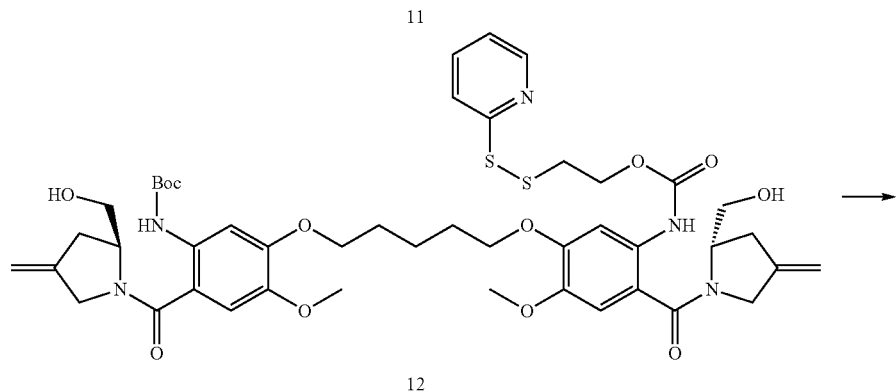
12
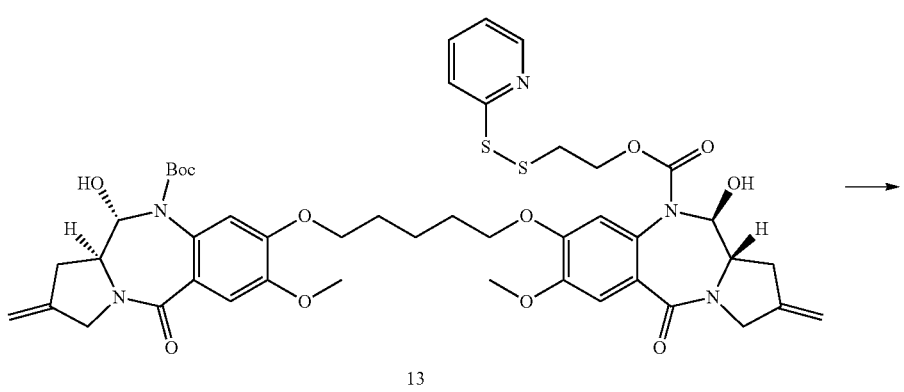
13
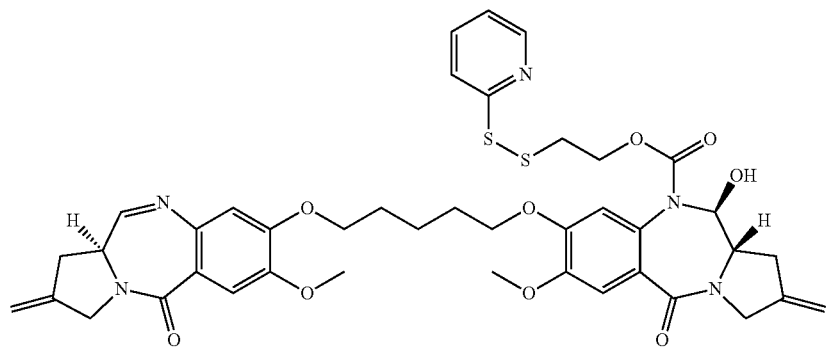
14
Compound 10 was prepared according to Jones et al, J. Am. Chem. Soc., 2006, 128, 6526-6527.

(i) tert-butyl (2-(pyridin-2-yldisulfanyl)ethyl) ((S)-(pentane-1,5-diylbis(oxy))bis(2-((S)-2-(((tert-butyldimethylsilyl)oxy)methyl)-4-methylenepyrrolidine-1-carbonyl)-4-methoxy-5,1-phenylene))dicarbamate (11)

Triethylamine (0.25 g, 0.34 mL, 2.42 mmol, 2.2 eq.) was added to a stirred solution of the mono-Boc protected bis-aniline (9) (1.05 g, 1.1 mmol, 1.0 eq.) and triphosgene (0.117 g, 0.4 mmol, 0.36 eq.) in dry THF (10 mL) under an argon atmosphere at room temperature. The reaction mixture was heated to 40° C. and after 5 minutes a sample was treated with methanol and analysed by LCMS as the methyl carbamate. Analytical Data: RT 4.37 min MS (ES$^+$) m/z (relative intensity) 1011 ([M+H]$^+$, 100).

A solution of 2-(pyridin-2-yldisulfanyl)ethanol (10) (0.31 g, 1.65 mmol, 1.5 eq.) and triethylamine (0.17 g, 0.23 mL, 1.65 mmol, 1.5 eq.) in dry THF (10 mL) was added drop wise to the freshly prepared isocyanate. The reaction mixture was heated at 40° C. for 1.5 h after which time a further portion of triphosgene (0.058 g, 0.2 mmol, 0.18 eq.) was added. After a further 30 min the reaction mixture was allowed to cool, filtered to remove triethylamine hydrochloride and the filtrate was evaporated to dryness to afford the crude product as a yellow oil which was purified by flash column chromatography [60% n-hexane/40% ethylacetate changing to 55% n-hexane/45% ethylacetate] to give the desired product as a colourless oil (0.63 g, 49%). Analytical Data: RT 4.50 trim MS (ES$^+$) m/z (relative intensity) 1166 ([M+H]$^+$, 100), MS (ES$^-$) m/z (relative intensity) 1164 ([M−H])$^-$, 70).

(ii) tert-butyl (2-(pyridin-2-yldisulfanyl)ethyl) ((S)-(pentane-1,5-diylbis(oxy))bis(2-((S)-2-(hydroxymethyl)-4-methylenepyrrolidine-1-carbonyl)-4-methoxy-5,1-phenylene))dicarbamate (12)

AcOH/H$_2$O (3/1/) (8 mL) was added to a solution of compound (11) (0.37 g, 0.32 mmol, 1 eq) in THF (2 mL) and the resultant solution was stirred at room temperature for 18 h. The pH of the reaction mixture was adjusted to pH8 with saturated NaHCO$_3$ solution. The mixture was extracted with ethylacetate (3×100 mL) and the combined extracts were washed with saturated NaHCO$_3$ solution (100 mL), water (100 mL), saturated brine (100 mL), dried (MgSO$_4$ and evaporated under reduced pressure. Purification of the residue by flash column chromatography [gradient elution chloroform/methanol 0% to 5% in 1% increments] gave the product as a white foam (0.24 g, 81%). Analytical Data: RT 3.08 min; MS (ES$^+$) m/z (relative intensity) 938 ([M+H])$^+$, 100), MS (ES$^-$) m/z (relative intensity) 936 ([M−H])$^-$, 100).

(iii) (11S,11aS)-tert-butyl 11-hydroxy-8-((5-(((11S,11aS)-11-hydroxy-7-methoxy-2-methylene-5-oxo-10-((2-(pyridin-2-yldisulfanyl)ethoxy)carbonyl)-2,3,5,10,11,11a-hexahydro-1H-pyrrolo[2,1-c][1,4]-benzodiazepin-8-yl)oxy)pentyl)oxy)-7-methoxy-2-methylene-5-oxo-2,3,11,11a-tetrahydro-1H-pyrrolo[2,1-c][1,4]-benzodiazepine-10(5H)-carboxylate (13)

A solution of DMSO (79 mg, 72 μL, 1.0 mmol, 4.4 eq) in DCM (5 mL) was added dropwise to a solution of oxalyl chloride (62 mg, 42 μL, 0.49 mmol, 2.15 eq.) in DCM (5 mL) under an argon atmosphere at −78° C. (dry ice/acetone). The solution was stirred at −78° C. for 15 minutes. A solution of compound (12) (0.214 g, 0.23 mmol, 1.0 eq.) in DCM (6 mL) was added dropwise and the mixture was stirred at −78° C. for 45 minutes. Triethylamine (0.23 g, 0.32 mL, 2.28 mmol, 10 eq.) was added and after 5 min the reaction mixture was allowed to reach room temperature. The reaction mixture was treated with saturated NH$_4$Cl solution (15 mL), the organic portion was separated and washed with 1M citric acid solution (3×50 mL), saturated NaHCO$_3$ solution (100 mL), water (100 mL), saturated brine (100 mL), dried (MgSO$_4$) and evaporated under reduced pressure to give a pale yellow oil. Purification by flash column chromatography gave the product as a white foam (68 mg, 32%). Analytical Data: RT 2.90 mm MS (ES$^+$) m/z (relative intensity) 933 ([M+H]$^+$, 50), MS (ES) m/z (relative intensity) 935 ([M−H])$^-$, 55).

(iv) (11S,11aS)-2-(pyridin-2-yldisulfanyl)ethyl 11-hydroxy-7-methoxy-8-((5-(((S)-7-methoxy-2-methylene-5-oxo-2,3,5,11a-tetrahydro-1H-pyrrolo[2,1-c][1,4]benzodiazepin-8-yl)oxy)pentyl)oxy)-2-methylene-5-oxo-2,3,11,11a-tetrahydro-1H-pyrrolo[2,1-c][1,4]benzodiazepine-10(5H)-carboxylate (14)

A cold (ice bath) solution of 95% trifluoroacetic acid (1 mL) was added to compound 13 which had been cooled in an ice bath. The solution was stirred at 0° C. for 15 minutes when it was shown to be complete by LCMS. The reaction mixture was added dropwise to a mixture of ice and saturated NaHCO$_3$ solution to neutralise the trifluoroacetic acid solution. The mixture was extracted with DCM (4×50 mL) and the combined extracts were washed with saturated brine (100 mL), dried (MgSO$_4$) and evaporated under reduced pressure to give the product as a white foam (26 mg, 96%). Analytical Data: RT 2.72 min; MS (ES$^+$) m/z (relative intensity) 816 ([M+H]$^+$, 70), MS (ES$^-$) m/z (relative intensity) 814 ([M−H])$^-$, 40).

Example 2

(a) (R)-2-(pyridin-2-yldisulfanyl)propan-1-ol (18)

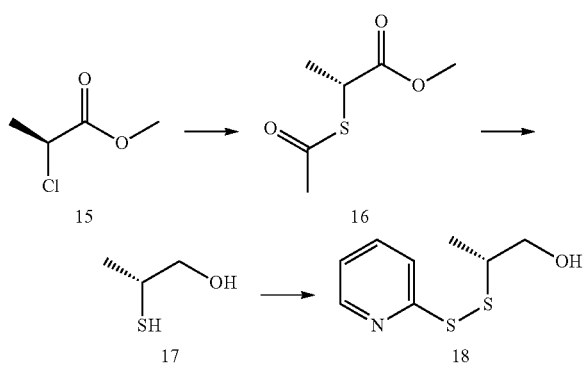

(i) (R)-methyl 2-(acetylthio)propanoate (16)

Thioacetic acid (1.99 g, 1.86 mL, 26.1 mmol, 1.1 eq.) was added to a suspension of cesium carbonate (7.73 g, 23.72 mmol, 1.0 eq.) in dry DMF (40 mL). After 30 minutes (S)-methyl 2-chloropropanoate (16) was added and the mixture was allowed to stir at room temperature for 1 hour. The reaction mixture was partitioned between diethyl ether (150 mL) and water (150 mL); the water was separated and washed with a further portion of diethyl ether (150 mL). The combined organic portions were washed with water (6×100 mL), brine (200 mL), dried (MgSO₄) and evaporated under reduced pressure. Purification by flash column chromatography [10% ethylacetate/90% n-hexane] gave the product as a colourless oil (3.01 g, 82%). Analytical Data: RT 2.25 min; MS (ES⁺) m/z (relative intensity) 163 ([M+H]⁺, 10), 185 ([M+Na]⁺, 65); $[α]^t_d=[+141]^{17.8° C.}_d$ (c, 2.26 CHCl₃).

(ii) (R)-2-mercaptopropan-1-ol (17)

A solution of thioacetate (16) (0.57 g, 3.54 mmol, 1.0 eq.) in dry THF (10 was added drop wise to a suspension of lithium aluminium hydride (0.54 g, 14.15 mmol, 4.0 eq.) in dry THF (20 mL) at reflux under an argon atmosphere. After 1 h the reaction mixture was cooled to 0° C. and 2M HCl was added drop wise maintaining the temperature below 30° C. until effervescence ceased. The resultant mixture was allowed to stir at room temperature for 1 hour then filtered through celite washing with THF (40 mL). The solvent was evaporated the residue was re-dissolved in DCM and dried (MgSO₄). Evaporation of the DCM under reduced pressure followed by column chromatography of the residue [60% n-hexane/40% ethylacetate] gave the product as a pale yellow oil (0.193 g, 58%). Analytical Data: $[α]^t_d=[-22]^{17.2° C.}_d$ (c, 0.972 CHCl₃).

(iii) (R)-2-(pyridin-2-yldisulfanyl)propan-1-ol (18)

Sulfuryl chloride (1M in DCM, 2.0 mL, 2.0 mmol, 1.1 eq.) was added drop wise to a solution of 2-mercaptopyridine (0.2 g, 1.81 mmol, 1.0 eq.) in dry DCM (5 mL) at 0° C. under an argon atmosphere. The resultant solution was stirred at room temperature for 2 hours and the DCM was evaporated under reduced pressure to give a yellow solid. The solid was suspended in dry DCM (10 mL) and a solution of (R)-2-mercaptopropan-1-ol (17) (0.18 g, 1.95 mmol, 1.08 eq.) in dry DCM (5 mL) was added drop wise. The mixture was stirred at room temperature for 18 hours under an argon atmosphere. The reaction mixture was filtered and the filtrate was evaporated under reduced pressure to give a yellow gum. The gum was re-dissolved in water and the solution was basified with ammonium hydroxide solution, extracted with DCM (3×50 mL) and the combined extracts were washed with water (100 mL), brine (100 dried (MgSO₄) and evaporated to give a yellow oil. Purification by flash column chromatography [80% n-hexane/20% ethylacetate to 60% n-hexane/40% ethylacetate in 5% increments] gave the product as a colourless oil (0.213 g, 59%). Analytical Data: RT 2.43 min; MS (ES⁻) m/z (relative intensity) 202 ([M+H]⁺, 50); $[α]^t_d=[+273]^{26.2° C.}_d$ (c, 0.28 CHCl₃).

(b) (11S,11aS)—(R)-2-(pyridin-2-yldisulfanyl)propyl 11-hydroxy-7-methoxy-8-((5-(((S)-7-methoxy-2-methylene-5-oxo-2,3,5,11a-tetrahydro-1H-pyrrolo[2,1-c][1,4]-benzodiazepin-8-yl)oxy)pentyl)oxy)-2-methylene-5-oxo-2,3,11,11a-tetrahydro-1H-pyrrolo[2,1-c][1,4]benzodiazepine-10(5H)-carboxylate (22)

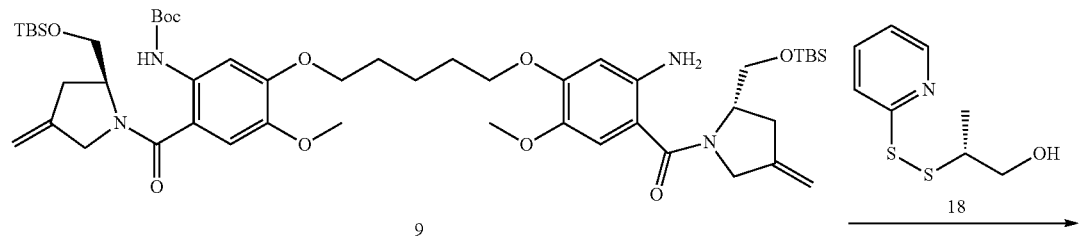

9

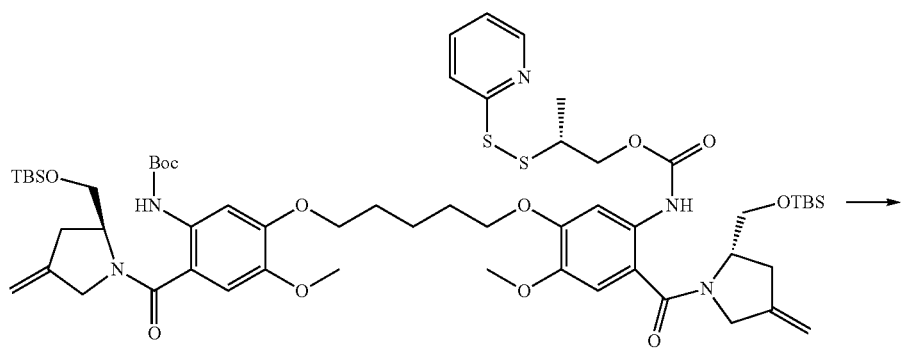

19

-continued

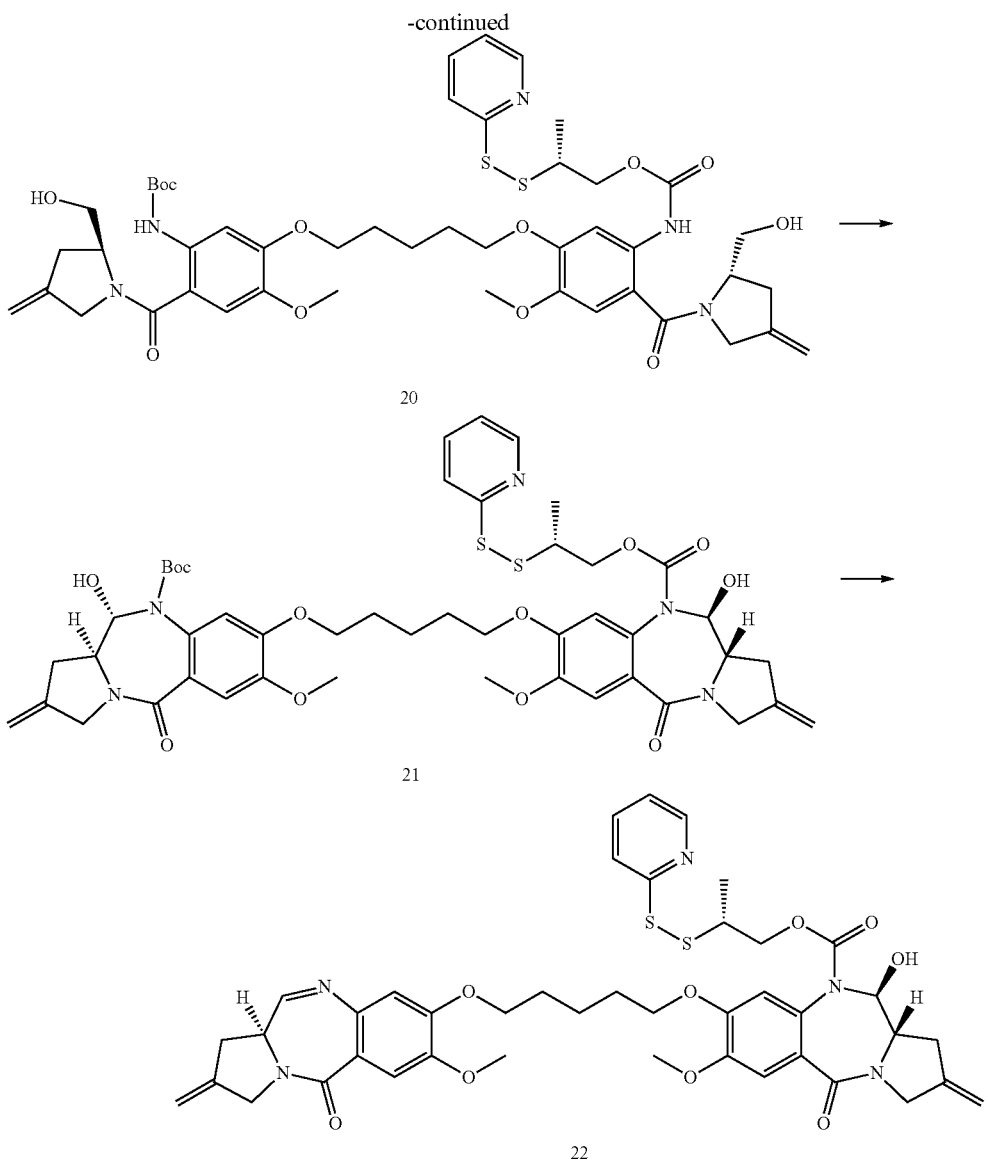

(i) tert-butyl ((R)-2-(pyridin-2-yldisulfanyl)propyl) ((S)-(pentane-1,5-diylbis(oxy))bis(2-((S)-2-(((tert-butyldimethylsilyl)oxy)methyl)-4-methylenepyrrolidine-1-carbonyl)-4-methoxy-5,1-phenylene))dicarbamate (19)

Triethylamine (0.28 g, 0.39 mL, 2.8 mmol, 2.2 eq.) was added to a stirred solution of the mono-boc protected bis-aniline (9) (1.21 g, 1.27 mmol, 1.0 eq.) and triphosgene (0136 g, 0.46 mmol, 0.36 eq.) in dry THF (15 mL) under an argon atmosphere at room temperature. The reaction mixture was heated to 40° C. and after 5 minutes a sample was treated with methanol and analysed by LCMS as the methyl carbamate. Analytical Data: RT 4.30 min MS (ES⁺) m/z (relative intensity) 1011 ([M+H]⁺, 100).

A solution of (R)-2-(pyridin-2-yldisulfanyl)propan-1-ol (18) (0.38 g, 1.91 mmol, 1.5 eq.) and triethylamine (0.19 g, 0.27 mL, 1.91 mmol, 1.5 eq.) in dry THF (10 mL) was added drop wise to the freshly prepared isocyanate. The reaction mixture was heated at 40° C. for 4 hours and then stirred at room temperature for 18 hours. The reaction mixture was filtered to remove triethylamine hydrochloride and the filtrate was evaporated to dryness to afford the crude product as a yellow oil which was purified by flash column chromatography [60% n-hexane/40% ethylacetate to 40% n-hexane/60% ethylacetate in 5% increments] to give the desired product as a white foam (0.75 g, 50%). Analytical Data: RT 4.50 min; MS (ES⁺) m/z (relative intensity) 1180 ([M+H]⁺, 60); $[\alpha]_d^t=$ $[-18]^{21° C.}_d$ (c, 0.28 CHCl₃).

(ii) tert-butyl ((R)-2-(pyridin-2-yldisulfanyl)propyl) ((S)-(pentane-1,5-diylbis(oxy))bis(2-((S)-2-(hydroxymethyl-4-methylenepyrrolidine-1-carbonyl)-4-methoxy-5,1-phenylene))dicarbamate (20)

Acetic acid/H₂O (3/1, 16 mL) was added to a solution, of the bis-silyl ether (19) (0.72 g, 0.81 mmol, 1 eq.) in THF (4 mL). The resultant solution was stirred at room temperature for 16 hours. The pH of the reaction mixture was adjusted to pH8 with saturated sodium bicarbonate solution. The mixture was extracted with ethylacetate (4×150 mL) and the combined extracts were washed with saturated sodium bicarbonate solution (2×150 mL), water (150 mL), brine (150 mL), dried (MgSO$_4$ and evaporated under reduced pressure. Purification by flash column chromatography gave the product as a white foam (0.56 g, 96%). Analytical Data: RT 3.15 min; MS (ES$^-$) m/z (relative intensity) 953 ([M+H]$^+$, 100); $[\alpha]^t_d$=[−13.5]$^{26°\ C.}_d$ (c, 0.22 CHCl$_3$).

(iii) (11S,11aS)-tert-butyl 11-hydroxy-8-((5-(((11S,11aS)-11-hydroxy-7-methoxy-2-methylene-5-oxo-10-(((R)-2-(pyridin-2-yldisulfanyl)propoxy)carbonyl)-2,3,5,10,11,11a-hexahydro-1H-pyrrolo[2,1-c][1,4]-benzodiazepin-8-yl)oxy)pentyl)oxy)-7-methoxy-2-methylene-5-oxo-2,3,11,11a-tetrahydro-1H-pyrrolo[2,1-c][1,4]-benzodiazepine-10(5H)-carboxylate (21)

A solution of DMSO 91 mg, 83 μL, 1.16 mmol, 4.4 eq.) in anhydrous DCM (5 mL) was added drop-wise to a solution of oxalyl chloride (20M in DCM, 318 μL, 0.635 mmol, 2.4 eq.) in anhydrous DCM (5 mL). at −40° C. under an argon atmosphere. The solution was stirred at −40° C. for 15 minutes. A solution of the bis-alcohol (20) (0.252 g, 0.26 mmol, 1 eq.) in anhydrous DCM (10 mL) was added drop wise and the resultant mixture stirred at −40° C. for 45 minutes. During this time the temperature was allowed to reach −25° C. The temperature was lowered to −35° C. and triethylamine (0.27 g, 0.36 mL, 2.6 mmol, 10 eq.) was added drop wise. After 5 minutes the temperature was allowed to reach room temperature. The reaction mixture was diluted with DCM (50 mL) and extracted with 1M citric acid solution (3×150 mL), saturated sodium bicarbonate solution (150 mL), water (200 mL), brine (200 mL), dried (MgSO$_4$) and evaporated under reduced pressure to give a yellow foam. Purification by flash column chromatography [chloroform/methanol 0% to 2% in 0.5% increments] gave the product as a white foam (0.137 g, 53%). Analytical Data: RT 3.17 min, MS (ES$^+$) m/z (relative intensity) 948 [M+H]$^+$, 100); $[\alpha]^t_d$=[+170]$^{26°\ C.}_d$ (c, 0.25 CHCl$_3$).

(iv) (11S,11aS)-(R)-2-(pyridin-2-yldisulfanyl)propyl 11-hydroxy-7-methoxy-8-((5-(((S)-7-methoxy-2-methylene-5-oxo-2,3,5,11a-tetrahydro-1H-pyrrolo[2,1-c][1,4]benzodiazepin-8-yl)oxy)pentyl)oxy)-2-methylene-5-oxo-2,3,11,11a-tetrahydro-1H-pyrrolo[2,1-c][1,4]-benzodiazepine-10(5H)-carboxylate (22)

A cold (ice bath) solution of 95% trifluoroacetic acid (8.5 mL) was added to compound (21) (0.221 g, 0.23 mmol, 1 eq.) which had been cooled in an ice bath. The solution was stirred at 0° C. for 25 minutes when it was shown to be complete by LCMS. The reaction mixture was added drop-wise to a mixture of ice and saturated sodium bicarbonate solution (200 mL) to neutralise the trifluoroacetic acid solution. The mixture was extracted with DCM (4×75 mL) and the combined extracts were washed with water (100 mL) saturated brine (100 mL), dried (MgSO$_4$) and evaporated under reduced pressure to give the crude product. Purification by flash column chromatography [chloroform/methanol 0% to 3% in 1% increments] gave the product as a white foam (0.192 g, 99%). Analytical Data: RT 3.00 min, MS (ES$^+$) m/z (relative intensity) 830 ([M H]$^+$, 75); $[\alpha]^t_d$=[+444]$^{22°\ C.}_d$ (c, 0.26 CHCl$_3$).

Example 3

Determination of in Vitro Cytotoxicity

K562 human chronic myeloid leukaemia cells were maintained in RPM1 1640 medium supplemented with 10% fetal calf serum and 2 mM glutamine at 37° C. in a humidified atmosphere containing 5% CO$_2$ and were incubated with a specified dose of drug for 96 hours at 37° C. in the dark. The incubation was terminated by centrifugation (5 min, 300 g) and the cells were washed once with drug-free medium. Following the appropriate drug treatment, the cells were transferred to 96-well microtiter plates (10$^4$ cells per well, 8 wells per sample). Plates were then kept in the dark at 37° C. in a humidified atmosphere containing 5% CO$_2$. The assay is based on the ability of viable cells to reduce a yellow soluble tetrazolium salt, 3-(4,5-dimethylthiazol-2-yl)-2,5-diphenyl-21-1-tetrazolium bromide (MTT, Aldrich-Sigma), to an insoluble purple formazan precipitate. Following incubation of the plates for 4 days (to allow control cells to increase in number by approximately 10 fold), 20 μL of MTT solution (5 mg/mL in phosphate-buffered saline) was added to each well and the plates further incubated for 5 hours. The plates were then centrifuged for 5 minutes at 300 g and the bulk of the medium pipetted from the cell pellet leaving 10-20 μL per well. DMSO (200 μL) was added to each well and the samples agitated to ensure complete mixing. The optical density was then read at a wavelength of 550 nm on a Titertek Multiscan ELISA plate reader, and a dose-response curve was constructed. For each curve, an IC$_{50}$ value was read as the dose required to reduce the final optical density to 50% of the control value.

Reduction/Oxidation of ThioMabs for Conjugation

Full length, cysteine engineered monoclonal antibodies (ThioMabs-Junutula, et al., 2008b Nature Biotech., 26(8): 925-932; Dornan et al (2009) Blood 114(13):2721-2729; U.S. Pat. Nos. 7,521,541; 7,723,485, WO2009/052249, Shen et al (2012) Nature Biotech., 30(2):184-191; Junutula et al (2008) Jour of Immun. Methods 332:41-52) expressed in CHO cells were reduced with about a 20-40 fold excess of TCEP (tris(2-carboxyethyl)phosphine hydrochloride or DTT (dithiothreitol) in 50 mM Tris pH 7.5 with 2 mM EDTA for 3 hrs at 37° C. or overnight at room temperature. (Getz et al (1999) Anal. Biochem. Vol 273:73-80 Soltec Ventures, Beverly, Mass.). The reduced ThioMab was diluted and loaded onto a HiTrap S column in 10 mM sodium acetate, pH 5, and eluted with PBS containing 0.3M sodium chloride. Alternatively, the antibody was acidified by addition of ¹⁄₂₀$^{th}$ volume of 10% acetic acid, diluted with 10 mM succinate pH 5, loaded onto the column and then washed with 10 column volumes of succinate buffer. The column was eluted with 50 mM Tris pH7.5, 2 mM EDTA.

The eluted reduced ThioMab was treated with 15 fold molar excess of DHAA (dehydroascorbic acid) or 200 nM aqueous copper sulfate (CuSO$_4$). Oxidation of the interchain disulfide bonds was complete in about three hours or more. Ambient air oxidation was also effective. The re-oxidized antibody was dialyzed into 20 mM sodium succinate pH 5, 150 mM NaCl, 2 mM EDTA and stored frozen at −20° C.

Conjugation of Thio-Mabs with Compounds to Prepare Antibody-Drug Conjugates

The deblocked, reoxidized, thio-antibodies (ThioMab) were reacted with 6-8 fold molar excess of the compounds above (14, 22) (from a DMSO stock at a concentration of 20 mM) in 50 mM Tris, pH 8, until the reaction was complete (16-24 hours) as determined by LC-MS analysis of the reaction mixture.

The crude antibody-drug conjugates (ADC) were then applied to a cation exchange column after dilution with 20 mM sodium succinate, pH 5. The column was washed with at least 10 column volumes of 20 mM sodium succinate, pH 5, and the antibody was eluted with PBS. The antibody drug conjugates were formulated into 20 mM His/acetate, pH 5, with 240 mM sucrose using gel filtration columns. The antibody-drug conjugates were characterized by UV spectroscopy to determine protein concentration, analytical SEC (size-exclusion chromatography) for aggregation analysis and LC-MS before and after treatment with Lysine C endopeptidase.

Size exclusion chromatography was performed using a Shodex KW802.5 column in 0.2M potassium phosphate pH 6.2 with 0.25 mM potassium chloride and 15% IPA at a flow rate of 0.75 ml/min. Aggregation state of the conjugate was determined by integration of eluted peak area absorbance at 280 nm.

LC-MS analysis was performed using an Agilent QTOF 6520 ESI instrument. As an example, and an antibody-drug conjugate generated using this chemistry was treated with 1:500 w/w Endoproteinase Lys C (Promega) in Tris, pH 7.5, for 30 min at 37° C. The resulting cleavage fragments were loaded onto a 1000A, 8 um PLRP-S column heated to 80° C. and eluted with a gradient of 30% B to 40% B in 5 minutes. Mobile phase A was $H_2O$ with 0.05% TFA and mobile phase B was acetonitrile with 0.04% TFA. The flow rate was 0.5 ml/min. Protein elution was monitored by UV absorbance detection at 280 nm prior to electrospray ionization and MS analysis. Chromatographic resolution of the unconjugated Fc fragment, residual unconjugated Fab and drugged Fab was usually achieved. The obtained m/z spectra were deconvoluted using Mass Hunter™ software (Agilent Technologies) to calculate the mass of the antibody fragments.

As an example, the molecular weight (MW) for thio-Tmab conjugated with 22 (mass addition=720 daltons). Observed deconvoluted masses:

53,296 daltons corresponds to MW of unconjugated Fc fragment 47,431 daltons corresponds to MW of unconjugated Fab fragment 48,150 daltons corresponds to MW of drugged Fab fragment Thus the observed peak at 48,150 daltons corresponds to the expected Fab fragment (47,431 daltons) bearing one drug 22 (+720 daltons).

ADC Thio-Conjugates with 22

Mass addition 719.84

| Ab | ADC | DAR (drug to antibody ratio) | Observed mass | | | |
|---|---|---|---|---|---|---|
| | | | naked Ab | +2 drugs | naked Fab | Fab + 1 drug |
| Tmab | 101 | 1.6 | 148121 | 149580 | 47431 | 48150 |
| Tmab | 102 | 1.8 | 148122 | 149580 | 47431 | 48150 |
| xCD22 | 103 | 1.8 | 149415 | 150851 | 48075 | 48794 |
| Tmab | 104 | 1.9 | 148122 | 149571 | 47431 | 48150 |
| GFRA1 | 105 | 1.8 | 148916 | 150360 | 47828 | 48546 |
| xGD | 106 | 1.8 | 149706 | 151142 | 48220 | 48939 |

ADC Thio-Conjugates with 14

Mass addition 705.81

| Ab | ADC | DAR | Observed mass | | | |
|---|---|---|---|---|---|---|
| | | | naked Ab | +2 drugs | naked Fab | Fab + 1 drug |
| Tmab | 110 | 1.7 | 148121 | 149580 | 47432 | 48136 |
| Tmab | 111 | 1.8 | 148122 | 149580 | 47432 | 48135 |
| xCD22 | 112 | 1.7 | 149410 | 150867 | 48074 | 48795 |

The following in vitro and in vivo assays are also described in Phillips et al (2008) Cancer Res. 68(22):9280-9290.

In Vitro Cell Proliferation Assay

Efficacy of ADC were measured by a cell proliferation assay employing the following protocol (CellTiter Glo Luminescent Cell Viability Assay, Promega Corp. Technical Bulletin TB288; Mendoza et al (2002) Cancer Res. 62:5485-5488). All cell lines were obtained from American Type Culture Collection:

1. An aliquot of 100 µl of cell culture containing about $10^4$ cells (for example, KPL-4, a human breast cancer cell line, Kurebayashi et al (1999) Brit. Jour. Cancer 79(5-6):707-717), SKBR-3, or MCF7) in medium was deposited in each well of a 96-well, opaque-walled plate.

2. Control wells were prepared containing medium and without cells.

3. ADC was added to the experimental wells and incubated for 3-5 days.

4. The plates were equilibrated to room temperature for approximately 30 minutes.

5. A volume of CellTiter-Glo Reagent equal to the volume of cell culture medium present in each well was added.

6. The contents were mixed for 2 minutes on an orbital shaker to induce cell lysis.

7. The plate was incubated at room temperature for 10 minutes to stabilize the luminescence signal.

8. Luminescence was recorded and reported in graphs as RLU=relative luminescence units.

Certain cells are seeded at 1000-2000/well or 2000-3000/well in a 96-well plate, 50 uL/well. After one or two days, ADC are added in 50 µL volumes to final concentration of 9000, 3000, 1000, 333, 111, 37, 12.4, 4.1, or 1.4 ng/mL, with "no ADC" control wells receiving medium alone. Conditions are in duplicate or triplicate After 3-5 days, 100 µL/well Cell TiterGlo II is added (luciferase-based assay; proliferation measured by ATP levels) and cell counts are determined using a luminometer. Data are plotted as the mean of luminescence for each set of replicates, with standard deviation error bars. The protocol is a modification of the CellTiter Glo Luminescent Cell Viability Assay (Promega):

1. Plate 1000 cells/well in 50 µL/well of FBS/glutamine media. Allow cells to attach overnight.

2. ADC is serially diluted 1:3 in media beginning et al working concentration 18 µg/ml (this results in a final concentration of 9 µg/ml). 50 µL of diluted ADC is added to the 50 µL of cells and media already in the well.

3. Incubate 72-96 hrs (the standard is 72 hours, but watch the 0 ug/mL concentration to stop assay when the cells are 85-95% confluent).

4. Add 100 µL/well of Promega Cell Titer Glo reagent, shake 3 min. and read on luminometer Results Antibody-drug conjugates, trastuzumab-14 (110) and trastuzumab-22 (101) were tested against SK-BR-3, KPL-4, and MCF-7 (Levenson et al (1997) *Cancer Res.* 57(15): 3071-3078) cells to measure in vitro cell viability in five day studies. The $IC_{50}$ (µg/mL) value for 101 against SK-BR-3 was 22.12. The $IC_{50}$ value for 110 against SK-BR-3 was 102.78. are SK-BR-3 cells are HER2+ expressing, trastuzumab sensitive. Both 101 and 110 were effectively inactive against MCF-7, which is a HER2 non-expressing human breast adenocarcinoma cell line. Thus, conjugates 101 and 110 demonstrate targetted cell killing potency.

Tumor Growth Inhibition, In Vivo Efficacy in High Expressing HER2 Transgenic Explant Mice Animals suitable for transgenic experiments can be obtained from standard commercial sources such as Taconic (Germantown, N.Y.). Many strains are suitable, but FVB female mice are preferred because of their higher susceptibility to tumor formation. FVB males were used for mating and vasectomized CD.1 studs were used to stimulate pseudopregnancy. Vasectomized mice can be obtained from any commercial supplier. Founders were bred with either FVB mice or with 129/BL6×FVB p53 heterozygous mice. The mice with heterozygosity at p53 allele were used to potentially increase tumor formation. However, this has proven unnecessary. Therefore, some F1 tumors are of mixed strain. Founder tumors are FVB only. Six founders were obtained with some developing tumors without having litters.

Animals having tumors (allograft propagated from Fo5 mmtv transgenic mice) were treated with a single or multiple dose by IV injection of ADC. Tumor volume was assessed at various time points after injection.

Tumors arise readily in transgenic mice that express a mutationally activated form of neu, the rat homolog of HER2, but the HER2 that is overexpressed in human breast cancers is not mutated and tumor formation is much less robust in transgenic mice that overexpress nonmutated HER2 (Webster et al (1994) *Semin. Cancer Biol.* 5:69-76).

To improve tumor formation with nonmutated HER2, transgenic mice were produced using a HER2 cDNA plasmid in which an upstream ATG was deleted in order to prevent initiation of translation at such upstream ATG codons, which would otherwise reduce the frequency of translation initiation from the downstream authentic initiation codon of HER2 (for example, see Child et al (1999) *J. Biol. Chem.* 274: 24335-24341). Additionally, a chimeric intron was added to the 5 end, which should also enhance the level of expression as reported earlier (Neuberger and Williams (1988) *Nucleic Acids Res.* 16:6713; Buchman and Berg (1988) *Mol. Cell. Biol.* 8:4395; Brinster et al (1988) *Proc. Natl. Acad. Sci, USA* 85:836). The chimeric intron was derived from a Promega vector, Pci-neo mammalian expression vector (bp 890-1022). The cDNA 3'-end is flanked by human growth hormone axons 4 and 5, and polyadenylation sequences. Moreover, FVB mice were used because this strain is more susceptible to tumor development. The promoter from MMTV-LTR was used to ensure tissue-specific HER2 expression in the mammary gland. Animals were fed the AIN 76A diet in order to increase susceptibility to tumor formation (Rao et al (1997) *Breast Cancer Res. and Treatment* 45:149-158).

Fo5 Murine Mammary Tumor Model

The Fo5 model is a transgenic mouse model in which the human HER2 gene, under transcriptional regulation of the murine mammary tumor virus promoter (MMTV-HER2), is overexpressed in mammary epithelium. The overexpression causes spontaneous development of mammary tumors that overexpress the human HER2 receptor. The mammary tumor of one of the founder animals (founder #5 [Fo5]) has been propagated in subsequent generations of FVB mice by serial transplantation of tumor fragments. Before being used for an in vivo efficacy study, the MMTV-HER2 Fo5 transgenic mammary tumor was surgically transplanted into the No. 2/3 mammary fat pad of nu/nu mice (from Charles River Laboratories) in fragments that measured approximately 2×2 mm. When tumors reached desired volumes, the tumor-bearing mice were randomized and given a single dose by IV injection of the ADC.

Results

FIG. 1 shows a plot of the in vivo mean tumor volume change over time in breast cancer-model MMTV-HER2 Fo5 mammary allograft tumors inoculated into CRL nu/nu mice after single iv dosing on day 0 with: (1) Vehicle 20 mM Histidine acetate, pH 5.5, 240 mM sucrose, (2) xCD22-22 (103) at 10 mg/kg, (3) trastuzumab-22 (101) at 1 mg/kg, (4) trastuzumab-22 (101) at 3 mg/kg, and (5) trastuzumab-22 (101) at 10 mg/kg. The lines in the figure are indicated with the following symbols:

— Vehicle
— ADC101 Tmab HC A118C, 1 mg/kg
— ADC101 Tmab HC A118C, 3 mg/kg
— ADC101 Tmab HC A118C, 10 mg/kg
— ADC103 CD22 HC A118C, 10 mg/kg FIG. 2 shows a plot of the in vivo mean tumor volume change over time in breast cancer-model MMTV-HER2 Fo5 mammary allograft tumors inoculated into CRL flu/flu mice after single iv dosing on day 0 with: (1) Vehicle 20 mM Histidine acetate, pH 5.5, 240 mM sucrose, (2) xCD22-14 (112) at 6 mg/kg, (3) trastuzumab-14 (110) at 1 mg/kg, (4) trastuzumab-14 (110) at 3 mg/kg, (5) trastuzumab-14 (110) at 6 mg/kg, and (6) trastuzumab-22 (101) at 1 mg/kg. The lines in the figure are indicated with the following symbols:

— Vehicle
— ADC101 Tmab HC A118C, 1 mg/kg
— ADC110 Tmab HC A118C, 1 mg/kg
— ADC110 Tmab HC A118C, 3 mg/kg
— ADC110 Tmab HC A118C, 6 mg/kg
— ADC112 CD22 HC A118C, 6 mg/kg Abbreviations Ac acetyl
Acm acetamidomethyl
Alloc allyloxycarbonyl
Boc di-tert-butyl dicarbonate
t-Bu tert-butyl
Bzl benzyl, where Bzl-Ome is methoxybenzyl and Bzl-Me is methylbenzene
Cbz or Z benzyloxy-carbonyl, where Z—Cl and Z—Br are chloro- and bromobenzyloxy carbonyl respectively
DMF N,N-dimethylformamide
Dnp dinitrophenyl
DTT dithiothreitol
Fmoc 9H-fluoren-9-ylmethoxycarbonyl
imp N-10 imine protecting group: 3-(2-methoxyethoxy) propanoate-Val-Ala-PAB
MC-OSu maleimidocaproyl-O—N-succinimide
Moc methoxycarbonyl
MP maleimidopropenamide
Mtr 4-methoxy-2,3,6-trimethylbenzenesulfonyl
PAB para-aminobenzyloxycarbonyl
PEG ethyleneoxy
PNZ p-nitrobenzyl carbamate
Psec 2-(phenylsulfonyl)ethoxycarbonyl TBDMS tert-butyldimethylsilyl
TBDPS tert-butyldiphenylsilyl
Teoc 2-(trimethylsilyl)ethoxycarbonyl
Tos tosyl
Troc 2,2,2-trichlorethoxycarbonyl chloride
Trt trityl
Xan xanthyl

REFERENCES

The following references are incorporated by reference in their entirety:
EP 0522868
EP 0875569
EP 1295944
EP 1347046
EP 1394274
EP 1394274
EP 1439393
JP 05003790
JP 2004113151
JP 58180487
US 2001/055751
US 2002/034749
US 2002/042366
US 2002/150573
US 2002/193567
US 2003/0228319
US 2003/060612
US 2003/064397
US 2003/065143
US 2003/091580
US 2003/096961
US 2003/105292
US 2003/109676
US 2003/118592
US 2003/119121
US 2003/119122
US 2003/119125
US 2003/119126
US 2003/119128
US 2003/119129
US 2003/119130
US 2003/119131
US 2003/124140
US 2003/124579
US 2003/129192
US 2003/134790-A1
US 2003/143557
US 2003/157089
US 2003/165504
US 2003/185830
US 2003/186372
US 2003/186373
US 2003/194704
US 2003/206918
US 2003/219806
US 2003/224411
US 2003/224454
US 2003/232056
US 2003/232350
US 20030096743
US 20030130189
US 2003096743
US 2003130189
US 2004/0001827
US 2004/005320
US 2004/005538
US 2004/005563
US 2004/005598
US 2004/0101899
US 2004/018553
US 2004/022727
US 2004/044179
US 2004/044180
US 2004/101874
US 2004/197325
US 2004/249130
US 20040018194
US 20040052793
US 20040052793
US 20040121940
US 2005/271615
US 2006/116422
U.S. Pat. No. 4,816,567
U.S. Pat. No. 5,362,852
U.S. Pat. No. 5,440,021
U.S. Pat. No. 5,583,024
U.S. Pat. No. 5,621,002
U.S. Pat. No. 5,644,033
U.S. Pat. No. 5,674,713
U.S. Pat. No. 5,700,670
U.S. Pat. No. 5,773,223
U.S. Pat. No. 5,792,616
U.S. Pat. No. 5,854,399
U.S. Pat. No. 5,869,445
U.S. Pat. No. 5,976,551
U.S. Pat. No. 6,011,146
U.S. Pat. No. 6,153,408
U.S. Pat. No. 6,214,345
U.S. Pat. No. 6,218,519
U.S. Pat. No. 6,268,488
U.S. Pat. No. 6,518,404
U.S. Pat. No. 6,534,482
U.S. Pat. No. 6,555,339
U.S. Pat. No. 6,602,677
U.S. Pat. No. 6,677,435
U.S. Pat. No. 6,759,509
U.S. Pat. No. 6,835,807
U.S. Pat. No. 7,223,837
U.S. Pat. No. 7,375,078
U.S. Pat. No. 7,521,541
U.S. Pat. No. 7,723,485
WO 00/012508
WO 00/12507
WO 00/12508
WO 01/16318
WO 01/45746
WO 02/088172
WO 03/026577
WO 03/043583
WO 04/032828
WO 2000/12130
WO 2000/14228
WO 2000/20579
WO 2000/22129
WO 2000/32752
WO 2000/36107
WO 2000/40614
WO 2000/44899
WO 2000/55351
WO 2000/75655
WO 200053216
WO 2001/00244

WO 2001/38490
WO 2001/40269
WO 2001/40309
WO 2001/41787
WO 2001/46232
WO 2001/46261
WO 2001/48204
WO 2001/53463
WO 2001/57188
WO 2001/62794
WO 2001/66689
WO 2001/72830
WO 2001/72962
WO 2001/75177
WO 2001/77172
WO 2001/88133
WO 2001/90304
WO 2001/94641
WO 2001/98351
WO 2002/02587
WO 2002/02624
WO 2002/06317
WO 2002/06339
WO 2002/101075
WO 2002/10187
WO 2002/102235
WO 2002/10382
WO 2002/12341
WO 2002/13847
WO 2002/14503
WO 2002/16413
WO 2002/16429
WO 2002/22153
WO 2002/22636
WO 2002/22660
WO 2002/22808
WO 2002/24909
WO 2002/26822
WO 2002/30268
WO 2002/38766
WO 2002/54940
WO 2002/59377
WO 2002/60317
WO 2002/61087;
WO 2002/64798
WO 2002/71928
WO 2002/72596
WO 2002/78524
WO 2002/81646
WO 2002/83866
WO 2002/86443
WO 2002/88170
WO 2002/89747
WO 2002/92836
WO 2002/94852
WO 2002/98358
WO 2002/99074
WO 2002/99122
WO 2003/000842
WO 2003/002717
WO 2003/003906
WO 2003/003984
WO 2003/004989
WO 2003/008537
WO 2003/009814
WO 2003/014294
WO 2003/016475
WO 2003/016494
WO 2003/018621
WO 2003/022995
WO 2003/023013
WO 2003/024392
WO 2003/025138
WO 2003/025148
WO 2003/025228
WO 2003/026493
WO 2003/029262
WO 2003/029277
WO 2003/029421
WO 2003/034984
WO 2003/035846
WO 2003/042661
WO 2003/045422
WO 2003/048202
WO 2003/054152
WO 2003/055439
WO 2003/055443
WO 2003/062401
WO 2003/062401
WO 2003/072035
WO 2003/072036
WO 2003/077836
WO 2003/081210
WO 2003/083041
WO 2003/083047
WO 2003/083074
WO 2003/087306
WO 2003/087768
WO 2003/088808
WO 2003/089624
WO 2003/089904
WO 2003/093444
WO 2003/097803
WO 2003/101283
WO 2003/101400
WO 2003/104270
WO 2003/104275
WO 2003/105758
WO 2003004529
WO 2003042661
WO 2003104399
WO 2004/000997
WO 2004/001004
WO 2004/009622
WO 2004/011611
WO 2004/015426
WO 2004/016225
WO 2004/020595
WO 2004/022709
WO 2004/022778
WO 2004/027049
WO 2004/031238
WO 2004/032828
WO 2004/032842
WO 2004/040000
WO 2004/043361
WO 2004/043963
WO 2004/044178
WO 2004/045516
WO 2004/045520
WO 2004/045553
WO 2004/046342
WO 2004/047749
WO 2004/048938
WO 2004/053079
WO 2004/063355
WO 2004/063362
WO 2004/063709
WO 2004/065577
WO 2004/074320
WO 2004000221
WO 2004020583

WO 2004042346
WO 2004065576
WO 2005/023814
WO 2005/082023
WO 2005/085251
WO 2006/111759
WO 2007/044515
WO 2007/085930
WO 2009/052249
WO 2010/091150
WO 91/02536
WO 92/07574
WO 92/17497
WO 94/10312
WO 94/28931
WO 9630514
WO 97/07198
WO 97/44452
WO 98/13059
WO 98/37193
WO 98/40403
WO 98/51805
WO 98/51824
WO 99/28468
WO 99/46284
WO 99/58658
Am. J. Hum. Genet. 49 (3):555-565 (1991)
Amiel J., et al Hum. Mol. Genet. 5, 355-357, 1996
Amir et al (2003) Angew. Chem. Int. Ed. 42:4494-4499
Amsberry, et al (1990) J. Org. Chem. 55:5867
Angew Chem. Intl. Ed. Engl. (1994) 33:183-186
Annu. Rev. Neurosci. 21:309-345 (1998)
Arai H., et al J. Biol. Chem. 268, 3463-3470, 1993
Arai H., et al Jpn. Circ. J. 56, 1303-1307, 1992
Arima, et al., J. Antibiotics, 25, 437-444 (1972)
Attie T., et al, Hum. Mol. Genet. 4, 2407-2409, 1995
Auricchio A., et al Hum. Mol. Genet. 5:351-354, 1996
Barel M., et al Mol. Immunol. 35, 1025-1031, 1998
Barella et al (1995) Biochem. J. 309:773-779
Barnett T., et al Genomics 3, 59-66, 1988
Beck et al (1992) J. Mol. Biol. 228:433-441
Beck et al (1996) J. Mol. Biol. 255:1-13
Berge, et al., J. Pharm. Sci., 66, 1-19 (1977)
Biochem. Biophys. Res. Commun. (2000) 275(3):783-788
Biochem. Biophys. Res. Commun. 255 (2), 283-288 (1999)
Blood (2002) 100 (9):3068-3076
Blood 99 (8):2662-2669 (2002)
Blumberg H., et al Cell 104, 9-19, 2001
Bose, et al., Tetrahedron, 48, 751-758 (1992)
Bourgeois C., et al J. Clin, Endocrinol. Metab. 82, 3116-3123, 1997
Brinster et al (1988) Proc. Natl. Acad. Sci. USA 85:836
Buchman and Berg (1988) Mol. Cell. Biol. 8:4395
Cancer Res. 61 (15), 5857-5860 (2001)
Carl et al (1981) J. Med. Chem. 24:479-480
Carlsson et al (1978) Biochem. J. 173:723-737
Carter, P. (2006) Nature Reviews Immunology 6:343-357
Cell 109 (3):397-407 (2002)
CellTiter Glo Luminescent Cell Viability Assay, Promega Corp. Technical Bulletin TB288
Chakravarty et al (1983) J. Med. Chem. 26:638-644
Chan, J. and Watt, V. M., Oncogene 6 (6), 1057-1061 (1991)
Child et al (1999) J. Biol. Chem. 274: 24335-24341
Cho H.-S., et al Nature 421, 756-760, 2003
Ciccodicola, A., et al EMBO J. 8(7):1987-1991 (1989)
Clackson et al (1991) Nature, 352:624-628
Clark H. F., et al Genome Res. 13, 2265-2270, 2003
Corey E, Quinn J E, Buhler K R, et al. LuCap35: a new model of prostate cancer progression to androgen independence. The Prostate 2003; 55:239-46
Coussens L., et al Science (1985) 230(4730):1132-1139

Cree et al (1995) AntiCancer Drugs 6:398-404
Crouch et al (1993) J. Immunol. Meth. 160:81-88
Davis et al (2001) Proc. Natl. Acad. Sci. USA 98(17):9772-9777
de Groot et al (2001) J. Org. Chem. 66:8815-8830
de Groot et al (2003) Anger. Chem. Int. Ed. 42:4490-4494
Dennis et al. (2002) "Albumin Binding As A General Strategy For Improving The Pharmacokinetics Of Proteins" J Biol Chem. 277:35035-35043
Dobner et al (1992) Eur. J. Immunol, 22:2795-2799
Dornan et al (2009) Blood 114(13):2721-2729
Doronina et al (2006) Bioconj. Chem. 17:114-124
Dubowchik et al. Bioconjugate Chemistry, 2002, 13, 855-869
Dubowchik, et al. (1997) Tetrahedron Letters, 38:5257-60
Dumoutier L., et al J. Immunol. 167, 3545-3549, 2001
E. Schröder and K. Lübke, The Peptides, volume 1, pp 76-136 (1965) Academic Press
Ehsani A., et al (1993) Genomics 15, 426-429
Eliel, E. and Mien, S., "Stereochemistry of Organic Compounds", John Wiley & Sons, Inc., New York, 1994
Eishourbagy N. A., et al J. Biol. Chem. 268, 3873-3879, 1993
Erickson et al (2006) Cancer Res. 66(8):1-8
Feild, J. A., et al (1999) Biochem. Biophys. Res. Commun. 258 (3):578-582
Fields, G. and Noble, R. (1990) "Solid phase peptide synthesis utilizing 9-fluoroenylmethoxycarbonyl amino acids". Int. J. Peptide Protein Res. 35:161-214
Fuchs S., et al Mol. Med, 7, 115-124, 2001
Fujisaku et al (1989) J. Biol. Chem. 264 (4) 2118-2125)
Gary S. C., et al Gene 256, 139-147, 2000
Gaugitsch, H. W. et al (1992) J. Biol. Chem. 267 (16):11267-11273)
Geiser et al "Automation of solid-phase peptide synthesis" in Macromolecular Sequencing and Synthesis, Alan R. Liss, Inc., 1988, pp. 199-218
Genome Res. 13 (10):2265-2270 (2003)
Genomics 62 (2):281-284 (1999)
Geoghegan & Stroh, (1992) Bioconjugate Chem. 3:138-146
Getz et al (1999) Anal. Biochem. Vol 273:73-80
Glynne-Jones et al (2001) Int J Cancer. October 15; 94(2): 178-84
Gregson et al., Chem. Commun. 1999, 797-798
Gregson et al., J. Med. Chem. 2001, 44, 1161-1174
Gu Z., et al Oncogene 19, 1288-1296, 2000
Ha et al (1992) J. Immunol. 148(5):1526-1531
Haendler B., et al J. Cardiovasc. Pharmacol. 20, s1-S4, 1992
Hamann P. (2005) Expert Opin. Ther. Patents 15(9):1087-1103
Hamblett et al (2004) Clin. Cancer Res. 10:7063-7070
Handbook of Pharmaceutical Additives, 2nd Edition (eds. M, Ash and I. Ash), 2001 (Synapse information Resources, Inc., Endicott N.Y., USA)
Handbook of Pharmaceutical Excipients, 2nd edition, 1994
Hare, et al., J. Antibiotics, 41, 702-704 (1988)
Hashimoto et al (1994) Immunogenetics 40(4):287-295
Hay et al (1999) Bioorg. Med. Chem. Lett. 9:2237
Herdwijn, P et al., Canadian Journal of Chemistry. 1982, 60, 2903-7
Hermanson, G. T. (1996) Bioconjugate Techniques, Academic Press: New York, p 234-242
Hochlowski, et al., J. Antibiotics. 40, 145-148 (1987)
Hofstra R. M. W., et al Eur. J. Hum. Genet. 5, 180-185, 1997
Hofstra R. M. W., et al Nat. Genet, 12, 445-447, 1996
Hone et al (2000) Genomics 67:146-152
Hubert, R. S., et al (1999) Proc. Natl. Acad. Sci. U.S.A. 96 (25):14523-14528)
Hurley and Needham-VanDevanter, Acc. Chem. Res., 19, 230-237 (1986)
Immunogenetics 54 (2):87-95 (2002)

Int. Rev. Cytol. 196:177-244 (2000)
Itoh, et al., J. Antibiotics, 41, 1281-1284 (1988)
J. Biol. Chem. 270 (37):21984-21990 (1995)
J. Biol. Chem. 276 (29):27371-27375 (2001)
J. Biol. Chem. 277 (22):19665-19672 (2002)
J. Biol. Chem. 278 (33):30813-30820 (2003)
Janeway, C., Travers, P., Walport, M., Shlomchik (2001) Immuno Biology, 5th Ed., Garland Publishing, New York
Jeffrey et al (2005) J. Med. Chem. 4811344-1358
Jonsson et al (1989) Immunogenetics 29(6):411-413
Junutula, et al., 2008b Nature Biotech., 26(8):925-932
Kang, G-D., et al., Chem. Commun., 2003, 1680-1689
Kasahara et al (1989) Immunogenetics 30(1):66-68
King et al (2002) Tetrahedron Letters 43:1987-1990
Kingsbury et al (1984) J. Med. Chem. 27:1447
Kohler et al (1975) Nature 256:495
Kohn, in Antibiotics III. Springer-Verlag, New York, pp. 3-11 (1975).
Konishi, et al. J. Antibiotics, 37, 200-206 (1984)
Kovtun et al (2006) Cancer Res. 66(8):3214-3121
Kuhns J. J., et al J. Biol. Chem. 274, 36422-36427, 1999
Kuminoto, et al., J. Antibiotics, 33, 665-667 (1980)
Kurebayashi et al (1999) Brit. Jour. Cancer 79(5-6):707-717
Lab. Invest 82 (11):1573-1582 (2002)
Lambert J. (2005) Current Opin. in Pharmacol. 5:543-549
Langley and Thurston, J. Org. Chem., 52, 91-97 (1987)
Larhammar et al (1985) J. Biol. Chem. 260(26):14111-14119
Law et al (2006) Cancer Res. 66(4):2328-2337
Le et al (1997) FEBS Lett. 418(1-2):195-199
Leber, et al., J. Am. Chem. Soc., 110, 2992-2993 (1988)
Leimgruber, et al., J. Am. Chem. Soc., 87, 5791-5793 (1965)
Leimgruber, et al., J. Am. Chem. Soc., 87, 5793-5795 (1965)
Levenson et al (1997) Cancer Res. 57(15):3071-3078
Liang et al (2000) Cancer Res. 60:4907-12
Manfré, F. et al., J. Org. Chem. 1992, 57, 2060-2065
Marks et al (1991) J. Mol. Biol., 222:581-597
McDonagh (2006) Protein Eng. Design & Set 19(7): 299-307
Mendoza et al (2002) Cancer Res. 62:5485-5488
Miller et al (2003) Jour. of Immunology 170:4854-4861
Miura et al (1996) Genomics 38(3):299-304
Miura et al (1998) Blood 92:2815-2822
Moore M., et al Proc. Natl. Acad. Sci. U.S.A. 84, 9194-9198, 1987
Morrison et al (1984) Proc. Natl. Acad. Sci. USA, 81:6851-6855
Muller et al (1992) Eur. J. Immunol. 22 (6):1621-1625
Mungall A. J., et al Nature 425, 805-811, 2003
Nagase T., et al (2000) DNA Res. 7 (2):143-150)
Nakamuta M et al Biochem, Biophys. Res. Commun. 177, 34-39, 1991
Nakayama et al (2000) Biochem. Biophys. Res. Commun. 277(1):124-127
Naruse et al (2002) Tissue Antigens 59:512-519
Nature 395 (6699):288-291 (1998)
Neuberger and Williams (1988) Nucleic Acids Res. 16:6713
Novabiochem Catalog 2006/2007
Ogawa Y., et al Biochem. Biophys. Res. Commun. 178, 248-255, 1991
Okamoto Y et al Biol. Chem. 272, 21589-21596, 1997
Oncogene 10 (5):897-905 (1995)
Oncogene 14(11):1377-1382 (1997))
Parrish-Novak J., et al J. Biol. Chem. 277, 47517-47523, 2002
Payne, G. (2003) Cancer Cell 3:207-212
Phillips et al (2008) Cancer Res. 68(22):9280-9290
Pingault V., et al (2002) Hum. Genet. 111, 198-206
Pletnev S., et al (2003) Biochemistry 42:12617-12624
Preud'homme et al (1992) Clin. Exp. Immunol 90(1):141-146
Proc. Natl. Acad. Sat. U.S.A. (2003) 100 (7):4126-4131
Proc. Natl. Acad. Sci. U.S.A. 93 (1):136-140 (1996)
Proc. Natl. Acad. Sci. U.S.A. 98 (17):9772-9777 (2001)
Proc. Natl. Acad. Sci. U.S.A. 99 (26):16899-16903 (2002)
Proc. Natl. Acad. Sci. U.S.A. 96 (20):11531-11536 (1999)
Protective Groups in Organic Synthesis, Greene and Wuts, $3^{rd}$ Edition. 1999 John Wiley & Sons Inc.
Puffenberger E. G. et al Cell 79, 1257-1266, 1994
Rao et al (1997) Breast Cancer Res. and Treatment 45:149-158
Reiter R. E., et al Proc. Natl, Acad. Sci. U.S.A. 95, 1735-1740, 1998
Remington's Pharmaceutical Sciences, 20th edition, pub. Lippincott, Williams & Wilkins, 2000
Rodrigues et al (1995) Chemistry Biology 2:223
Ross et al (2002) Cancer Res. 62:2546-2553
S. P. Parker, Ed., McGraw-Hill Dictionary of Chemical Terms (84) McGraw-Hill Book Company, New York
Sakaguchi et al (1988) EMBO J. 7(11):3457-3464
Sakamoto A., Yanagisawa M., et al Biochem. Biophys. Res. Commun. 178, 656-663, 1991
Sanderson et al (2005) Clin. Cancer Res. 11:843-852
Semba K., et al Proc. Natl. Acad. Sci. U.S.A. 82, 6497-6501, 1985
Servenius et al (1987) J. Biol. Chem. 262:8759-8766
Shamis et al (2004) J. Am. Chem. Soc. 126:1726-1731
Sheikh F., et al (2004) J. Immunol. 172, 2006-2010
Shimizu, et al, Antibiotics, 29, 2492-2503 (1982)
Sinha S. K, et al (1993) J. Immunol. 150, 5311-5320
Storm et al (1972) J. Amer. Chem. Soc. 94:5815
Strausberg et al (2002) Proc. Natl. Acad. Sci. USA 99:16899-16903
Sun et al (2002) Bioorganic & Medicinal Chemistry Letters 12:2213-2215
Sun et al (2003) Bioorganic & Medicinal Chemistry 11:1761-1768
Svensson P. J., et al Hum. Genet. 103, 145-148, 1998
Swiercz J. M., et al J. Cell Biol. 165, 869-886, 2004
Syrigos and Epenetos (1999) Anticancer Research 19:605-614
Takeuchi, et al J. Antibiotics, 29, 93-96 (1976)
Tawaragi Y., et al Biochem. Biophys. Res. Commun. 150, 89-96, 1988
ten Dijke, P., et al Science 264 (5155):101-104 (1994)
Thompson, J. S., et al Science 293 (5537), 2108-2111 (2001) WO 2004/058309
Thurston, et al, Chem. Brit., 26, 767-772 (1990)
Thurston, et. al. Chem. Rev. 1994, 433-465 (1994)
Toki et al (2002) J. Org. Chem. 67:1866-1872
Tonnelle et al (1985) EMBO J. 4(11):2839-2847
Touchman et al (2000) Genome Res. 10:165-173
Trail et al (2003) Cancer Immunol. Immunother. 52:328-337
Tsunakawa, et al., J. Antibiotics, 41, 1366-1373 (1988)
Tsutsumi M., et al Gene 228, 43-49, 1999
Uchida et al (1999) Biochem. Biophys. Res. Commun. 266:593-602
Verheij J. B., et al Am. J. Med. Genet. 108, 223-225, 2002
Von Hoegen et al (1990) J. Immunol, 144(12):4870-4877
Webster et al (1994) Semin. Cancer Biol. 5:69-76
Weis J. J., et al J. Exp. Med. 167, 1647-1066, 1988
Weis J. J., et al Proc. Natl. Acad. Sci. U.S.A. 83, 5639-5643, 1986
Wilson et al (1991) J. Exp. Med. 173:137-146
Wu et al (2005) Nature Biotech. 23(9):1137-1145
Xie et al (2006) Expert. Opin. Biol. Ther. 6(3):281-291
Xu, M. J., et al (2001) Biochem. Biophys. Res. Commun. 280 (3):768-775 WO 2004/016225
Xu, X. Z., et al Proc. Natl. Acad. Sci. U.S.A. 98 (19):10692-10697 (2001)
Yamaguchi, N., et al Biol. Chem. 269 (2), 805-808 (1994)
Yamamoto T., et al Nature 319, 230-234, 1986
Yu et al (1992) J. Immunol, 148(2) 633-637

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial sequence
<220> FEATURE:
<223> OTHER INFORMATION: Synthetic sequence: A20FMDV-Cys polypeptide
      cell binding agent

<400> SEQUENCE: 1

(B) $R^2$ is independently selected from H, OH, =O, CN, R, OR, O—SO$_2$—R, CO$_2$R and COR, and $R^{12}$ is independently selected from =CH$_2$, =CH—R$^D$, =C(R$^D$)$_2$; or (C) $R^2$ and $R^{12}$ are each independently selected from H, OH, =O, CN, methyl, ethyl, propyl, butyl, C$_{3-12}$ cycloalkyl, C$_{2-12}$ alkynyl, optionally substituted C$_{3-20}$ heterocyclyl, optionally substituted C$_{8-10}$ aryl, OR, O—SO$_2$—R, and CO$_2$R COR.

2. The conjugate according to claim 1, wherein $R^{L1}$ and $R^{L2}$ are both H.

3. The conjugate according to claim 1, wherein $R^{L1}$ and $R^{L2}$ are both methyl.

4. The conjugate according to claim 1, wherein one of $R^{L1}$ and $R^{L2}$ is H and the other is methyl.

5. The conjugate according to claim 1, wherein Y is a single bond.

6. The conjugate according to claim 1, wherein Y is:

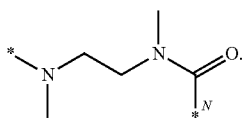

(A1)

7. The conjugate according to claim 1, wherein Y is:

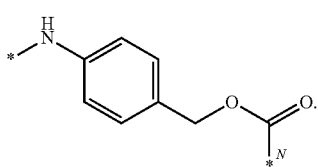

(A2)

8. The conjugate according to claim 1, wherein $R^9$ and $R^{19}$ are H.

9. The conjugate according to claim 1, wherein $R^6$ and $R^{16}$ are H.

10. The conjugate according to claim 1, wherein $R^7$ are $R^{17}$ are both OR$^{7A}$, where $R^{7A}$ is optionally substituted C$_{1-4}$ alkyl.

11. The conjugate of claim 10, wherein $R^{7A}$ is Me.

12. The conjugate according to claim 1, wherein X is O.

13. The conjugate according to claim 1, wherein $R^{11}$ is H.

14. The conjugate according to claim 1, wherein there is a double bond between C2 and C3 and C2' and C3' in each monomer unit.

15. The conjugate according to claim 14, wherein $R^2$ and $R^{12}$ are independently selected from H and R.

16. The conjugate according to claim 15, wherein $R^2$ and $R^{12}$ are independently R.

17. The conjugate according to claim 16, wherein $R^2$ and $R^{12}$ are independently optionally substituted C$_{5-20}$ aryl.

18. The conjugate according to claim 1, wherein $R^2$ is independently selected from =O, =CH$_2$, =CH—R$^D$, and =C(R$^D$)2.

19. The conjugate according to claim 1, wherein $R^{11}$ is a C$_3$ alkylene group or a C$_5$ alkylene group.

20. The conjugate according to claim 1, wherein the antibody or antibody fragment is an antibody or antibody fragment for a tumour-associated antigen.

21. The conjugate of claim 1 wherein the antibody or antibody fragment is an antibody which binds to one or more tumor-associated antigens or cell-surface receptors selected from (1)-(36):

(1) BMPR1B (bone morphogenetic protein receptor-type IB);
(2) E16 (LAT1, SLC7A5);
(3) STEAP1 (six transmembrane epithelial antigen of prostate);
(4) 0772P (CA125, MUC16);
(5) MPF (MPF, MSLN, SMR, megakaryocyte potentiating factor, mesothelin);
(6) Napi3b (NAPI-38, NPTIIb, SLC34A2, solute carrier family 34 (sodium phosphate), member 2, type II sodium-dependent phosphate transporter 3b);
(7) Sema 5b (FLJ10372, KIAA1445, Mm.42015, SEMASB, SEMAG, Semaphorin 5b Hlog, sema domain, seven thrombospondin repeats (type 1 and type 1-like), transmembrane domain (TM) and short cytoplasmic domain, (semaphorin) 5B);
(8) PSCA hlg (2700050C12Rik, C530008016Rik, RIKEN cDNA 2700050C12, RIKEN cDNA 2700050C12 gene);
(9) ETBR (Endothelin type B receptor);
(10) MSG783 (RNF124, hypothetical protein FLJ20315);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);
(12) TrpM4 (BR22450, FLJ20041, TRPM4, TRPM4B, transient receptor potential cation channel, subfamily M, member 4);
(13) CRIPTO (CR, CR1, CRGF, CRIPTO, TDGF1, teratocarcinoma-derived growth factor);
(14) CD21 (CR2 (Complement receptor 2) or C3DR (C3d/Epstein Barr virus receptor) or Hs 73792);
(15) CD79b (CD79B, CD79β, 1Gb (immunoglobulin-associated beta), B29);
(16) FcRH2 (IFGP4, IRTA4, SPAP1A (SH2 domain containing phosphatase anchor protein 1a), SPAP1B, SPAP1C);
(17) HER2;
(18) NCA;
(19) MDP;
(20) IL2ORα;
(21) Brevican;
(22) EphB2R;
(23) ASLG659;
(24) PSCA;
(25) GEDA;
(26) BAFF-R (B cell-activating factor receptor, BLyS receptor 3, BR3);
(27) CD22 (B-cell receptor CD22-B isoform);
(28) CD79a (CD79A, CD79a, immunoglobulin-associated alpha);
(29) CXCR5 (Burkitt's lymphoma receptor 1);
(30) HLA-DOB (Beta subunit of MHC class II molecule (Ia antigen));
(31) P2X5 (Purinergic receptor P2X ligand-gated ion channel 5);
(32) CD72 (B-cell differentiation antigen CD72, Lyb-2);
(33) LY64 (Lymphocyte antigen 64 (RP105), type I membrane protein of the leucine rich repeat (LRR) family);

(34) FcRH1 (Fc receptor-like protein 1);

(35) IRTA2 (Immunoglobulin superfamily receptor translocation associated 2); and

(36) TENB2 (putative transmembrane proteoglycan).

22. The conjugate of claim 1 wherein the antibody or antibody fragment is a cysteine-engineered antibody.

23. The conjugate of claim 1 wherein the antibody or antibody fragment is an antibody which binds to an ErbB receptor.

24. The conjugate of claim 23 wherein the antibody is trastuzumab.

25. The conjugate of claim 1 wherein Ab is an anti-HER2, an anti-Steap1, or an anti-CD22 antibody.

26. The conjugate according to claim 1 wherein the number of PBD moieties bound to each antibody (Ab) is an integer from 1 to about 8.

27. The conjugate according to claim 26, wherein the number of PBD moieties to each antibody is 1, 2, 3, or 4.

28. A composition of conjugates as defined in claim 26 comprising a mixture of the antibody-drug conjugate compounds, wherein the average number of PBD moieties per antibody in the mixture of antibody-drug conjugate compounds is about 2 to about 5.

29. A pharmaceutical composition comprising the conjugate of claim 1, and a pharmaceutically acceptable diluent, carrier or excipient.

30. The pharmaceutical composition of claim 29 further comprising a therapeutically effective amount of a chemotherapeutic agent.

31. A method of treating cancer comprising administering to a patient the pharmaceutical composition of claim 29.

32. The method of claim 31 wherein the patient is administered a chemotherapeutic agent, in combination with the conjugate.

33. A compound of formula (D):

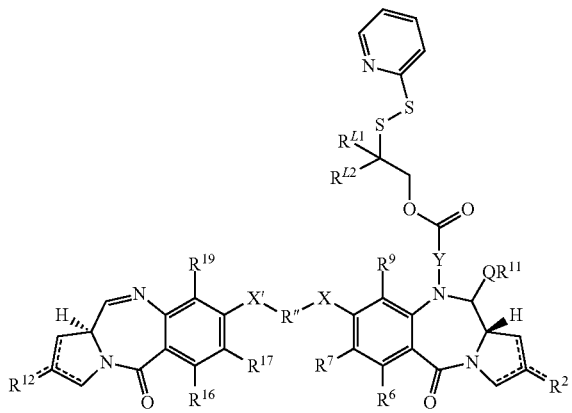

and salts and solvates thereof, wherein the dotted lines indicate the optional presence of a double bond between (a) C1 and C2 or C2 and C3 and (b) C1' and C2' or C2' and C3';

$R^2$, $R^6$, $R^7$, $R^9$, $R^{12}$, $R^{16}$, $R^{17}$, $R^{19}$, X, X', R", Y, $R^{L1}$ and $R^{L2}$ are as defined in claim 1.

34. A method of preparing a conjugate according to claim 1, the method comprising the step of reacting a cell binding agent with compound (D) as defined in claim 33.

35. An article of manufacture comprising a pharmaceutical composition of claim 29; a container; and a package insert or label indicating that the pharmaceutical composition can be used to treat cancer.

36. The conjugate according to claim 1, wherein, in condition (C), $R_2$ and $R_{12}$ are each independently selected from H, OH, =O, CN, methyl, ethyl, propyl, butyl, $C_{3-12}$ cycloalkyl, $C_{2-12}$ alkynyl, OR, O—$SO_2$—R and $CO_2R$ COR.

* * * * *